US012642811B2

(12) United States Patent
Faderl et al.

(10) Patent No.: US 12,642,811 B2
(45) Date of Patent: Jun. 2, 2026

(54) TREATMENT OF HEMATOLOGICAL DISORDERS

(71) Applicant: Jazz Pharmaceuticals Ireland Limited, Dublin (IE)

(72) Inventors: Stefan Faderl, Reno, NV (US); Ronald Cheung, Redwood City, CA (US); Qi Wang, Pennington, NJ (US)

(73) Assignee: Jazz Pharmaceuticals Ireland Limited, Dublin (IE)

( * ) Notice: Subject to any disclaimer, the term of this patent is extended or adjusted under 35 U.S.C. 154(b) by 0 days.

(21) Appl. No.: 18/632,083

(22) Filed: Apr. 10, 2024

(65) Prior Publication Data

US 2024/0252526 A1 Aug. 1, 2024

Related U.S. Application Data

(63) Continuation of application No. 17/530,245, filed on Nov. 18, 2021, now Pat. No. 11,980,636.

(60) Provisional application No. 63/115,540, filed on Nov. 18, 2020.

(51) Int. Cl.
| | |
|---|---|
| *A61K 31/704* | (2006.01) |
| *A61K 9/127* | (2006.01) |
| *A61K 31/635* | (2006.01) |
| *A61K 31/7068* | (2006.01) |
| *A61P 35/02* | (2006.01) |

(52) U.S. Cl.
CPC .......... *A61K 31/7068* (2013.01); *A61K 9/127* (2013.01); *A61K 31/635* (2013.01); *A61K 31/704* (2013.01); *A61P 35/02* (2018.01)

(58) Field of Classification Search
None
See application file for complete search history.

(56) References Cited

U.S. PATENT DOCUMENTS

| | | | |
|---|---|---|---|
| 3,932,657 | A | 1/1976 | Rahman |
| 4,610,868 | A | 9/1986 | Fountain et al. |
| 4,756,910 | A | 7/1988 | Yagi et al. |
| 4,769,250 | A | 9/1988 | Forssen |
| 4,780,535 | A | 10/1988 | Theodoropulos |
| 4,915,951 | A | 4/1990 | Baldeschwieler |
| 4,927,571 | A | 5/1990 | Huang et al. |
| 5,010,073 | A | 4/1991 | Kappas et al. |
| 5,059,421 | A | 10/1991 | Loughrey et al. |
| 5,077,056 | A | 12/1991 | Bally et al. |
| 5,145,684 | A | 9/1992 | Liversidge et al. |
| 5,166,319 | A | 11/1992 | Wrasidlo |
| 5,188,837 | A | 2/1993 | Domb |
| 5,225,212 | A | 7/1993 | Martin et al. |
| 5,330,768 | A | 7/1994 | Park et al. |
| 5,336,506 | A | 8/1994 | Josephson et al. |
| 5,393,530 | A | 2/1995 | Schneider et al. |
| 5,415,869 | A | 5/1995 | Straubinger et al. |
| 5,470,583 | A | 11/1995 | Na et al. |
| 5,543,158 | A | 8/1996 | Gref et al. |
| 5,663,387 | A | 9/1997 | Singh |
| 5,736,155 | A | 4/1998 | Bally et al. |
| 5,766,818 | A | 6/1998 | Smith et al. |
| 5,837,282 | A | 11/1998 | Fenske et al. |
| 5,869,103 | A | 2/1999 | Yeh et al. |
| 5,891,475 | A | 4/1999 | Perrin et al. |
| 5,928,832 | A | 7/1999 | Smith et al. |
| 6,045,821 | A | 4/2000 | Garrity et al. |
| 6,139,871 | A | 10/2000 | Hope et al. |
| 6,270,806 | B1 | 8/2001 | Liversidge et al. |
| 6,274,116 | B1 | 8/2001 | Hawthorne et al. |
| 6,429,200 | B1 | 8/2002 | Monahan et al. |
| 6,482,413 | B1 | 11/2002 | Chalasani et al. |
| 6,500,461 | B2 | 12/2002 | Perkins et al. |
| 6,559,243 | B1 | 5/2003 | Heinzman et al. |
| 6,673,612 | B2 | 1/2004 | Monahan et al. |
| 6,676,963 | B1 | 1/2004 | Lanza et al. |
| 6,679,822 | B2 | 1/2004 | Kubo et al. |
| 7,238,367 | B2 | 7/2007 | Tardi et al. |
| 7,744,921 | B2 | 6/2010 | Tardi et al. |
| 7,842,676 | B2 | 11/2010 | Janoff et al. |
| 7,850,990 | B2 | 12/2010 | Tardi et al. |
| 8,022,279 | B2 | 9/2011 | Mayer et al. |
| 8,092,828 | B2 | 1/2012 | Louie et al. |
| 8,431,806 | B2 | 4/2013 | Mayer et al. |
| 8,486,924 | B2 | 7/2013 | Ansell et al. |
| 8,518,437 | B2 | 8/2013 | Tardi et al. |
| 9,271,931 | B2 | 3/2016 | Tardi et al. |
| 10,028,912 | B2 | 7/2018 | Cabral-Lilly et al. |
| 10,166,184 | B2 | 1/2019 | Cabral-Lilly et al. |

(Continued)

FOREIGN PATENT DOCUMENTS

| | | |
|---|---|---|
| CN | 104114156 A | 10/2014 |
| CN | 113164502 A | 7/2021 |

(Continued)

OTHER PUBLICATIONS

Cincinnati Children's Hospital (https://clinicaltrials.gov/study/NCT03826992) (Year: 2019).*
Lancet et al (Journal of Clinical Oncology, 36(26), 2018, 2684-2694) (Year: 2018).*
Leighton et al (Mar. 21, 2016) chrome-extension://efaidnbmnn-nibpcajpcglclefindmkaj/https://www.accessdata.fda.gov/drugsatfda_docs/nda/2016/208573Orig1s000PharmR.pdf (Year: 2016).*
Ulm University Hospital, Aug. 18, 2018, //efaidnbmnn-nibpcajpcglclefindmkaj/https://www.uniklinik-duesseldorf.de/fileadmin/Fuer-Patienten-und-Besucher/Kliniken-Zentren-Institute/Kliniken/Klinik_fuer_Haematologie_Onkologie_und_Klinische_Immunologie/AML/AMLSG_30-18_Protocol_CPX-351_V1.4_1_Syn(Year: 2018).*
Ahl, P., et al., "Enhancement of the In Vivo Circulation Lifetime of L-a-Distearoylphosphatidylcholine Liposomes: Importance of Liposomal Aggregation Versus Complement Opsonization," Biochimica et Biophysica Acta, 1997, 1329:370-382.

(Continued)

*Primary Examiner* — Celeste A Roney

(74) *Attorney, Agent, or Firm* — Morgan, Lewis & Bockius, LLP

(57) ABSTRACT

The invention relates to compositions and methods for treating patients with hematological proliferative disorders with CPX-351, a liposomal composition of daunorubicin and cytarabine, and venetoclax.

19 Claims, 39 Drawing Sheets

(56) References Cited

U.S. PATENT DOCUMENTS

| | | |
|---|---|---|
| 10,835,492 B2 | 11/2020 | Cabral-Lilly et al. |
| 10,905,775 B2 | 2/2021 | Mayer et al. |
| 10,927,418 B2 | 2/2021 | Gordon et al. |
| 11,746,386 B2 | 9/2023 | Gordon et al. |
| 2003/0147945 A1 | 8/2003 | Tardi et al. |
| 2004/0052864 A1 | 3/2004 | Rubinfeld et al. |
| 2004/0152913 A1 | 8/2004 | Caprioli et al. |
| 2004/0221989 A1 | 11/2004 | Zhou et al. |
| 2008/0199515 A1* | 8/2008 | Louie .................. A61K 9/0019 514/50 |
| 2021/0393665 A1 | 12/2021 | Cheung et al. |
| 2022/0033892 A1 | 2/2022 | Sarwal et al. |
| 2023/0172855 A1 | 6/2023 | Cabral-Lilly et al. |
| 2023/0279503 A1 | 9/2023 | Gordon et al. |

FOREIGN PATENT DOCUMENTS

| | | |
|---|---|---|
| CN | 101878024 A | 12/2022 |
| CN | 115414376 A | 12/2022 |
| EP | 1744764 | 1/2007 |
| EP | 1786443 | 5/2007 |
| EP | 2187869 | 5/2010 |
| EP | 2222278 | 9/2010 |
| EP | 2344161 | 7/2011 |
| EP | 2768484 | 8/2014 |
| EP | 3300601 | 4/2018 |
| EP | 3572071 | 11/2019 |
| GB | 2187869 | 9/1987 |
| GB | 2222278 | 2/1990 |
| GB | 2256139 | 12/1992 |
| GB | 2344161 | 5/2000 |
| JP | 2001-026544 | 1/2001 |
| JP | 2001-302496 | 10/2001 |
| JP | 2002-363278 | 10/2001 |
| JP | 2003-026604 | 1/2003 |
| JP | 2007-533670 | 11/2007 |
| JP | 2007-316041 | 12/2007 |
| JP | 2009-513662 | 4/2009 |
| JP | 2010-519224 | 6/2010 |
| JP | 2011-504937 | 2/2011 |
| JP | 2011-171772 | 9/2011 |
| JP | 2014-532623 | 12/2014 |
| JP | 2017-160211 | 9/2017 |
| JP | 2018-150342 | 9/2018 |
| JP | 2018-535975 | 12/2018 |
| JP | 2022-502498 | 1/2022 |
| JP | 2022-024031 | 2/2022 |
| KR | 10-2010-0101121 | 10/2015 |
| KR | 10-2018-0108572 | 11/2016 |
| KR | 10-2014-0092323 | 9/2019 |
| KR | 10-2019-0111139 | 5/2020 |
| KR | 10-2021-0065962 | 6/2021 |
| KR | 10-2020-0057104 | 8/2021 |
| KR | 10-2021-0095746 | 10/2022 |
| KR | 10-2022-0141906 | 10/2022 |
| RU | 2014120475 A | 11/2015 |
| RU | 2018107407 | 2/2019 |
| RU | 2021111401 A | 10/2022 |
| WO | WO 1993/26019 | 12/1993 |
| WO | WO 1994/13265 | 6/1994 |
| WO | WO 1995/15762 | 6/1995 |
| WO | WO 1995/31217 | 11/1995 |
| WO | WO 1999/027908 | 6/1999 |
| WO | WO 1999/59545 | 11/1999 |
| WO | WO 1999/59547 | 11/1999 |
| WO | WO 2001/05372 | 1/2001 |
| WO | WO 2001/52826 | 7/2001 |
| WO | WO 2001/89653 | 11/2001 |
| WO | WO 2002/076970 | 10/2002 |
| WO | WO 2002/098465 | 12/2002 |
| WO | WO 2003/028696 | 4/2003 |
| WO | WO 2003/028697 | 4/2003 |
| WO | WO 2004/087105 | 10/2004 |
| WO | WO 2004/087115 | 10/2004 |
| WO | WO 2004/093795 | 11/2004 |
| WO | WO 2005/000266 | 1/2005 |
| WO | WO 2005/102359 | 11/2005 |
| WO | WO 2006/014626 | 2/2006 |
| WO | WO 2007/050784 | 5/2007 |
| WO | WO 2008/101214 | 8/2008 |
| WO | WO 2009/070761 | 6/2009 |
| WO | WO 2009/097011 | 8/2009 |
| WO | WO 2010/043050 | 4/2010 |
| WO | WO 2013/059133 | 4/2013 |
| WO | WO 2017/083592 | 5/2017 |
| WO | WO 2020/068979 | 4/2020 |

OTHER PUBLICATIONS

Akhtar, S., et al., "Interactions of Antisense DNA Oligonucleotide Analogs with Phospholipid Membranes (Liposomes)," Nucleic Acids Research, 1991, 19(20):5551-5559.

Alkan-Onyuksel, H. et al., "A Mixed Micellar Formulation Suitable for the Parenteral Administration of Taxol," Pharmaceutical Research, 1994, 11(2):206-212.

Allen, T. et al., "Drug Delivery Systems: Entering the Mainstream," Science, Mar. 19, 2004, 303:1818-1822.

Allen, T. et al., "Phosphatidylserine as a Determinant of Reticuloendothelial Recognition of Liposome Models of the Erythrocyte Surface," Proc. Natl. Acad. Sci. USA, Nov. 1998, 85:8067-8071.

Ansfield, F. et al., "Further Clinical Comparison Between 5-Fluorouracil (5-FU)[1] and 5-Fluoro-2'-Deoxyuridine (5-FUDR)[2,3,4]," Cancer Chemotherapy Reports, Oct. 1963, 32:101-105.

Bendas, G. et al., "Synthetic Glycolipids as Membrane-Bound Cryoprotectants in the Freeze-drying Process of Liposomes," European Journal of Pharmaceutical Sciences, 1996, 4:211-222.

Bouma, J. et al., "Anthracycline antitumour agents—A review of physicochemical, analytical and stability properties," Pharmaceutisch Weekblad Scientific Edition, 1986, 8:109-133.

Brodt, P., et al., "Inhibition of Murine Hepatic Tumor Growth by Liposomes Containing a Lipophilic Muramyl Dipeptide," Cancer Immunol. Immunother., 1989, 28:54-58.

Cao, S. et al., "Synergistic Antitumor Activity of Irinotecan in Combination with 5-Fluorouracil in Rats Bearing Advanced Colorectal Cancer: Role of Drug Sequence and Dose[1]," Cancer Research, Jul. 15, 2000, 60:3717-3721.

Celano, M. et al., "Cytotoxic effects of Gemcitabine-loaded liposomes in human anaplastic thyroid carcinoma cells," BMC Cancer, 2004, 4(63), 5 pages.

Chang, T.T. et al., "Rational Approach to the Clinical Protocol Design for Drug Combinations: A Review," Acta Paediatr. Tw., 2000, 41(6):294-302.

Chou, T.C. et al., "Quantitative Analysis of Dose-Effect Relationships: The Combined Effects of Multiple Drugs or Enzyme Inhibitors," Adv. Enzyme Reg., 1984, 22:27-55.

Cleek, R. et al., "Microparticles of poly(DL-lactic-co-glycolic acid)/ poly(ethylene glycol) blends for controlled drug delivery," Journal of Controlled Release, 1997, 48:259-268.

Cortes, J. et al., "High-dose liposomal daunorubicin and high-dose cytarabine combination in patients with refractory or relapsed acute myelogenous leukemia," Cancer Jul. 1, 2001, 92(1):7-14.

Coutinho, A. et al., "Metastatic Colorectal Cancer: System Treatment in the New Millennium," Cancer Control, May/Jun. 2003, 10(3):224-238.

Creaven, P. et al., "Phase I and pharmacokinetic evaluation of floxuridine/leucovorin given on the Roswell Park weekly regimen," Cancer Chemother. Pharmacol., 1994, 34:261-265.

Dinardo, C. et al., "A Phase 1b Study of Venetoclax (ABT-199/ GDC-0199) in Combination with Decitabine or Azacitidine in Treatment-Naïve Patients with Acute Myelogenous Leukemia Who Are ≥ to 65 Years and Not Eligible for Standard Induction Therapy," Blood, Dec. 3, 2015, 126(23):327, 5 pages.

European Medicines Agency—Science Medicines Health, "Vyxeos liposomal (previously known as Vyexos—daunorubicin / cyarabine," https://www.ema.europa.eu/en/medicines/human/EPAR/vyxeos-liposomal, accessed Oct. 17, 2023, 7 pages.

(56)                   References Cited

OTHER PUBLICATIONS

Farmer, M. et al., "Liposome-Encapsulated Hemoglobin as an Artificial Oxygen-Carrying System" Methods in Enzymology, 1987, 149:184-200.

Fisher, M., "Irinotecan/5-FU/leucovorin, oxaliplatin/5-FU/leucovorin, and oxaliplatin/irinotecan are each effective in the treatment of 5-FU-resistant advanced colorectal cancer," Clinical Colorectal Cancer, Aug. 2001, 1(2):85-86.

Fonseca, C. et al., "Paclitaxel-loaded PLGA nanoparticles: preparation, physicochemical characterization and in vitro anti-tumoral activity," Journal of Controlled Release, 2002, 83:273-286.

Fracasso, P. et al., "Phase I study of Pegylated Liposomal Doxorubicin and Gemcitabine in Patients with Advanced Malignancies," Cancer, Nov. 15, 2002, 95(10):2223-2229.

Frei, III, E. et al., "The relationship between high-dose treatment and combination chemotherapy: the concept of summation dose intensity," Clinical Cancer Research, Sep. 1998, 4:2027-2037.

Frerot, E. et al., "Controlled Stepwise Release of Fragrance Alcohols from Dendrimer-Based 2-Carbamoylbenzoates by Neighbouring Group Participation," Eur. J. Org. Chern., 2003, 967-971.

Friberg, L. et al., "Model of Chemotherapy-Induced Myelosuppression With Parameter Consistency Across Drugs," Journal of Clinical Oncology, Dec. 15, 2002, 20(24):4713-4721.

Giles, F. et al., "Adaptive randomized study of idarubicin and cytarabine versus troxacitabine and cytarabine versus troxacitabine and idarubicin in untreated patients 50 years or older with adverse karyotype acute myeloid leukemia," Journal of Clinical Oncology, May 1, 2003, 21(9):1722-1727.

Gokhale, PC et al., "An improved method of encapsulation of doxorubicin in liposomes: pharmacological, toxicological and therapeutic evaluation," British Journal of Cancer, 1996, 74(1):43-48.

Goodrich, R. et al., "Alterations in Membrane Surfaces Induced by Attachment of Carbohydrates," Biochemistry, 1991, 30(21):5313-5318.

Greenwald, R. et al., "Poly(ethylene glycol) Conjugated Drugs and Prodrugs: A Comprehensive Review," Critical Reviews in Therapeutic Drug Carrier Systems, 2000, 17(2):101-161.

Greenwald, R., "PEG drugs: an overview," Journal of Controlled Release, 2001, 74:159-171.

Greenwald, R. et al., "Drug Delivery Systems: Water Soluble Taxol 2'-Poly(ethylene glycol) Ester Prodrugs-Design and in Vivo Effectiveness," J. Med. Chem. 1996, 39:424-431.

Gref, R. et al., "'Stealth' corona-core nanoparticles surface modified by polyethylene glycol (PEG): influences of the corona (PEG chain length and surface density) and of the core composition on phagocytic uptake and plasma protein adsorption," Colloids and Surfaces, 2000, 18:301-313.

Gupta, M. et al., "BRG1 loss predisposes lung cancers to replicative stress and ATR dependency," Cancer Res., Sep. 15, 2020, 80(18):3841-3854.

Hayashi, H. et al., "The effects of delayed treatment with sialyl Lewis X against lipopolysaccharide-induced acute lung injury in rabbits," European Journal of Pharmacology, 2000, 392:109-116.

International Search Report and Written Opinion for International Application No. PCT/CA2005/000625, mailed on Aug. 11, 2005, 13 pages.

International Search Report and Written Opinion for International Application No. PCT/US05/025549, mailed on Aug. 14, 2006, 5 pages.

International Search Report and Written Opinion for International Application No. PCT/US2006/041832, mailed on Apr. 24, 2007, 10 pages.

Kao, Y. et al., "Pharmacological Disposition of Negatively Charged Phospholipid Vesicles in Rats" Journal of Pharmaceutical Sciences, Nov. 1980, 69(11):1338-1349.

Kemeny, N. et al., "Hepatic-arterial chemotherapy," The Lancet Oncology, Jul. 2001, 2:418-428.

Kim, S.Y. et al., "Poly(ethylene oxide)-poly(propylene oxide)-poly(ethylene oxide)/poly(e-caprolactone) (PCL) amphiphilic block copolymeric nanospheres II. Thermo-responsive drug release behaviors," Journal of Controlled Release, 2000, 65:345-358.

Kirby, C. et al., "Effect of the Cholesterol Content of Small Unilamellar Liposomes on their Stability In Vivo and In Vitro," Biochem. J., 1980, 186:591-598.

Lamprecht, A. et al., "Influences of process parameters on nanoparticle preparation performed by a double emulsion pressure homogenization technique," International Journal of Pharmaceutics, 2000) 196:177-182.

Lancet, J. et al., "CPX-351 (cytarabine and daunorubicin) Liposome for Injection Versus Conventional Cytarabine Plus Daunorubicin in Older Patients With Newly Diagnosed Secondary Acute Myeloid Leukemia," Journal of Clinical Oncology, Sep. 10, 2018, 36(26):2684-2692.

Lancet, J. et al.,"CPX-351 versus 7+3 cytarabine and daunorubicin chemotherapy in older adults with newly diagnosed high-risk or secondary acute myeloid leukaemia: 5-year results of randomized, open-label, multicentre, phase 3 trial," Articles, Lancet Haematol, 2021, 8(7):e481-e491.

Lemoine, D. et al., Stability study of nanoparticles of poly($\varepsilon$-caprolactone), poly(D,L-lactide) and poly(D,L-lactide-co-glycolide), Biomaterials, 1996, 17:2191-2197.

Li, C., "Poly(L-glutamic acid)—anticancer drug conjugates," Advanced Drug Delivery Reviews, 2002, 54(5):695-713.

Litvak, D. et al., "Systemic Irinotecan and Regional Floxuridine After Hepatic Cytoreduction in 185 Patients With Unresectable Colorectal Cancer Metastases," Annals of Surgical Oncology, 2002, 9(2):148-155.

Lundberg, B., "A Submicron Lipid Emulsion Coated with Amphipathic Polyethylene Glycol for Parenteral Administration of Paclitaxel (Taxol)," J. Pharm. Pharmacal., 1997, 49:16-21.

Mayer, L. et al., "Ratiometric dosing of anticancer drug combinations: Controlling drug ratios after systemic administration regulates therapeutic activity in tumor-bearing mice," Mol. Cancer Ther., Jul. 2006, 5(7):1854-1863.

Mccullough, J., "Overview of Platelet Transfusion," Seminars in Hematology, Jul. 2010, 47(3):235-242.

Meta-Analysis Group In Cancer, "Reappraisal of Hepatic Arterial Infusion in the Treatment of Nonresectable Liver Metastases From Colorectal Cancer," Articles, Journal of the National Cancer Institute, Mar. 6, 1996, 88(5), 252-258.

Mu, L. et al., "A novel controlled release formulation for the anticancer drug paclitaxel (Taxol®): PLGA nanoparticles containing vitamin E TPGS," Journal of Controlled Release, 2003, 86:33-48.

Nishiyama, N. et al., "Novel Cisplatin-Incorporated Polymeric Micelles Can Eradicate Solid Tumors in Mice," Cancer Research, Dec. 15, 2003, 63:8977-8983.

Nishiyama, N. et al., "Preparation and characterization of size-controlled polymeric micelle containing cis-dichlorodiammineplatinum(II) in the core," Journal of Controlled Release, 2001, 74:83-94.

Niu, X. et al., "Binding of released Bim to Mcl-1 is a mechanism of intrinsic resistance to ABT-199 which can be overcome by combination with daunorubicin or cytarabine in AML cells," Clin. Cancer Res., Sep. 1, 2016, 22(17):4440-4451.

Ogihara-Umeda, I., et al., "Cholesterol enhances the delivery of liposome-encapsulated gallium-67 to tumors," Eur. J. Nucl. Med., 1989, 15:612-617.

Ohya, Y. et al., "Design of Poly(ethylene glycol) Immobilizing Platinum Complex through Chelate-type Coordination Bond," Polym. Adv. Technol., 2000, 11:635-641.

Olbrich, C. et al., "Lipid-Drug-Conjugate (LDC) Nanoparticles as Novel Carrier System for the Hydrophilic Antitrypanosomal Drug Diminazenediaceturate," Journal of Drug Targeting, 2002, 10(5):387-396.

Perkins, W. et al., "Novel therapeutic nano-particles (lipocores): trapping poorly water soluble compounds," International Journal of Pharmaceutics, 2000, 200:27-39.

Pettit, K. et al., "Defining and Treating Older Adults with Acute Myeloid Leukemia Who Are Ineligible for Intensive Therapies," Dec. 14, 2015, 5(280):1-5.

(56)                    References Cited

OTHER PUBLICATIONS

Pitot, H. et al., "Phase II Trial of Irinotecan in Patients With Metastatic Colorectal Carcinoma," Journal of Clinical Oncology, Aug. 1997, 15(8):2910-2919.

Rivera, E. et al., "Phase I Study of Stealth Liposomal Doxorubicin in Combination With Gemcitabine in the Treatment of Patients With Metastatic Breast Cancer," Journal of Clinical Oncology, Mar. 15, 2001, 19(6):1716-1722.

Rivera, E. et al., "Phase II Study of Pegylated Liposomal Doxorubicin in Combination With Gemcitabine in Patients With Metastatic Breast Cancer," Journal of Clinical Oncology, Sep. 1, 2003, 21(17):3249-3254.

Rivera, E., "Liposomal Anthracyclines in Metastatic Breast Cancer: Clinical Update," The Oncologist, 2003, 8(Suppl 2):3-9.

Rougier, P. et al., "Phase II Study of Irinotecan in the Treatment of Advanced Colorectal Cancer in Chemotherapy—Naïve Patients and Patients Pretreated With Fluorouracil-Based Chemotherapy," J. Clin. Oncol., 1997, 15:251-260.

Shiah, J.-G. et al., "Combination chemotherapy and photodynamic therapy of targetable N-(2-hydroxypropyl)methacrylamide copolymer-doxorubicin/mesochlorin e$_6$-OV-TL 16 antibody immunoconjugates," Journal of Controlled Release, 2001, 74:249-253.

Soo, P. et al., "Incorporation and Release of Hydrophobic Probes in Biocompatible Polycaprolactone-block-poly(ethylene oxide) Micelles: Implications for Drug Delivery," Langmuir, 2002 18:9996-10004.

Soo, P. et al., "Polycaprolactone-block-poly(ethylene oxide) Micelles: A Nanodelivery System for 17β-Estradiol," Molecular Pharmaceutics, Jun. 10, 2005, 2(6):519-527.

Spiers, A. et al., "Prolonged remission maintenance in acute myeloid leukaemia," British Medical Journal, 1977, 2:544-547.

Tallman, M. et al., "Drug therapy for acute myeloid leukemia," Blood, Aug. 15, 2005, 106(4):1154-1163.

Thigpen, T., "The Role of Gemcitabine-Based Doublets in the Management of Ovarian Carcinoma," Seminars in Oncology, Feb. 2002, 29(1, Suppl. 1):11-16.

Torchilin, V. et al., "Liposomes and Micelles to Target the Blood Pool for Imaging Purposes," Journal of Liposome Research, 2000, 10(4): 483-499.

Tracy, M.A. et al., "Factors affecting the degradation rate of poly(lactide-co-glycolide) microspheres in vivo and in vitro," Biomaterials, 1999, 20(11):1057-1062.

Trubetskoy, V. et al., "Use of polyoxyethylene-lipid conjugates as long-circulating carriers for delivery of therapeutic and diagnostic agents," Advanced Drug Delivery Reviews, 1995, 16(2-3):311-320.

Vaage, J. et al., "Therapy of Mouse Mammary Carcinomas with Vincristine and Doxorubicin Encapsulated in Sterically Stabilized Liposomes," Int. J. Cancer, 1993, 54(1):959-964.

Van Laar, J.A.M. et al., "Comparison of 5-Fluoro-2'-deoxyuridine with 5-Flurouracil and their Role in the Treatment of Colorectal Cancer," European Journal of Cancer, 1998, 34(3):296-306.

Vodovozova,E.L. et al., "Antitumour activity of cytotoxic liposomes equipped with selection ligand SiaLe$^x$, in a mouse mammary adenocarcinoma model", European Journal of Cancer, 2000, 36:942-949.

Vyxeos, Daunorubicin and cytarabine liposome for injection—Powder, 44 mg daunorubicin and 100 mg cytarabine per vial, intravenous infusion—Antineoplastic Agent, Apr. 28, 2021, 1-41.

Wang, Q. et al., "CPX-351 Population Pharmacokinectics in Patients with Hematologic Malignancies," Blood, Dec. 7, 2017, 130(Suppl_1):5064, 3 pages.

Wheeler, J. et al., "Polyethylene Glycol Modified Phospholipids Stabilize Emulsions Prepared from Triacylglycerol," Journal of Pharmaceutical Sciences, Nov. 1994, 83(11):1558-1564.

Yates, J. et al., "Cytosine Arabinoside With Daunorubicin or Adriamycin for Therapy of Acute Myelocytic Leukemia: A CALGB Study," Blood, Aug. 1982, 60(2):454-462.

* cited by examiner

PK-PD Model for Myelosuppression

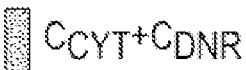

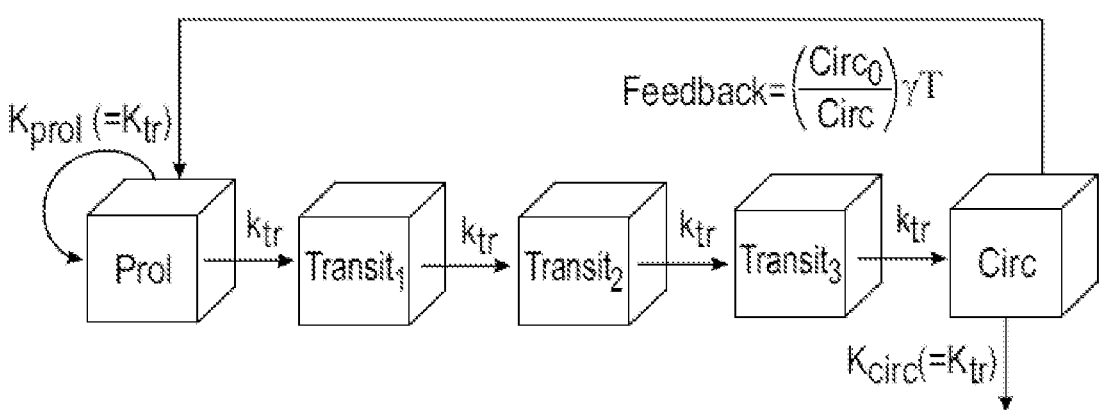

$$\frac{dProl}{dt} = k_{prol} \cdot Prol \cdot \left( 1 - \frac{Imax \cdot (C_{CYT} + C_{DNR})^{\gamma}}{IC_{50}^{\gamma} + (C_{CYT} + C_{DNR})^{\gamma}} \right) \cdot \left( \frac{Circ_0}{Circ} \right)^{\gamma\tau} - k_{tr} \cdot Prol$$

$$\frac{dTransit_1}{dt} = k_{tr} \cdot Prol - k_{tr} \cdot Transit_1$$

$$\frac{dTransit_2}{dt} = k_{tr} \cdot Transit_1 - k_{tr} \cdot Transit_2$$

$$\frac{dTransit_3}{dt} = k_{tr} \cdot Transit_2 - k_{tr} \cdot Transit_3$$

$$\frac{dCirc}{dt} = k_{tr} \cdot Transit_3 - k_{circ} \cdot Circ$$

*FIG 1A*

Cycle 1

Cycle 2, 3 or 4

GOF (goodness-of-fit) Plots: Final CPX-351 PK-PD Model for Platelets

GOF (goodness-of-fit) Plots: Base CPX-351 PK-PD
Model for Neutrophils

VPC (Visual Predictive Checks): Final CPX-351 PK-PD
Model for Neutrophils

Induction 1

Induction 2,3 or 4

FIG. 7

Day 1. Vyxeos is Dosed on Day 1

Day 1, 3. Vyxeos is Dosed on Day 1 and 3

Day 1, 5. Vyxeos is Dosed on Day 1 and 5

Day 1, 8. Vyxeos is Dosed on Day 1 and 8

Day 1, 8, 15. Vyxeos is Dosed on Day 1, 8, and 15

Day 1, 3, 5. Vyxeos is Dosed on Day 1,3 and 5 at 100 unit/m2

7+3. Standard of Care 7 Days Cytarabine +3 Days

Daunorubicin

| CD 34 Status | IDH1/2 Status | FLT3 Status | NPM status |
|---|---|---|---|
| CD 34 | Wild Type | ITD Mutant | Wild Type |

\*=Incomplete Curve

|  | IC50(pM) |
|---|---|
| CPX-351 | 41096 |
| CPX-351 + Venetoclax | 3.2\* |
| Venetoclax | 11847\* |

*FIG. 12B*

| Test group | IC50(pM) |
|---|---|
| CPX-351 | 2014 |
| CPX-351+ Venetoclax | 1084 |
| Venetoclax | 8568 |

| CD34 Status | IDH1/2 Status | FLT3 Status | NPM Status |
|---|---|---|---|
| CD34+ Small Subset/Variable | IDH2 Mutant (R140Q) | ITD Mutant | Wild Type |

TREATMENT OF HEMATOLOGICAL DISORDERS

CROSS-REFERENCE TO RELATED APPLICATION

This application is a continuation application of application Ser. No. 17/530,245, filed on Nov. 18, 2021, which claims priority to and the benefit of U.S. Provisional Application No. 63/115,540, filed on Nov. 18, 2020, the disclosures of which are incorporated herein by reference in their entirety.

PARTIES TO JOINT RESEARCH AGREEMENT

The subject matter was developed and the claimed invention was made by or on behalf of one or more parties to a joint research agreement that was in effect on or before the effective filing date of the claimed invention, and the claimed invention was made as a result of activities undertaken within the scope of the joint research agreement. The parties to the joint research agreement are Jazz Pharmaceuticals Ireland Limited and The University of Texas M. D. Anderson Cancer Center.

FIELD

The invention relates to compositions and methods the treatment of hematological conditions that are susceptible to treatment with combinations of cytidine analogues and anthracyclines, and to increase the likelihood of receiving an allogeneic stem cell transplant (SCT).

BACKGROUND

Combination chemotherapies comprising cytidine analogues and anthracycline agents have been well studied for treatment against various cancers or hematologic proliferative disorders. Drug cocktails of the cytidine analogue, cytarabine, and an anthracycline such as daunorubicin demonstrate some efficacy in patients with hematologic malignancies. See, e.g., Tallum et al., *Blood* 106:2243 (2005).

Cytarabine (cytosine arabinoside, Ara-C or 1-β-D-arabinofuranosylcytosine) is a cell cycle phase-specific antineoplastic agent, affecting cells predominantly during the S-phase of cell division. Intracellularly, cytarabine is converted into cytarabine-5'-triphosphate (ara-CTP), which is the active metabolite. The mechanism of action is not completely understood, but it appears that ara-CTP acts primarily through inhibition of DNA polymerase. Incorporation into DNA and RNA may also contribute to cytarabine cytotoxicity. Cytarabine is cytotoxic to a wide variety of proliferating mammalian cells in culture.

Daunorubicin hydrochloride is the hydrochloride salt of an anthracycline cytotoxic antibiotic produced by a strain of *Streptomyces coeruleorubidus*. Daunorubicin has antimitotic and cytotoxic activity through a number of proposed mechanisms of action. Daunorubicin forms complexes with DNA by intercalation between base pairs. It inhibits topoisomerase II activity by stabilizing the DNA-topoisomerase II complex, preventing the religation portion of the ligation-religation reaction that topoisomerase II catalyzes. Single strand and double strand DNA breaks result. Daunorubicin may also inhibit polymerase activity, affect regulation of gene expression, and produce free radical damage to DNA. Daunorubicin possesses an antitumor effect against a wide spectrum of animal tumors, either grafted or spontaneous.

Since 1973, cytarabine combined with an anthracycline has been the standard first-line therapy for acute myelogenous leukemia (AML), against which other regimens are compared. Until recently, the standard of care for AML has been a combination of cytarabine and daunorubicin administered in the classic "7+3" regimen with cytarabine administered for 7 consecutive days and daunorubicin for the first 3 of those 7 consecutive days. Addition of other agents such as 6-thioguanine or etoposide and changes in the dose or schedule of administration have been studied to improve outcomes, but while incremental gains have been made, the 40-year old use of an anthracycline and cytarabine remained the basis for standard induction treatment in AML.

In 2017, Vyxeos® (also known as "CPX-351" and used interchangeably here), a fixed-dose liposomal combination of cytarabine and daunorubicin at a 5:1 ratio which delivers the administered ratio to the patient over time was approved by the FDA for the treatment of adults with two types of high-risk acute myeloid leukemia (AML): newly diagnosed therapy-related AML (t-AML) or AML with myelodysplasia-related changes (AML-MRC). CPX-351 showed a significant improvement in overall survival in these patients compared to the standard 7+3 therapy. Results from earlier clinical studies also showed favorable results for treatment of other leukemias or hematological disorders such as myelodysplastic syndromes (MDS) and certain lymphoblastic leukemias/lymphomas.

Venetoclax is a BCL-2 inhibitor used in combination with low-dose cytarabine or hypomethylating agents in patients with AML who are considered ineligible for intensive chemotherapy. The active drugs within CPX-351, daunorubicin and cytarabine, have been shown to bypass an intrinsic resistance mechanism associated with venetoclax, resulting in synergistic cell death when used in combination. CPX-351 plus venetoclax also consistently showed synergistic or additive effects in tested acute leukemia cell lines.

Unfortunately, due to age and/or co-morbidities, many patients with hematological malignancies are ineligible to receive standard intensive chemotherapy (ICT), i.e., ISICT patients or subjects, including approximately 50% of AML patients. The standard therapies for these ISICT patients are hypomethylating agents (HMAs) and low dose cytarabine (LDAC). However, the single agent activity of HMAs and LDAC is discouraging with response rates less than about 20% and a median overall survival of only 7-10 months.

Recognizing that there remains a need to achieve improved efficacy for all patients (including ISICT patients), a combination of CPX-351 and Venetoclax was identified as a therapy providing the sought-after improved efficacy in addition to other benefits, such as, inter alia, improving the likelihood of allogenic stem cell transplant (SCT).

SUMMARY

The invention relates to compositions and methods for treating patients with hematological proliferative disorders with CPX-351, a liposomal composition of daunorubicin and cytarabine, and venetoclax.

DESCRIPTION OF THE DRAWINGS

FIG. 1A is schematic of a model used for PK/PD myelosuppression.

Figure 7:
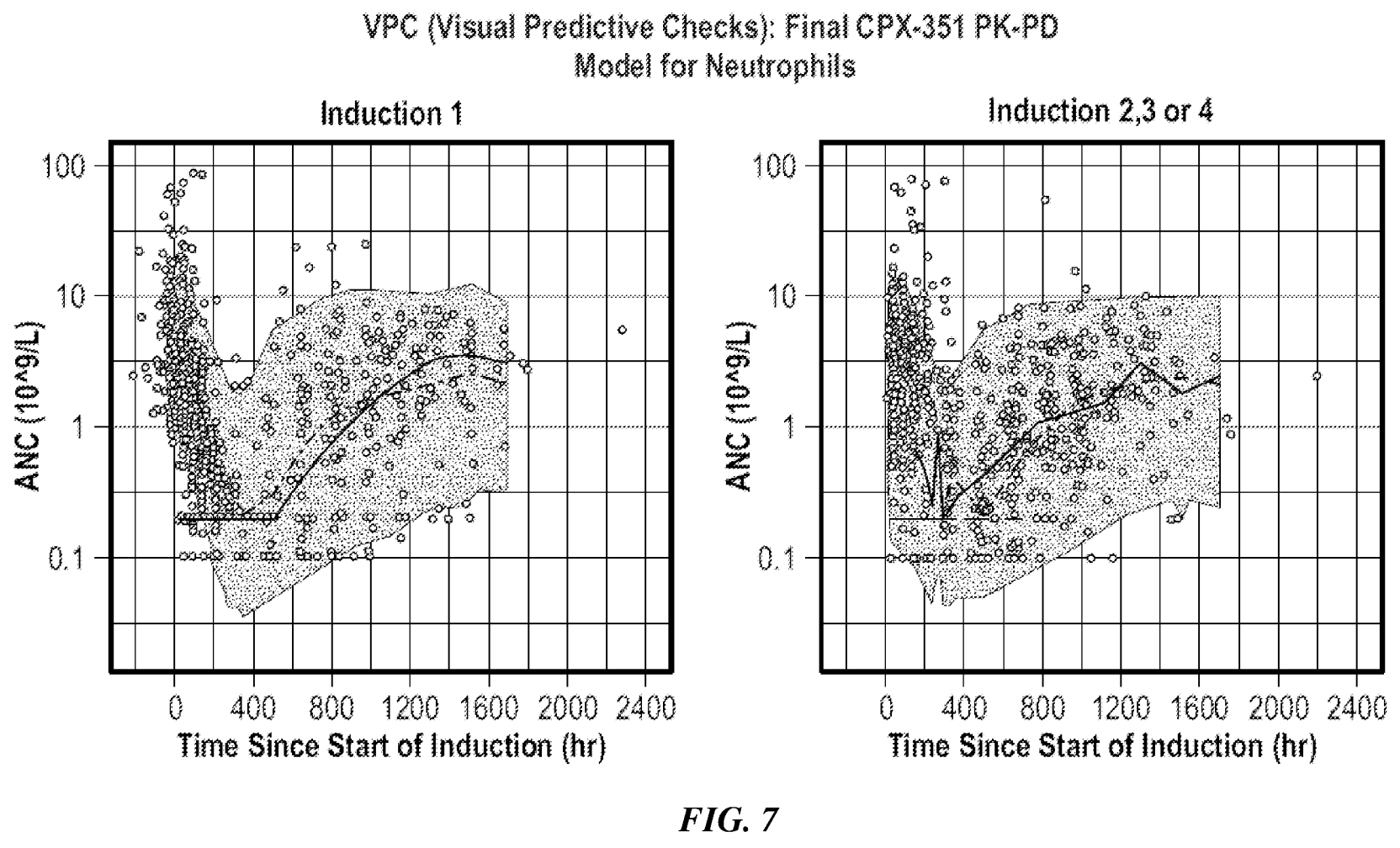

FIG. 7 shows the VPC (Visual Predictive Checks): Final CPX-351 PK-PD Model for Neutrophils.

FIGS. 12A-12B and 13A-13B show the change in $IC_{50}$ for the CTG-2226 and CTG-2233, cell lines respectively.

DETAILED DESCRIPTION

Figure 1B:
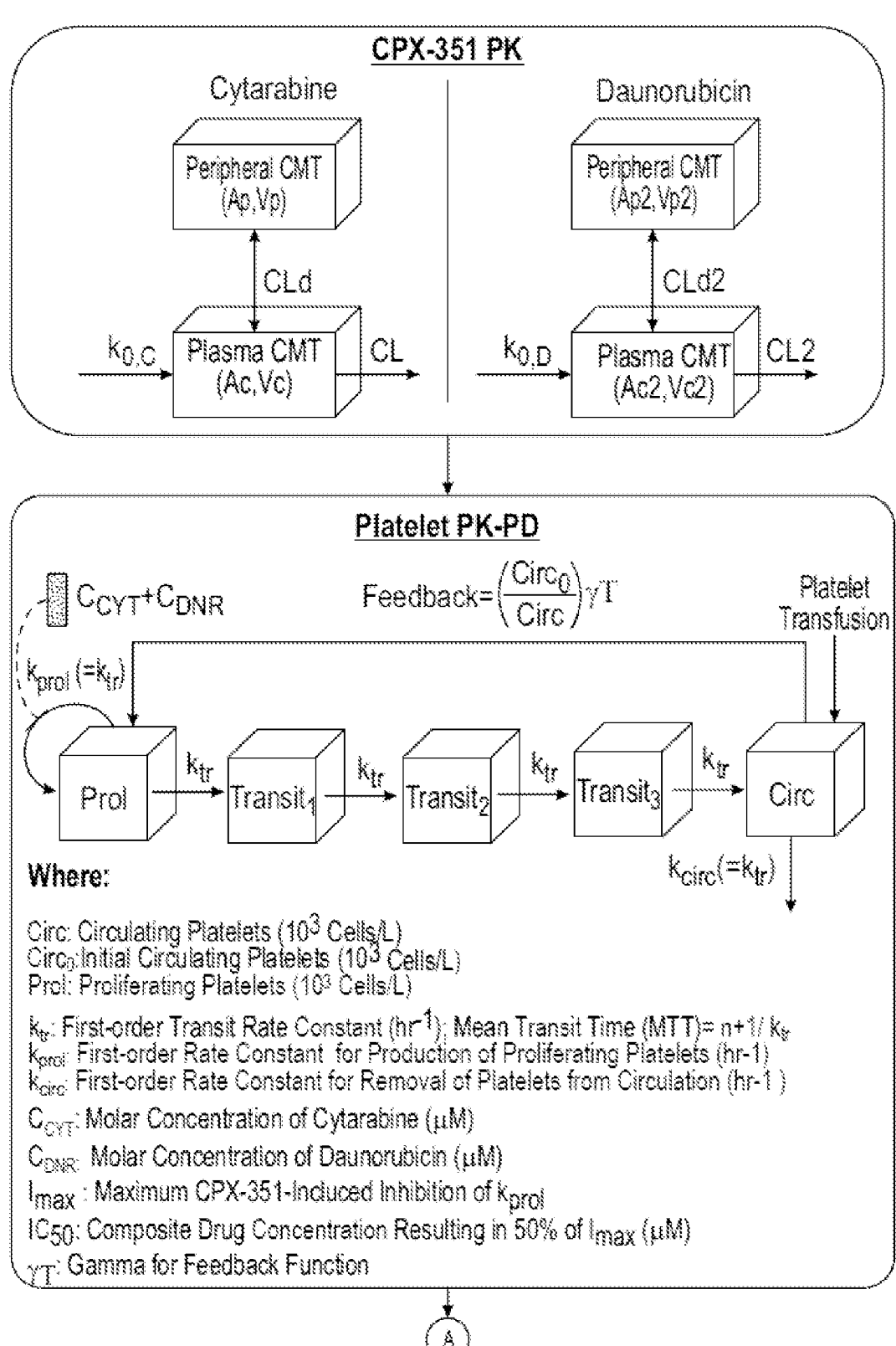
FIGS. 1B-1E show a summary of Population PK and PK-PD Models.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

Definitions

As used herein, "a" or "an" means "at least one" or "one or more."

Abbreviations used herein include: PK, pharmacokinetic; PD, pharmacodynamic; CMT, compartment; Ap, peripheral amount of drug; Vp, peripheral volume of distribution; CLd, distribution clearance; $k_o$, 0-order rate constant; Ac, central amount of drug; Vc, central volume of distribution; CL, clearance; GCSF, granulocyte colony-stimulating factor; SC, subcutaneous; F, bioavailability; $k_a$, first-order absorption rate constant; D, dose; CL, clearance; $K_D$, equilibrium dissociation constant for GCSF and GCSF receptor R, accumulation ratio; $K_{int}$, first-order rate constant for internalization of GCSF receptor complexed with filgrastim or pegfilgrastim; ko, dissociation constant; IV, intravenous; ANC, absolute neutrophil count.

By "low-intensity therapy", "low intensity treatment, "LIT", or "low dose treatment" or "low dose therapy", it is meant to include both a lower individual dose and/or less dosages in the dosing schedule. For example, weekly or monthly schedule, such as an Induction treatment/therapy or Consolidation treatment/therapy, which is lower and/or less intense than a similar therapy used in cancer patients who may qualify for ICT is also included. Specifically "low dose CPX-351 treatment" may be a lower dose and/or weekly or 28-day dosing schedule that has less dosages than that used in Study 301.

The development of Vyxeos® (Jazz Pharmaceuticals) (CPX-351), cytarabine:daunorubicin liposome injection was based on 1) defining a non-antagonistic ratio of the two active moieties, cytarabine and daunorubicin, using cell-based screening assays and 2) designing a liposomal drug carrier to maintain this ratio after intravenous administration. This ratio was not based on the empirically-derived regimens currently used for cytarabine and anthracyclines.

A "treatment cycle" is a specific protocol that specifies dosage times and amounts for CPX-351 and, if appropriate, an additional agent. For example, a treatment cycle may employ one or more daily administrations of CPX-351 on certain days with specified dosages, for example, on days 1 and 3, or 1, 3, and 5, or 1 and 8, or 1 and 15, or on days 1, 2 and 5, or 1, 5, and 8, or 1, 5 and 15 or 1, 8 and 15. The specific days may vary.

Patients populations, such as untreated AML patients or relapse/refractory AML patients may be treated with the disclosed protocols. Patients population treatable with the methods include patients that fit to receive intensive chemotherapy and patients that are unfit to receive intensive chemotherapy.

ISICT patients are critical populations to demonstrate benefit given the high unmet medical need. Population sizes are significant and yet the treatments available today still do not provide adequate improvements in overall survival. CPX-351 represents a promising new tool for improving efficacy while maintaining safety for these patients.

A number of factors are used to determine eligibility for ICT including, for example, physical performance, comorbid conditions and cognitive function (Pettit and Odenike; Front. Oncol. (2015) 5:280; which is incorporated herein by reference). The therapeutic aim for ISICT patients is to reduce disease burden, extend patient life, and improve their quality of life.

AML

Acute Myeloid Leukemia is a clonal expansion of undifferentiated myeloid precursors that causes an impairment of new blood cell generation. The median age of diagnosis 67 years. Clinical manifestations include fever, fatigue, bone pain, pallor, easy bruising. Diagnosis is based on having 2:20% myeloid blasts in the bone marrow. Disease characteristics including cytogenetic and molecular genetic findings are major prognostic factors. Patient characteristics (age, co-morbidities) also play a role in prognosis, since they influence the ability to undergo treatment. Currently, optimal disease treatment for fit patients is based on intensive chemotherapy, divided into induction and consolidation phases. Differential diagnosis includes other hematologic malignancies and MDS.

MDS

Myelodysplastic syndromes are a family of rare disorders in which the bone marrow fails to make enough healthy red blood cells, white blood cells or platelets. This is caused by bone marrow producing Jots of underdeveloped, or immature, cells that have an abnormal shape, size or look. These are called blast cells. Most experts agree that MDS is a form of blood and bone marrow cancer and can be difficult to diagnose.

CPX-351 Combination Therapy

In a phase 3 trial in older adults (aged 60-75 years) with newly diagnosed high-risk/secondary AML, CPX-351 significantly prolonged overall survival versus standard 7+3 cytarabine/daunorubicin (9.56 vs 5.95 months; hazard ratio=0.69; 1-sided P=0.003), and the safety profile of CPX-351 was generally consistent with the known profile of the 7+3 regimen (Lancet J E, et al. J Clin Oncol. 2018; 36(26):2684-2692; which is incorporated herein by reference).

Chemotherapy-induced thrombocytopenia is a common and serious complication that is associated with an increased risk of bleeding and is often accompanied by chemotherapy dose adjustments, which may compromise treatment outcomes. Platelet transfusions are a mainstay for treatment of chemotherapy-induced thrombocytopenia. Chemotherapy-induced neutropenia (CIN) is a serious adverse event that is associated with an increased risk of life-threatening infection and often leads to chemotherapy dose reductions and/or treatment delays, which may lead to poor treatment outcomes. Endogenous granulocyte colony-stimulating factor (GCSF) is the primary regulator of neutrophil production, and recombinant GCSF agents are commonly used to treat CIN.

Standard dose CPX-351 was approved by the FDA for the treatment of adults with two types of high-risk acute myeloid leukemia (AML): newly diagnosed therapy-related AML (t-AML) or AML with myelodysplasia-related changes (AML-MRC). CPX-351 showed a significant improvement in overall survival in these patients compared to the standard 7+3 therapy. Results from earlier clinical studies also showed favorable results for treatment of other leukemias or hematological disorders such as myelodysplastic syndromes (MDS) and certain lymphoblastic leukemias/lymphomas.

Standard dose CPX-351 as currently approved does not cover patients with AML considered ineligible for intensive chemotherapy (ICT), or some patients with MDS. The current approach to treating patients ineligible for ICT consists of lower intensity treatments (e.g. Low dose cytarabine (LDAC) or HMA alone or in various combinations with novel agents. Primary intent is to minimize toxicity while achieving acceptable response rate translating into improvement of Quality-of-Life, reduction of transfusion requirements and possibly extension of survival.

Lower intensity combinations can achieve significant response rates, in particular in vulnerable patient populations. Whereas response rates with LDAC or HMAs single agents are modest, significantly higher and more durable responses can be seen in combinations as recently demonstrated with lower intensity therapy plus Venetoclax (DiNardo et al., Blood (2015) 126:327; incorporated herein by reference.)

CPX-351 is biologically active in high-risk patient populations, including secondary AML with prior history of MDS and those patients with MDS related karyotype (see phase 3 study referenced herein). CPX-351 improved survival compared to the standard 7+3 therapy in patients with AML who progressed from MDS and who were previously untreated with HMA.

Focusing on AML patients with 20-29% blasts ("oligoblastic AML", in the past also referred to as "RAEBT", a subtype of advanced MDS), CPX-351 showed superior median overall survival of 12.5 months compared with 5.95 months with 7+3 including patients with prior HMA exposure. Thus there is therefore reason to believe that lower intensity CPX-351 could be a more effective backbone combination partner when compared to LDAC or HMA.

When treating AML patients not eligible for standard ICT, subjects for use with low-intensity treatment of CPX-351 should have histological confirmation of AML by World Health Organization (WHO) criteria.

Provided herein is a method to treat a hematologic proliferative disorder in a subject, which method comprises administering to said subject a pharmaceutical composition comprising a pharmaceutical composition comprising a fixed, 5:1 molar ratio of cytarabine and daunorubicin, i.e., CPX-351, wherein the cytarabine and daunorubicin are stably associated with one or more delivery vehicles, in a treatment cycle in combination with Venetoclax. Provided herein is a method to treat a hematologic proliferative disorder in a subject, which method comprises administering to said subject a pharmaceutical composition comprising CPX-351 that supplies daunorubicin and cytarabine in a treatment cycle in combination with Venetoclax.

Encapsulation in these delivery vehicles allows two or more agents to be delivered to the disease site in a coordinated fashion, thereby assuring that the agents will be present at the disease site at a non-antagonistic ratio. This result will be achieved whether the agents are co-encapsulated in delivery vehicles, or are separately encapsulated in delivery vehicles administered such that non-antagonistic ratios are maintained at the disease site. The pharmacokinetics (PK) of the composition are controlled by the delivery vehicles themselves such that coordinated delivery is achieved (provided that the PK of the delivery systems are comparable). In a specific embodiment, the pharmaceutical composition comprising a fixed, 5:1 molar ratio of cytarabine and daunorubicin is CPX-351, described in U.S. Pat. Nos. 7,238,367; 7,744,921; 7,850,990; 8,022,279; 8,092,828; 8,431,806; 8,518,437; 9,271,931; 10,028,912; and 10,166,184; all of which are incorporated herein by reference in their entireties for any purpose.

In one embodiment, said pharmaceutical composition comprising a fixed, 5:1 molar ratio of cytarabine and daunorubicin is administered once or twice a week. In one embodiment, said pharmaceutical composition comprising a fixed, 5:1 molar ratio of cytarabine and daunorubicin is administered continuously for up to 12 months, or up to 24 months.

In one embodiment, said pharmaceutical composition comprising a fixed, 5:1 molar ratio of cytarabine and daunorubicin is administered at a cytarabine dose of less than 32 $mg/m^2/day$ or less than 24 $mg/m^2/day$.

In some embodiments, CPX-351 is administered intravenously on days 1, 3, and 5 and venetoclax is administered orally on days 2-21 on a 28 day cycle. In some embodiments, CPX-351 is administered intravenously on days 1 and 3 and venetoclax is administered orally on days 2-21 on a 28 day cycle.

In some embodiments, the subject is eligible for standard intensive chemotherapy. In some embodiments, the subject eligible for standard intensive chemotherapy has never undergone a previous anti-cancer regimen. In some embodiments, the subject eligible for standard intensive chemotherapy has not previously received intensive chemotherapy. In some embodiments, the subject eligible for standard intensive chemotherapy has previously undergone at least one anti-cancer regimen. In certain embodiments, provided is a method to treat a hematologic proliferative disorder in a subject, said method comprising administering to said subject a low-intensity CPX-351 treatment regimen in combination with venetoclax.

In some embodiments, the subject is ineligible for standard intensive chemotherapy. In some embodiments, the subject ineligible for standard intensive chemotherapy has never undergone a previous anti-cancer regimen. In some embodiments, the subject ineligible for standard intensive chemotherapy has not previously received intensive chemotherapy. In some embodiments, the subject ineligible for standard intensive chemotherapy has previously undergone at least one anti-cancer regimen. In certain embodiments, provided is a method to treat a hematologic proliferative disorder in an ISICT subject, said method comprising administering to said subject a low-intensity CPX-351 treatment regimen in combination with venetoclax.

In one embodiment, a low-intensity treatment of CPX-351 comprises administering CPX-351 intravenously in 30 minutes to 3 hours. In specific embodiments, CPX-351 is administered intravenously in 90 minutes or less. In specific embodiments, CPX-351 is administered intravenously in about 90 minutes. In certain embodiments, CPX-351 is administered once or twice a week. In certain other embodiments, CPX-351 is administered at a cytarabine dose of less than 32 mg/m$^2$/day or less than 24 mg/m$^2$/day. Preferably, CPX-351 is administered at a cytarabine dose of less than 24 mg/m$^2$/day.

In one embodiment, provided is a method to treat a hematologic proliferative disorder in a subject, said method comprising administering to said subject a low-dose CPX-351 treatment, wherein said composition is administered prior to said subject receiving any chemotherapy.

In one embodiment, provided is a method to treat a hematologic proliferative disorder in an ISICT subject, said method comprising administering to said ISICT subject a low-dose CPX-351 treatment, wherein said composition is administered prior to said subject receiving any chemotherapy.

In another embodiment, treatment of said subjects ineligible for standard intensive chemotherapy is administered on an outpatient basis or as a home-based treatment.

In some embodiments, the subject is receiving a CYP3A inhibitor. In some embodiments, the subject is receiving a strong CYP3A inhibitor. In some embodiments, the subject is receiving a moderate CYP3A inhibitor. In some embodiments, the subject is not receiving either a strong or moderate CYP3A inhibitor. CYP3A inhibitors include, but are not limited to, oceprevir, cobicistat, danoprevir and ritonavir, elvitegravir and ritonavir, grapefruit juice, indinavir and ritonavir, itraconazole, ketoconazole, lopinavir, ritonavir, paritaprevir and ritonavir and (ombitasvir and/or dasabuvir), posaconazole, saquinavir and ritonavir, telaprevir, tipranavir and ritonavir, telithromycin, troleandomycin, voriconazole, clarithromycin, idelalisib, nefazodone, nelfinavir, prepitant, ciprofloxacin, conivaptan, crizotinib, cyclosporine, diltiazem, dronedarone, erythromycin, fluconazole, fluvoxamine, imatinib, tofisopam, verapamil, chlorzoxazone, cilostazol, cimetidine, clotrimazole, fosaprepitant, istradefylline, ivacaftor, lomitapide, ranitidine, ranolazine, and ticagrelor. Strong CYP3A inhibitors include, but are not limited to, CYP3A inhibitors include, but are not limited to, oceprevir, cobicistat, danoprevir and ritonavir, elvitegravir and ritonavir, grapefruit juice, indinavir and ritonavir, itraconazole, ketoconazole, lopinavir, ritonavir, paritaprevir and ritonavir and (ombitasvir and/or dasabuvir), posaconazole, saquinavir and ritonavir, telaprevir, tipranavir and ritonavir, telithromycin, troleandomycin, voriconazole, clarithromycin, idelalisib, nefazodone, and nelfinavir. Moderate CYP3A inhibitors include, but are not limited to, prepitant, ciprofloxacin, conivaptan, crizotinib, cyclosporine, diltiazem, dronedarone, erythromycin, fluconazole, fluvoxamine, imatinib, tofisopam, and verapamil. Weak CYP3A inhibitors include, but are not limited to, chlorzoxazone, cilostazol, cimetidine, clotrimazole, fosaprepitant, istradefylline, ivacaftor, lomitapide, ranitidine, ranolazine, and ticagrelor.

In some embodiments, the hematologic proliferative disorder is acute lymphocytic leukemia (ALL), acute myeloid leukemia (AML), chronic myelogenous leukemia (CML), chronic lymphocytic leukemia (CLL) or acute promyelocytic leukemia (APL), myelodysplastic syndrome (MDS) or myeloproliferative neoplasm (MPN). In some embodiments, the hematologic proliferative disorder is an advanced hematologic cancer. In some embodiments, the advanced hematologic cancer is acute lymphocytic leukemia (ALL), acute myeloid leukemia (AML) or acute promyelocytic leukemia (APL). In some embodiments, the advanced hematologic cancer is acute myeloid leukemia (AML). In other embodiments, the hematologic proliferative disorder is myelodysplastic syndrome (MDS) or myeloproliferative neoplasm (MPN). In other embodiments, the hematologic proliferative disorder is myelodysplastic syndrome (MDS).

EXAMPLES

The following examples are offered to illustrate but not to limit the invention.

Example 1—Population Pharmacokinetic-Pharmacodynamic (PK-PD) Modeling of 7+3 or CPX-351-Induced Thrombocytopenia The following CPX-351 studies were used for PK-PD Modeling:
Study 101
    Phase 1, open-label, dose-escalation study of CPX-351 in 48 adults with relapsed/refractory AML, ALL, or MDS
    CPX-351 Dosages: 3 to 134 units/m$^2$ (1 unit=1 mg of cytarabine and 0.44 mg of daunorubicin) via 90-minute intravenous (IV) infusion on Days 1, 3, and 5
    PK Data Collection: Intensive sampling on Days 1, 3, and 5
    PD Data Collection: Pre-dose; on Days 1, 2, 3, 4, 5, 7, 14, 21, 28, 35, 42, and 56; and at follow-up (30 days after study discontinuation) Study 206
    Phase 2, open-label study of CPX-351 in 26 adults with AML, ALL, or MDS
    CPX-351 dosages
    Induction: 100 units/m$^2$ (100 mg/m$^2$ cytarabine+44 mg/m$^2$ daunorubicin) via 90-minute IV infusion on Days 1, 3, and 5 (2nd induction: Days 1 and 3)
    Consolidation: 65 units/m$^2$ (65 mg/m$^2$ cytarabine+29 mg/m$^2$ daunorubicin) via 90-minute IV infusion on Days 1 and 3
    PK Data Collection: Intensive sampling on Days 1 and 5
    PD Data Collection: Pre-dose; on Days 1, 3, 5, 7, 10±2, and 14±2; and then weekly (±2 days) until whichever occurred last: (1) Day 42, (2) peripheral blood count recovery, or (3) removal from study
Study 301
    Phase 3, multicenter, randomized trial in older adults with newly diagnosed high-risk/secondary AML to assess CPX-351 (n=153) versus 7+3 (n=156)
    CPX-351 Dosages: Same as for Study 206
    PK Data Collection: Sparse sampling throughout first week
    PD Data Collection: Same as for Study 206
    Table 1 shows the population PK parameters for Cytarabine and Daunorubicin following CPX-351 administration.

TABLE 1

| | Initial Population PK Parameters for Cytarabine and Daunorubicin Following CPX-351 Administration | |
|---|---|---|
| Parameter | Population mean equation | Interindividual varability |
| | Cytarabine | |
| CL, L/h | $0.106 \cdot (BSA/1.95)^{1.03}$ | 0.404 (63.5% CV) |
| Vc, L | $5.12 \cdot (BSA/1.95)^{1.16} \cdot (DOSEMGC/195)^{0.111}$ | 0.0847 (29.1% CV) |
| CLd, L/h | $0.00646 \cdot (BSA/1.95)^{1}$ | 0.5 Fixed (70.7% CV) |
| Vp, L | $0.214 \cdot (BSA/1.95)^{1}$ | 0.5 Fixed (70.7% CV) |
| Residual variability | 0.151 (log error) | — |
| | Daunorubicin | |
| CL2, L/h | $0.145 \cdot (BSA/1.95)^{1.22} \cdot \exp(-0.176 \cdot FORM2)$ | 0.218 (46.7% CV) |
| Vc2, L | $4.34 \cdot (BSA/1.95)^{1.27} \cdot \exp(-0.216 \cdot FORM2)$ | 0.0564 (23.7% CV) |
| CLd2, L/h | $0.0258 \cdot (BSA/1.95)^{1}$ | 0.5 Fixed (70.7% CV) |
| Vp2, L | $0.523 \cdot (BSA/1.95)^{1} \cdot (DOSEMGD/86)^{0.701}$ | 0.5 Fixed (70.7% CV) |
| Residual variability | 0.154 (log error) | — |

PK, pharmacokinetic; CL, clearance; BSA, body surface area; CV, coefficient of variation; Ve, central volume of distribution; DOSEMGC, cytarabine dose in mg; CLd, distribution clearance; Vp, peripheral volume of distribution; FORM2, CPX-351 formulation (1 for frozen, 0 for lyophilized); DOSEMGD, daunorubicin dose in mg.

Population PK-PD analysis was conducted using NON-MEM version 7.3 via implementation of the first-order conditional estimation method with 11-E interaction. Previously developed population PK models for CPX-351 and non-liposomal cytarabine and daunorubicin were used to generate patient-specific cytarabine and daunorubicin concentration-time profiles (Qi W, et al. Blood. 2017; 130. Abstract 5064 incorporated herein by reference). For both cytarabine and daunorubicin, 2-compartment disposition models were used to describe drug PK following CPX-351 administration. In the population PK-PD model of chemotherapy-induced thrombocytopenia, data from Cycle 1 were excluded if patients had a platelet count<$50 \times 10^9$/L prior to the first treatment cycle; data from subsequent cycles were only included if the platelet count returned to $2:50 \times 10^9$/L prior to treatment.

Platelet count versus time data were described by a modified maturation PK-PD model proposed by Friberg et al (Friberg L E, et al. J Clin Oncol. 2002; 20(24):4713-4721; incorporated herein by reference). Inhibition of platelet proliferation by CPX-351 and/or "7+3" was driven by a sigmoidal maximum inhibition (Imax) function of the sum of the molar concentrations of cytarabine and daunorubicin. Interindividual and interoccasion variability were estimated for select structural PK-PD model parameters using exponential error models.

The effect of each platelet transfusion on platelet dynamics was incorporated as a bolus input of $35 \times 10^9$/L into the circulating platelet pool, as this was the expected rise in platelet counts immediately post-transfusion (Mccullough J. Semin Hematol. 2010; 47(3):235-242; incorporated herein by reference) (see FIGS. 1A-IG). Information regarding actual platelet dose administered was not standardized or always provided, so the typical value for platelet transfusion bioavailability was fixed at 1 and interindividual variability in platelet transfusion bioavailability was estimated to allow for interindividual variability in the expected increase in platelet count following a platelet transfusion.

A graphical screening procedure was conducted to examine the relationship between patient covariates and key PK-PD model parameters, followed by stepwise forward selection ($\alpha=0.01$) and backward elimination ($\alpha=0.001$) to evaluate covariate effects. Baseline Patient Demographics were: Weight, height, age, body mass index, body surface area, sex, race, and ethnicity. Baseline Clinical Laboratory Measures were: Albumin, alkaline phosphatase, alanine aminotransferase, aspartate aminotransferase, total bilirubin, white blood cell count, absolute neutrophil count, platelet count, and creatinine clearance. Disease-related Indices were: Cancer type and Eastern Cooperative Oncology Group performance status.

An R Shiny application was developed in conjunction with the mrgsolve package (Metrum Research Group) so that the population PK-PD model could be used to simulate neutrophil or platelet dynamics following administration of various CPX-351 and "7+3" dosing regimens (including as administered in Study 301) with or without intermittent platelet transfusions. Simulations were conducted in 200 patients with characteristics similar to the trial population to evaluate the temporal events of myelosuppression in the absence of platelet transfusion or GCSF administration (see below).

Relevant patient demographics were generated with distributions that were comparable to those in the analysis dataset. Results are shown in Tables 2 and 3 below.

TABLE 2

| | Demographic Data for PK/PD Modeling | | | |
|---|---|---|---|---|
| | Platelet model | | Neutrophil model | |
| Variable | CPX-351 (n = 137) | 7 + 3 (n = 85) | CPX-351 (n = 129) | 7 + 3 (n = 79) |
| Age, y | | | | |
| Mean (SD) | 66.1 (8.88) | 67.8 (4.27) | 66.1 (9.1) | 67.5 (4.26) |
| Median (range) | 68 (23-80) | 68 (60-75) | 67 (23-81) | 68 (60-75) |

TABLE 2-continued

Demographic Data for PK/PD Modeling

| | Platelet model | | Neutrophil model | |
|---|---|---|---|---|
| Variable | CPX-351 (n = 137) | 7 + 3 (n = 85) | CPX-351 (n = 129) | 7 + 3 (n = 79) |
| Weight, kg | | | | |
| Mean (SD) | 82.4 (18.6) | 82.8 (16.8) | 82.4 (20.4) | 83.8 (16.8) |
| Median (range) | 82 (42-156) | 83 (50-136) | 78.7 (39.5-156) | 83 (54-136) |
| Height, cm | | | | |
| Mean (SD) | 170 (10.3) | 169 (16.8) | 170 (10.7) | 170 (8.84) |
| Median (range) | 170 (149-198) | 168 (152-189) | 170 (149-198) | 170 (152-186) |
| BSA, m$^2$ | | | | |
| Mean (SD) | 1.97 (0.262) | 1.97 (0.235) | 1.96 (0.28) | 1.98 (0.226) |
| Median (range) | 1.95 (1.3-2.8) | 1.96 (1.49-2.55) | 1.94 (1.30-2.80) | 1.96 (1.56-2.55) |
| BMI, kg/m$^2$ | | | | |
| Mean (SD) | 28.2 (5.04) | 28.8 (5.13) | 28.2 (5.48) | 28.8 (5.17) |
| Median (range) | 27.2 (18.4-48.3) | 28.7 (19.5-45.4) | 27.4 (17.1-48.3) | 28.3 (20.2-45.4) |
| CLcr, mL/min/1.73 m$^2$ | | | | |
| Mean (SD) | 78.9 (26.8) | 77.5 (22.7) | 78.5 (27.7) | 74.3 (22.7) |
| Median (range) | 74.2 (34.1-176) | 78.1 (30.1-157) | 73.4 (36.1-176) | 73.5 (30.1-163) |
| Total bilirubin, mg/dL | | | | |
| Mean (SD) | 0.64 (0.371) | 0.644 (0.400) | 0.694 (0.468) | 0.664 (0.462) |
| Median (range) | 0.53 (0.12-2.11) | 0.53 (0.18-2.81) | 0.53 (0.12-2.92) | 0.53 (0.12-2.98) |
| ALT, U/L | | | | |
| Mean (SD) | 31.0 (27.3) | 29.5 (21.3) | 28.0 (20.2) | 32.2 (23.5) |
| Median (range) | 21 (9-154) | 23 (9-154) | 23 (5-154) | 24 (9-154) |
| AST, U/L | | | | |
| Mean (SD) | 24.9 (12.7) | 25.8 (15.2) | 26.4 (12.9) | 27.9(15.8) |
| Median (range) | 22 (5-81) | 20 (9-96) | 24 (5-81) | 23 (11-83) |
| ALP, U/L | | | | |
| Mean (SD) | 75.5 (31.8) | 75.9 (34.4) | 87.6 (47.1) | 82.9 (50.4) |
| Median (range) | 68 (21-212) | 68 (32-202) | 77 (32-348) | 69 (32-398) |
| Albumin, g/dL | | | | |
| Mean (SD) | 3.57 (0.546) | 3.48 (0.592) | 3.50 (0.584) | 3.40 (0.584) |
| Median (range) | 3.6 (1.3-4.8) | 3.5 (1.8-4.5) | 3.6 (1.3-4.6) | 3.4 (2.0-4.5) |
| Platelet count 10$^9$/L | | | | |
| Mean (SD) | 85.1 (66.7) | 101 (107) | 67.1 (61.0) | 72.1 (124) |
| Median (range) | 63 (2-289) | 77 (11-836) | 43 (2-289) | 37 (5-836) |
| WBC, 10$^9$/L | | | | |
| Mean (SD) | 12.8 (32.1) | 9.61 (15.5) | 18.5 (35.3) | 18.5 (26.5) |
| Median (range) | 3.4 (0.24-323) | 2.9 (0.48-76.7) | 6.6 (0.9-323) | 7.1 (0.5-170) |
| ANC, 10$^9$/L | | | | |
| Mean (SD) | 2.56 (5.19) | 2.02 (3.61) | 4.42 (7.57) | 4.59 (9.87) |
| Median (range) | 0.76 (0-40.1) | 0.585 (0.03-24.2) | 1.98 (0-9.4) | 2.20 (0.06-83.1) |

PK, pharmacokinetic; PD, pharmacodynamic; SD, standard deviation; BSA, body surface area; BMI, body mass index; CLcr, creatinine clearance; ALT, alanine transaminase; AST, aspartate transaminase; ALP, alkaline phosphatase; WBC, white blood cell count; ANC, absolute neutrophil count.

TABLE 3

Demographic and Disease Status

| | | Platelet model | | Neutrophil model | |
|---|---|---|---|---|---|
| Category | Variable | CPX-351 n (%) | 7 + 3 n (%) | CPX-351 n (%) | 7 + 3 n (%) |
| Received ≥1 platelet | No | 2 (1.5) | 2 (2.4) | 86 (66.7) | 46 (58.2) |
| transfusion/GCSF | Yes | 135 (98.5) | 83 (97.6) | 43 (33.3) | 33 (41.8) |
| Sex | Male | 82 (59.9) | 49 (57.6) | 79 (61.2) | 48 (60.8) |
| | Female | 55 (40.1) | 36 (42.4) | 50 (38.8) | 31 (39.2) |
| Race | Caucasian | 115 (83.9) | 74 (87.1) | 110 (85.3) | 70 (88.6) |
| | Black | 8 (5.8) | 4 (4.7) | 6 (4.7) | 5 (6.3) |

TABLE 3-continued

| Demographic and Disease Status | | | | | |
| --- | --- | --- | --- | --- | --- |
| | | Platelet model | | Neutrophil model | |
| Category | Variable | CPX-351 n (%) | 7 + 3 n (%) | CPX-351 n (%) | 7 + 3 n (%) |
| | Asian | 8 (5.8) | 2 (2.4) | 4 (3.1) | 1 (1.3) |
| | Other/missing | 6 (4.4) | 5 (5.9) | 9 (7.0) | 3 (3.8) |
| ECOG performance status | 0 | 47 (34.3) | 29 (34.1) | 39 (30.2) | 23 (29.1) |
| | 1 | 78 (56.9) | 45 (52.9) | 76 (58.9) | 44 (55.7) |
| | 2 | 12 (8.8) | 11 (12.9) | 14 (10.9) | 12 (15.2) |
| Cancer type | ALL | 3 (2.2) | 0 (0) | 3 (2.33) | 0 (0) |
| | AML | 133 (97.1) | 85 (100) | 126 (97.7) | 79 (100) |
| | MDS | 1 (0.7) | 0 (0) | 0 (0) | 0 (0) |
| Remission status | CR | 62 (45.3) | 37 (43.5) | 56 (43.4) | 28 (35.4) |
| | CRi | 16 (11.7) | 6 (7.1) | 11 (8.5) | 4 (5.1) |
| | None | 59 (43.1) | 42 (49.4) | 62 (48.1) | 47 (59.5) |

GCSF, granulocyte colony stimulating factor; ECOG, Eastern Cooperative Oncology Group; ALL, acute lymphocytic leukemia; AML, acute myeloid leukemia; MDS, myelodysplastic syndrome; CR, complete remission; CRi, complete remission with incomplete neutrophil or platelet recovery. NB: for patients who were thrombocytopenia (platelet count $<50 \times 10^9$/L) prior to the first treatment cycle, data from Cycle 1 were excluded from analysis, and data from subsequent cycles were only included if the platelet count returned to 2:50 $\times 10^9$/L prior to treatment. However, for the purposes of covariate evaluation, the baseline platelet count from Cycle 1 was used, even if the value was $<50 \times 10^9$/L.

The early analysis dataset consisted of 2,023 platelet counts from 137 patients. Most patients (n=135; 98.5%) received 1 platelet transfusion during the study. The mean (standard deviation) number of platelet transfusions per person was 12 (9). The model fit improved significantly (P<0.00001) when bolus inputs to circulating platelets were incorporated to account for platelet transfusions. No potential covariates met criteria for inclusion.

TABLE 4

| Model Fitted PD Parameters for Platelets | | | | |
| --- | --- | --- | --- | --- |
| | CPX-351 | | 7 + 3 | |
| Parameter | Estimate | % SEM | Estimate | % SEM |
| Circa, $10^9$/L | 98.1 | 4.68 | 98.1 | 6.28 |
| MTT, h | 91.2 | 0.72 | 120 | 3.05 |
| $I_{max}$ | 0.316 | 0.29 | 1 | Fixed |
| $IC_{50}$ at weight of 83.4 kg, μM | 0.324 | 50.9 | 0.0982 | 5.6 |
| $IC_{50}$-weight power | — | — | 0.641 | 40.7 |
| $\gamma$ | 1.29 | 3.96 | 3.68 | 4.24 |
| $\gamma_T$ | 0.178 | 1.34 | 0.153 | 7.12 |

PD, pharmacodynamic; SEM, standard error of the mean; Circa, baseline circulating platelet count; MTT, mean transit time (4/$k_{tr}$); $I_{max}$, maximum inhibition of platelet proliferation; $IC_{50}$, composite concentration (cytarabine + daunorubicin) at which inhibition is 50% of $I_{max}$; $\gamma$, Hill coefficient for sigmoidal $I_{max}$ function; $\gamma_T$, feedback function exponent.

The model successfully captured observed data for CPX-351 and 7+3, with good precision on parameter estimates. In fact, most parameters in the final PK-PD model were estimated with excellent precision (<35% standard error of the mean [SEM]).

No covariates affecting the PD parameters of CPX-351 were identified, but body weight was identified as a covariate affecting the $IC_{50}$ of 7+3. The population mean for baseline circulating platelet numbers (Circ0) was similar for CPX-351 and 7+3, while the population mean for mean transit time (MTT) was slightly shorter for CPX-351. 7+3 was more potent than CPX-351, albeit the plasma concentrations of cytarabine and daunorubicin with CPX-351 were far greater than with 7+3.

The median time to observe the first platelet count<0.5× 109/L was 6.4 days after CPX-351 treatment and 5.8 days after 7+3, while the median time to an observed platelet count<20×109/L was 10.8 days and 8.9 days, respectively. The median duration with platelet counts<20×109/L was longer with CPX-351 (18 days) versus 7+3 (8 days), and the median duration of platelet counts platelet count<50×109/L was 22 days and 15 days, respectively. These results are summarized in Table 5 below.

TABLE 5

| Model-simulated Platelet Parameters After CPX-351 or 7 + 3 Treatment | | |
| --- | --- | --- |
| | CPX-351 | 7 + 3 |
| Mean (SD) nadir, $10^9$/L | 15.1 (13.5) | 9.05 (10.3) |
| Median nadir, $10^9$/L | 11.3 | 4.7 |
| Median time to nadir, h | 350 | 326 |
| Median time to 50 × $10^9$/L, h | 154 | 139 |
| Median duration <50 × $10^9$/L, h | 533 | 356 |
| Median time to 20 × $10^9$/L, h | 258 | 213 |
| Median duration <20 × $10^9$/L, h | 426 | 203 |

Figure 2A:
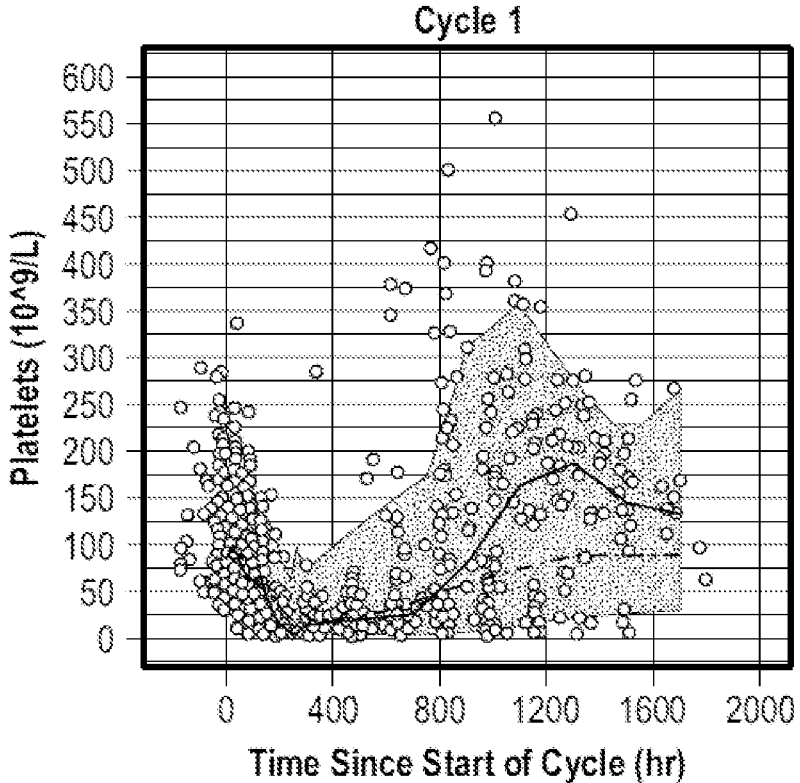
FIGS. 2A-2C show the Visual Predictive Check Stratified by Treatment Cycle for the Final Population PK-PD Model.
Figure 2A:
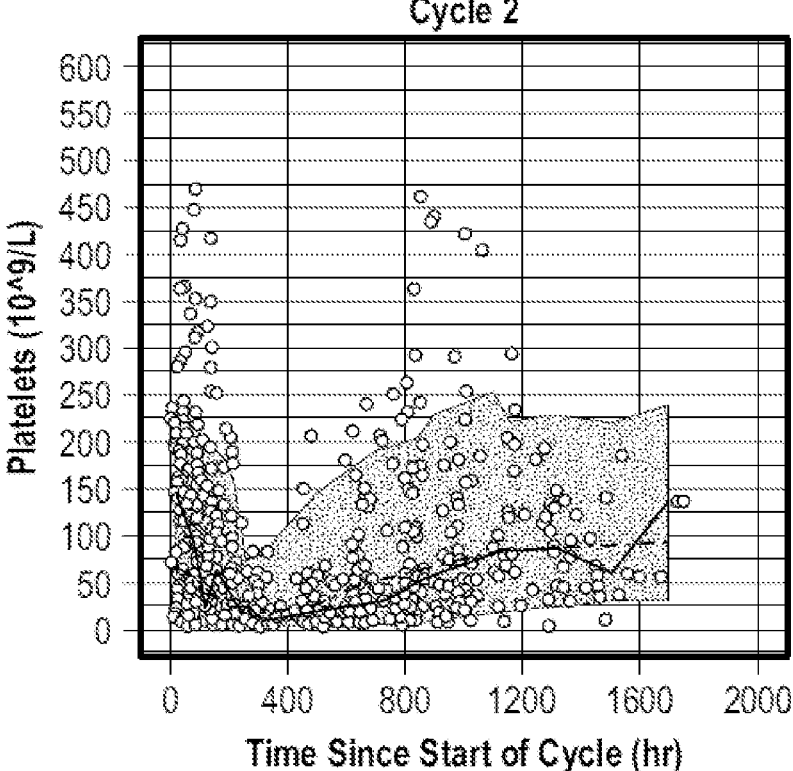
Figure 2B:
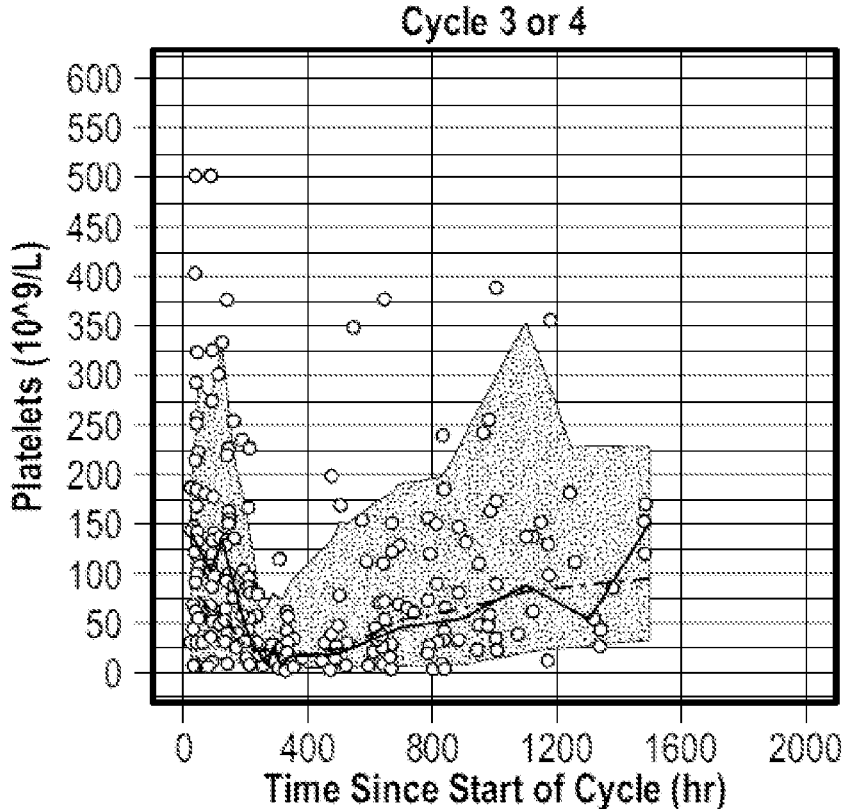
Figure 2C:
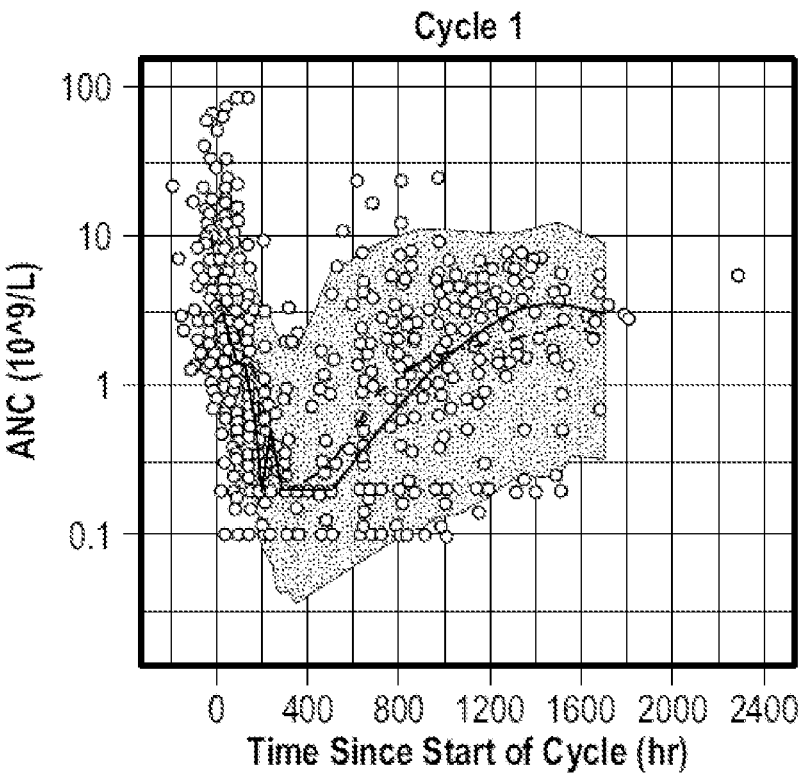
Figure 2C:
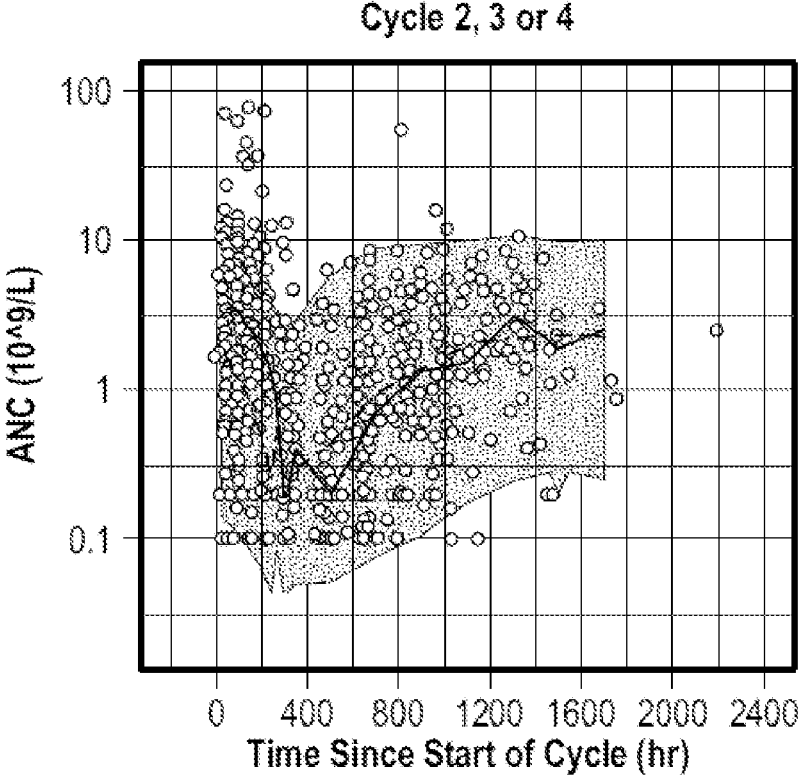
Figure 3A:
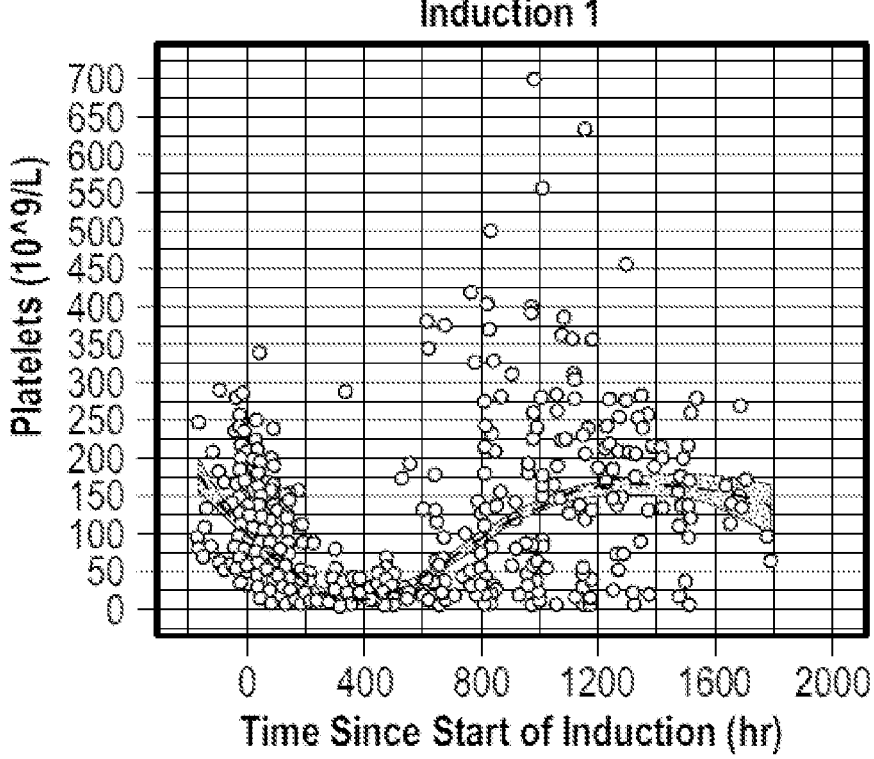
FIG. 3A-3B show Platelet Count vs. Time During CPX-351 Treatment.
Figure 3B:
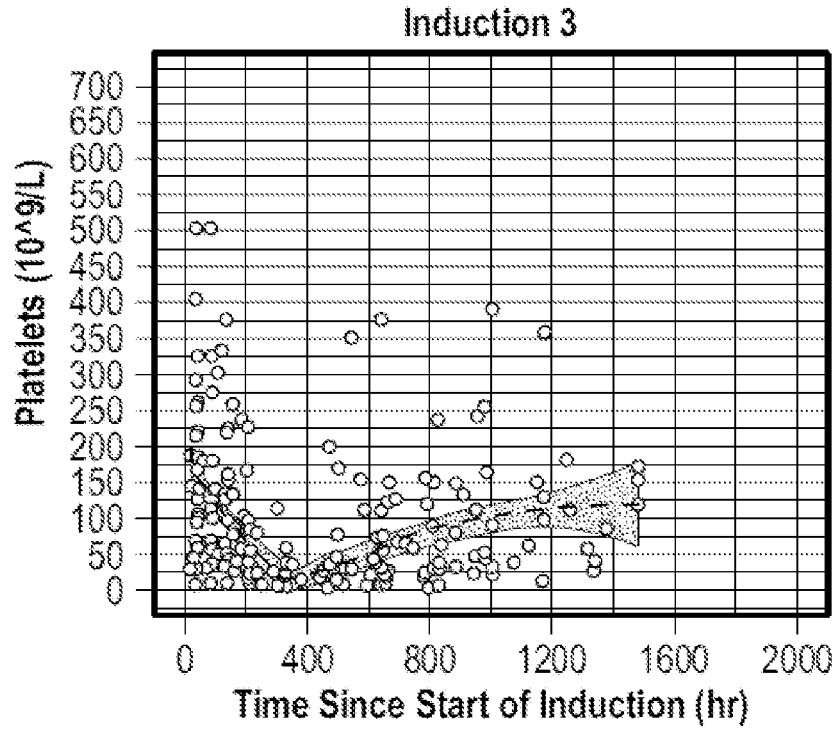
Figure 3B:
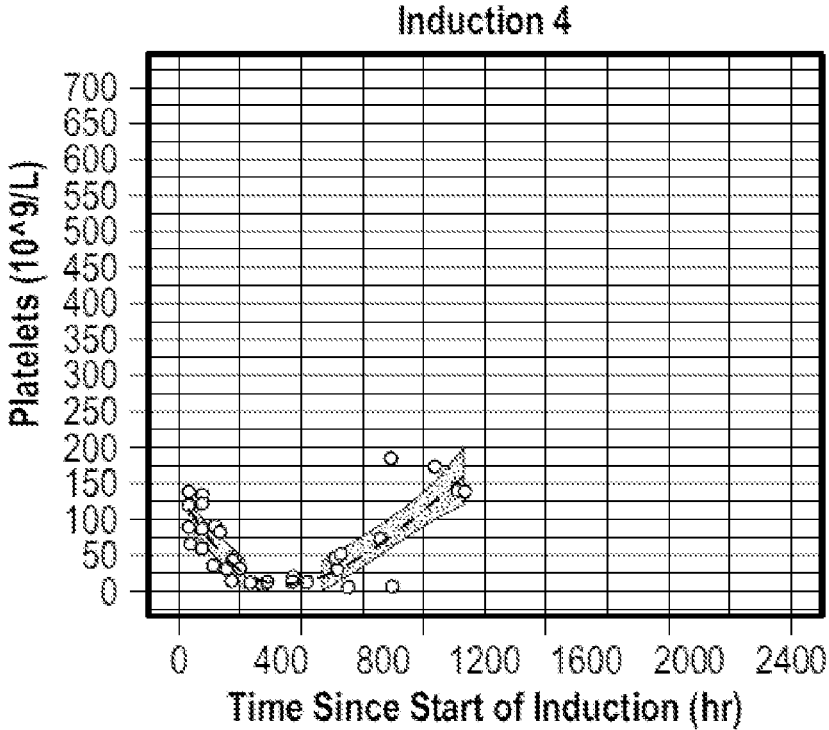
Figure 3C:
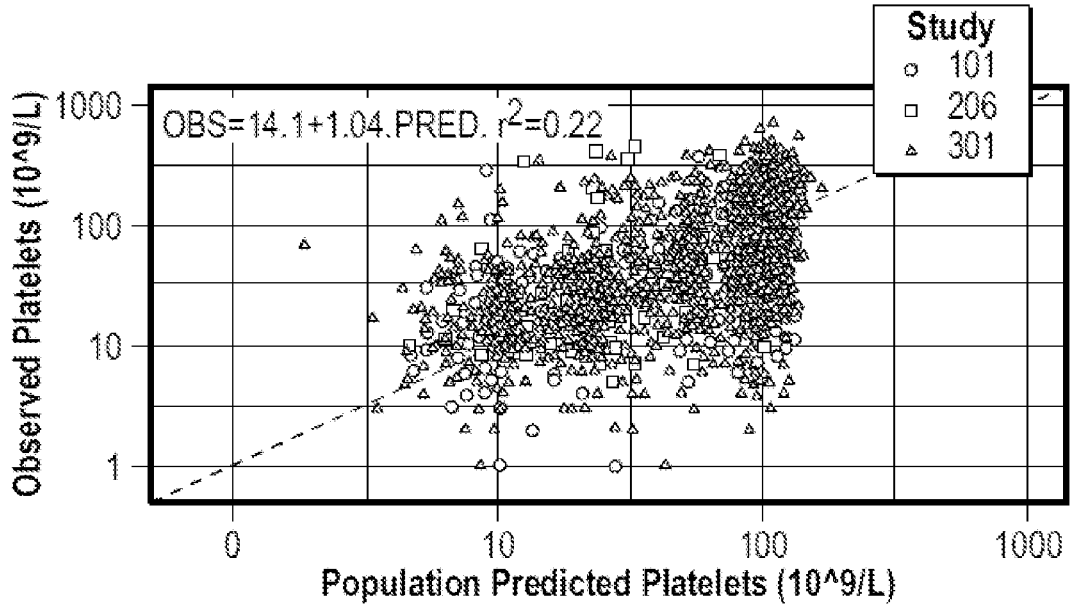
FIGS. 3C-3H show the GOP (goodness-of-fit) Plots: Final CPX-351 PK-PD Model for Platelets.
Figure 3C:
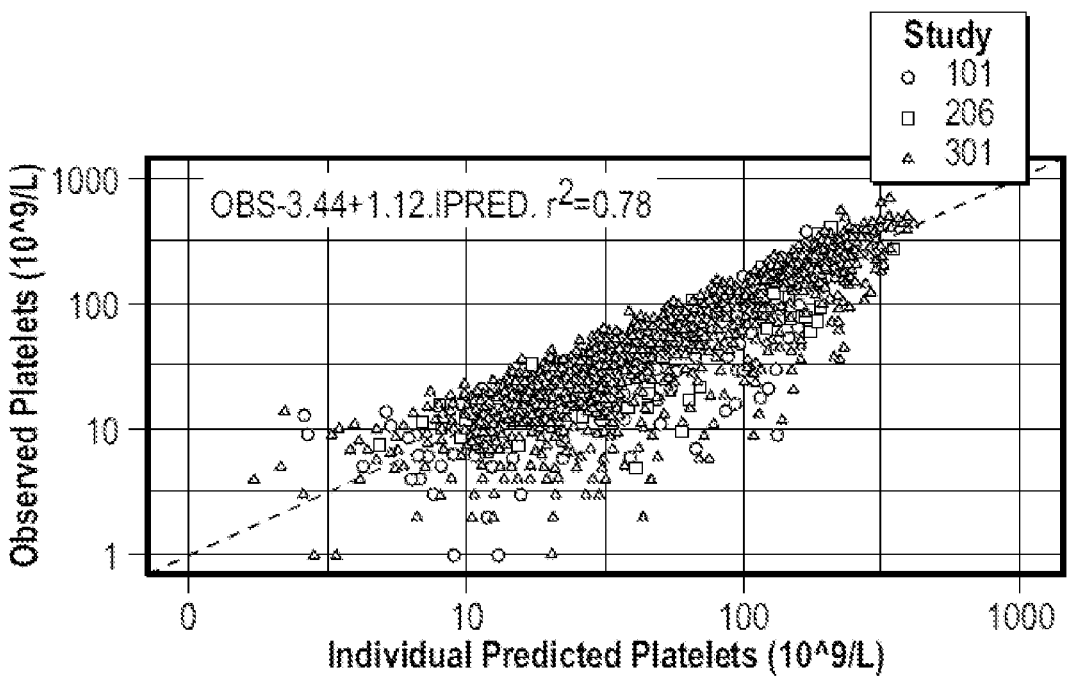
Figure 3D:
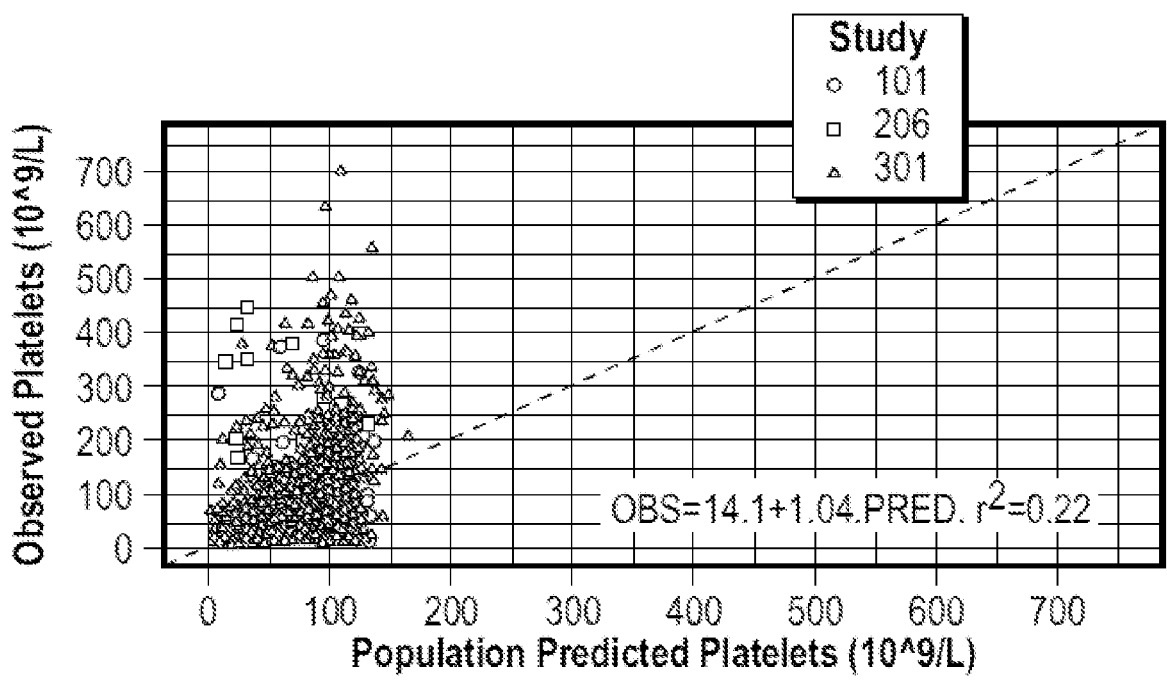
Figure 3D:
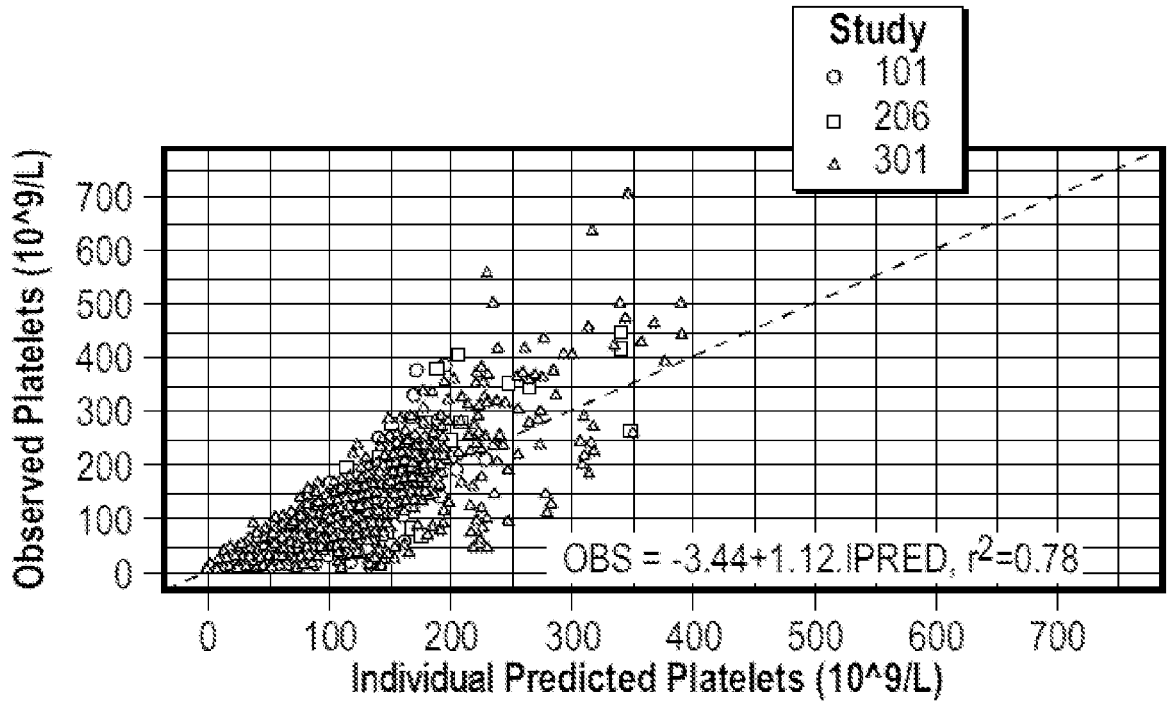
Figure 3E:
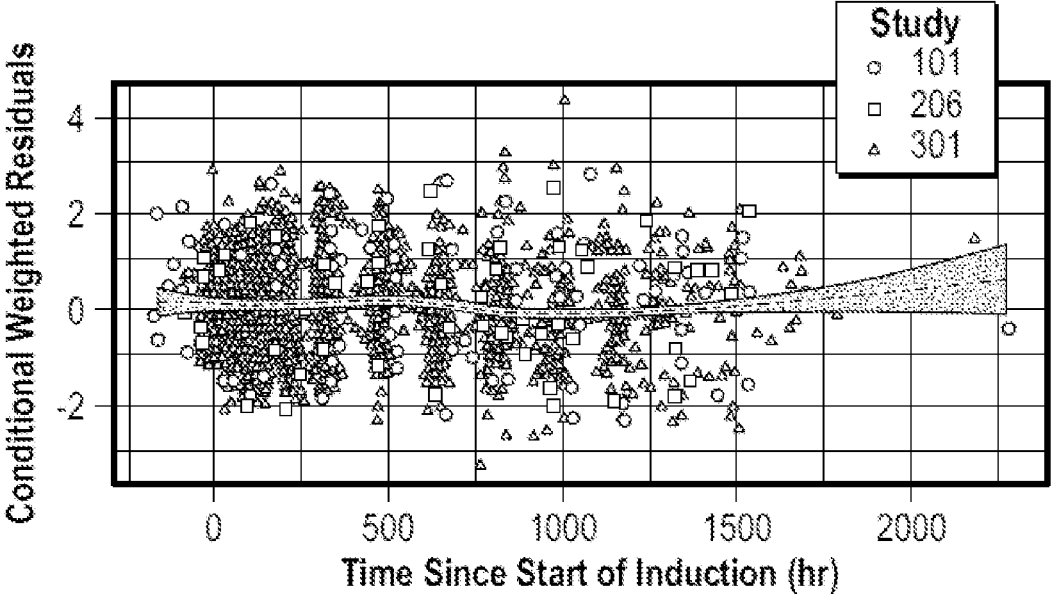
Figure 3E:
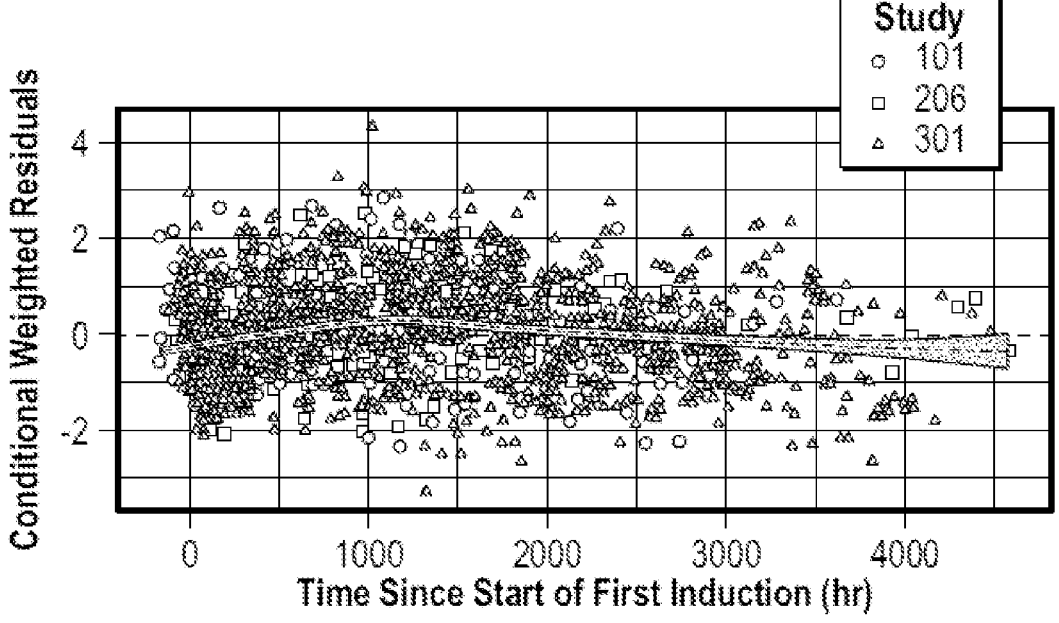
Figure 3F:
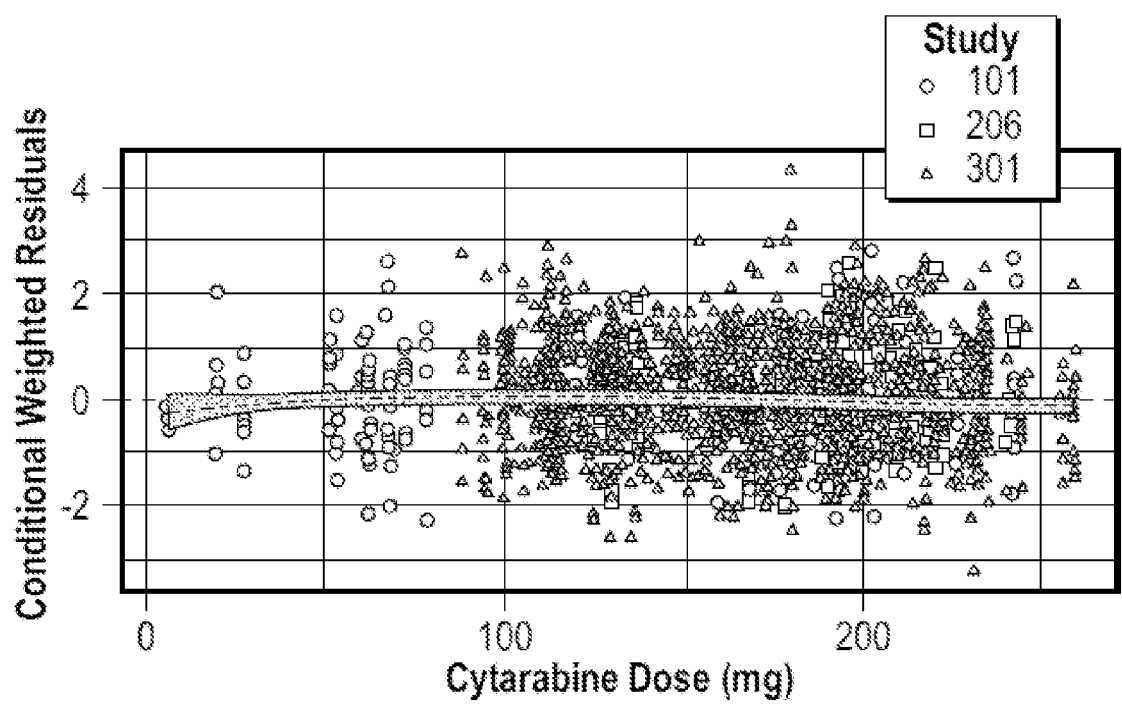
Figure 3F:
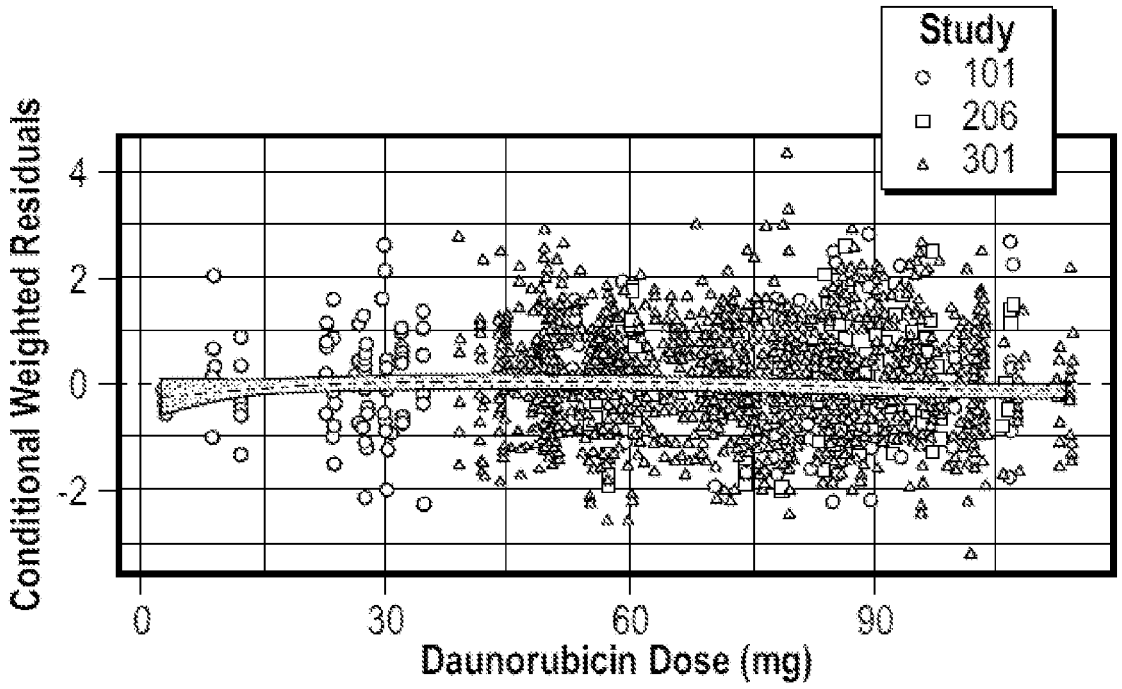
Figure 3G:
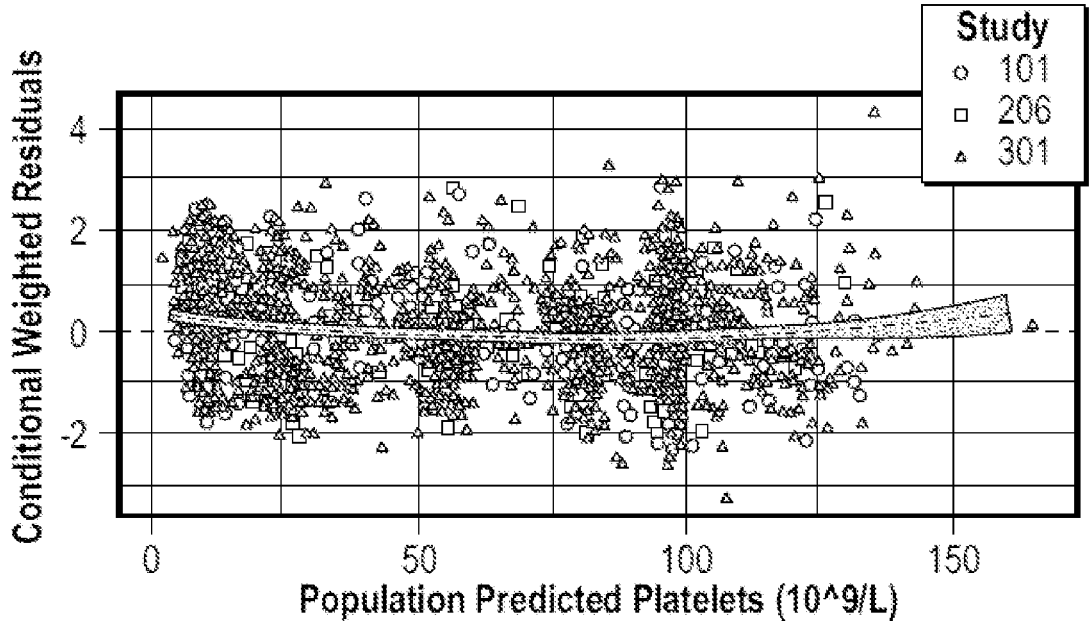
Figure 3G:
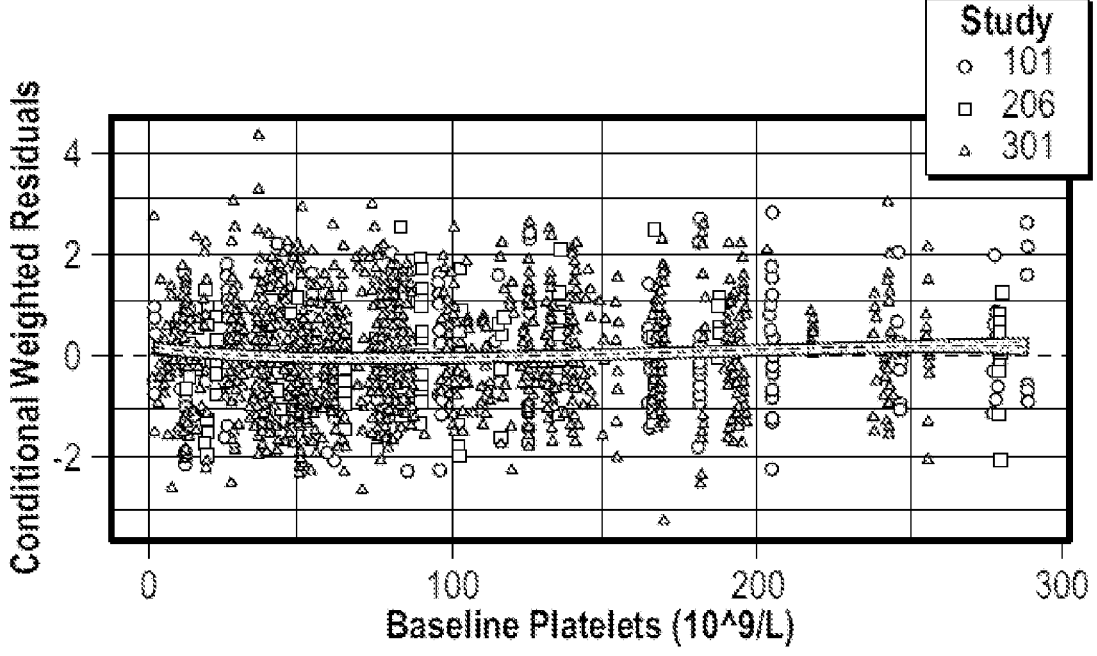
Figure 3H:
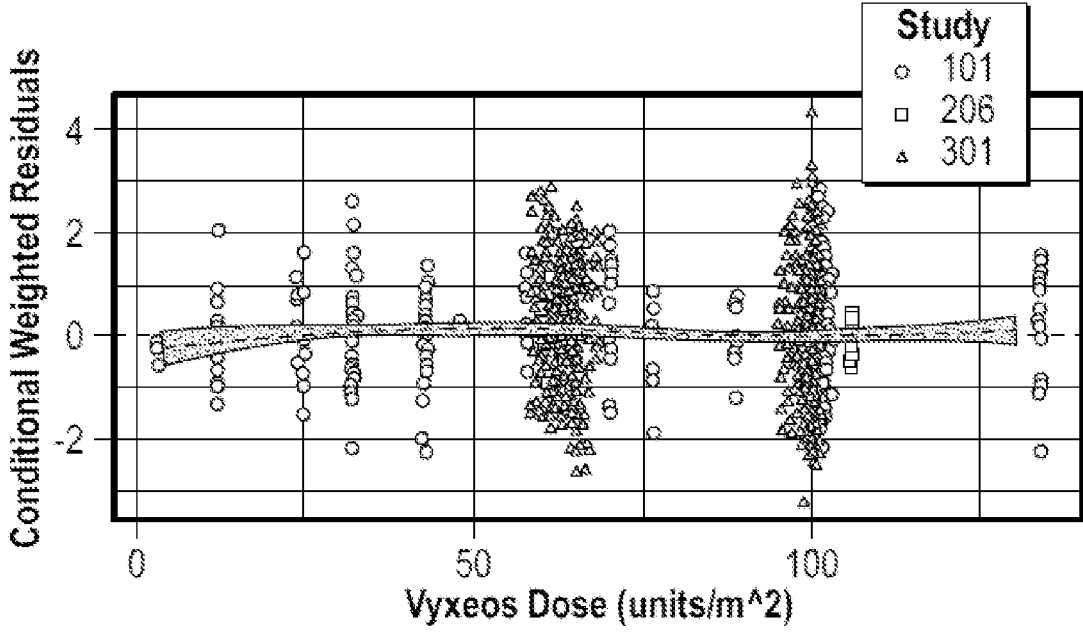
Figure 3H:
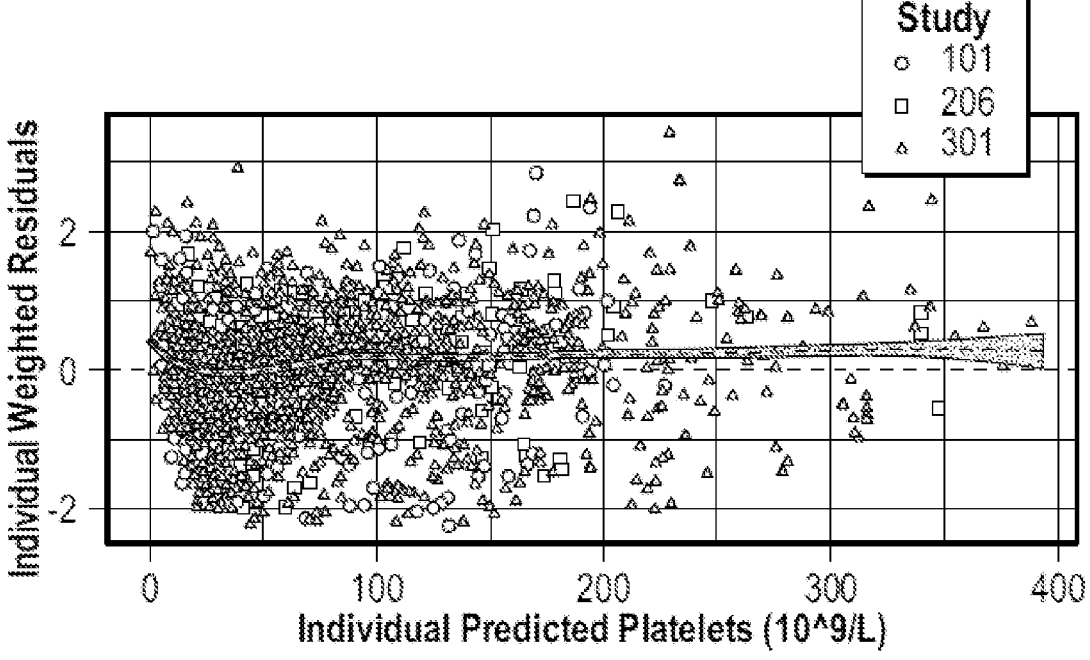
Figure 4A:
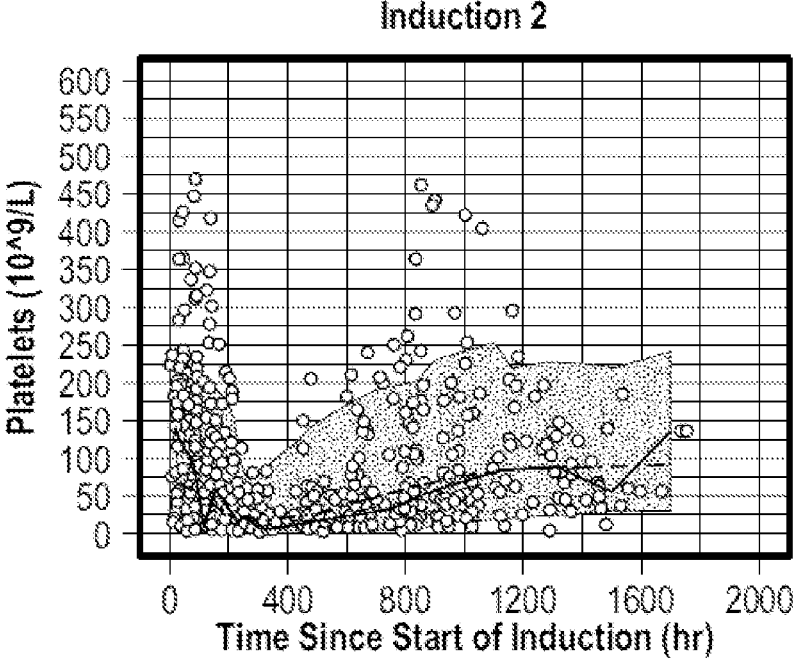
FIGS. 4A-4B show the VPC (Visual Predictive Check): Final CPX-351 PK-PD Model for Platelets.
Figure 4B:
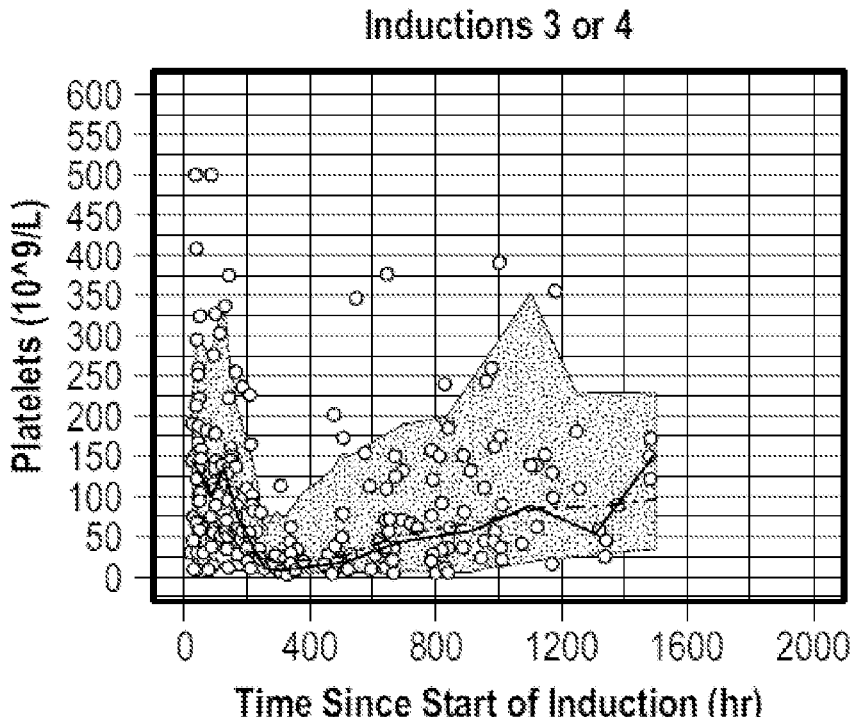
Figure 5A:
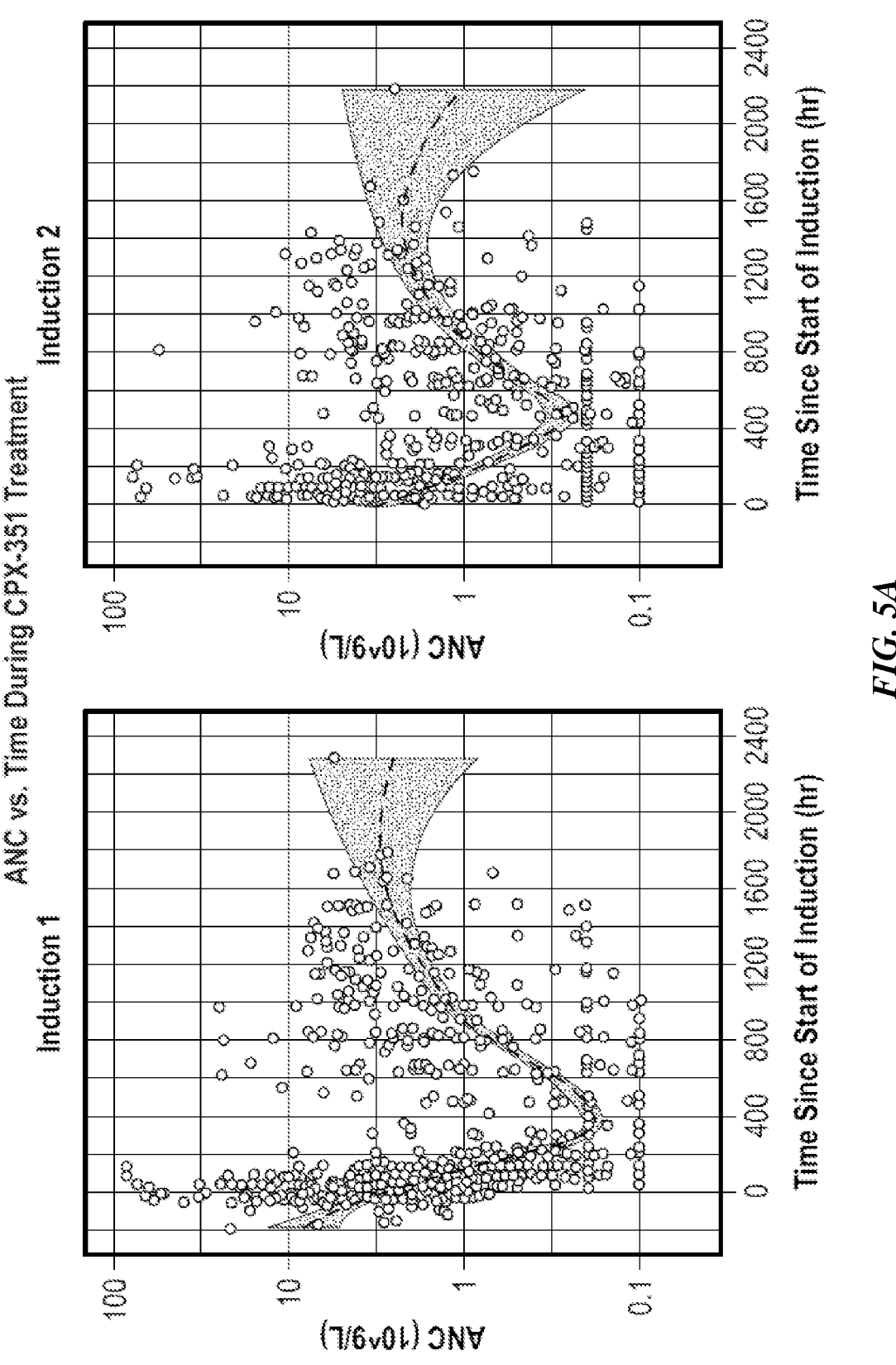
FIGS. 5A-5B show the ANC vs. Time During CPX-351 Treatment.
Figure 5B:
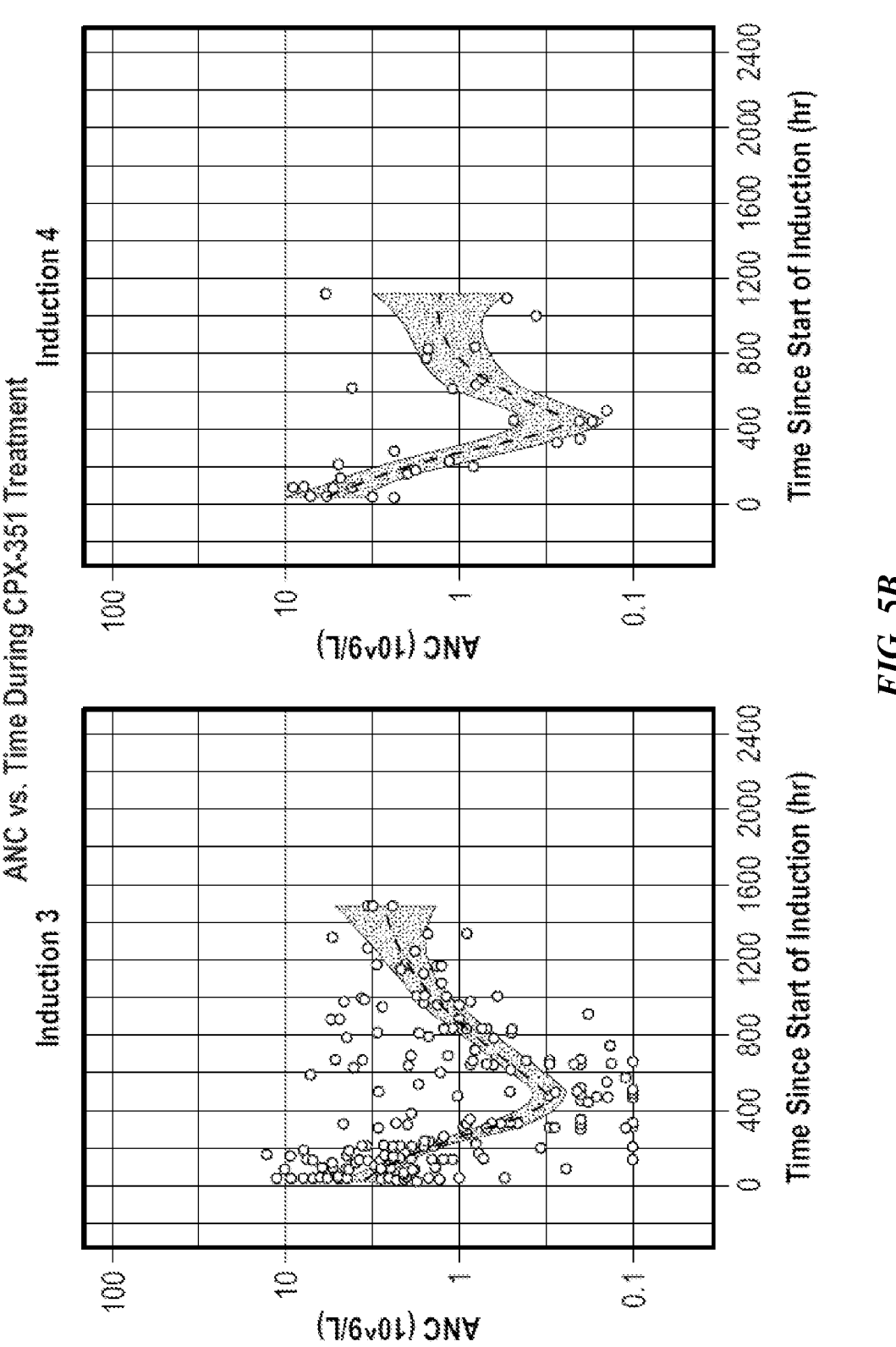
Figure 6A:
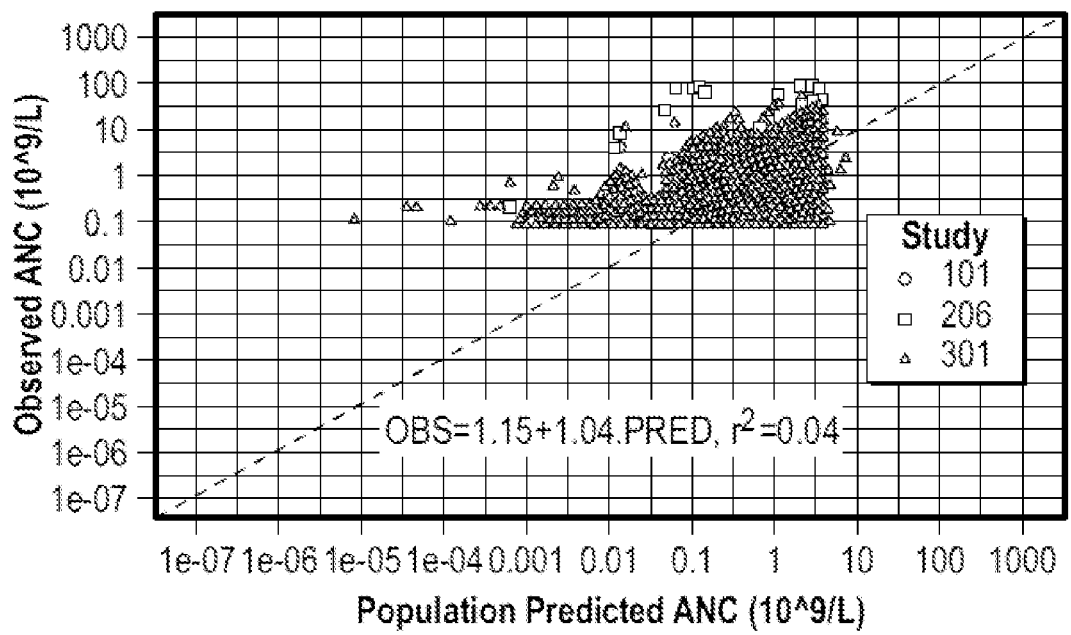
FIGS. 6A-6F show the GOP (goodness-of-fit) Plots: Base CPX-351 PK-PD Model for Neutrophils.
Figure 6A:
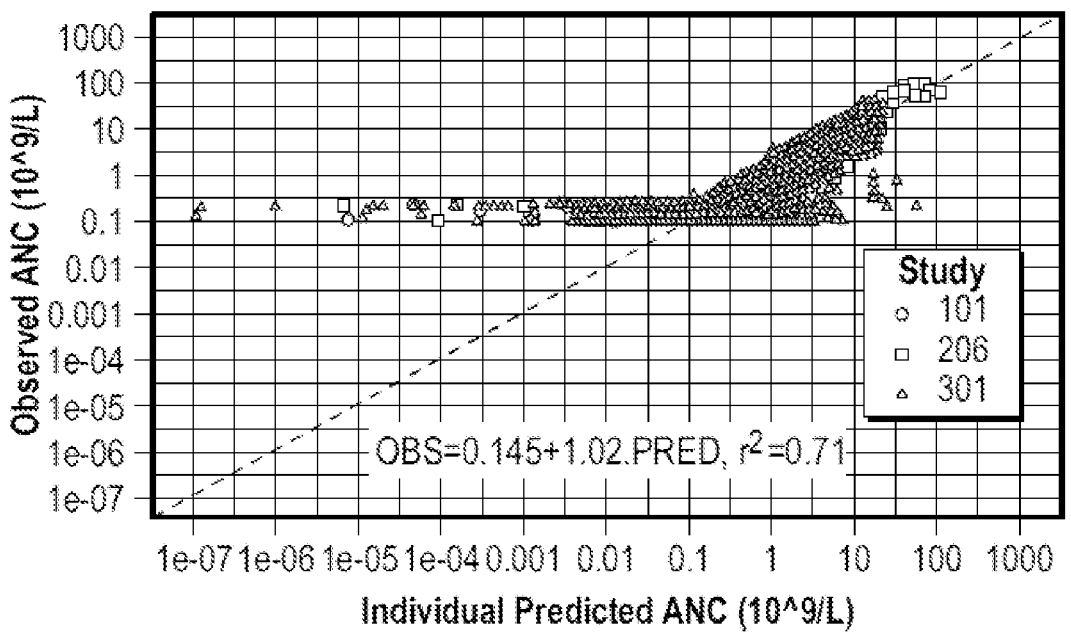
Figure 6B:
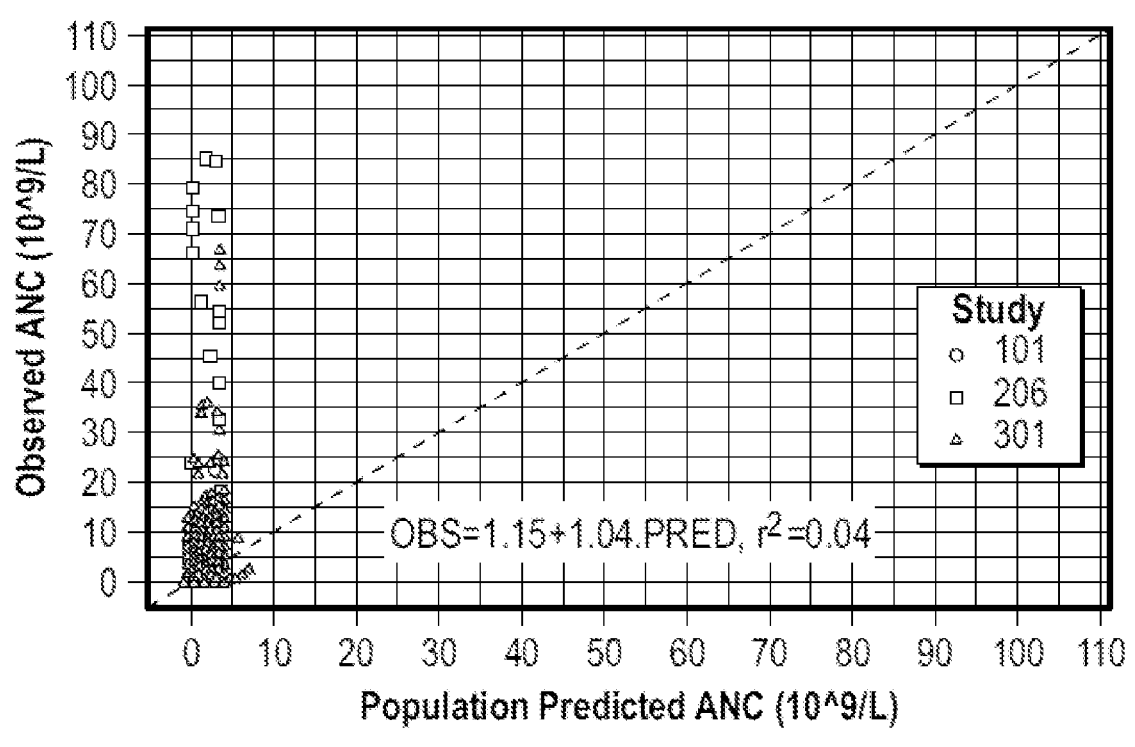
Figure 6B:
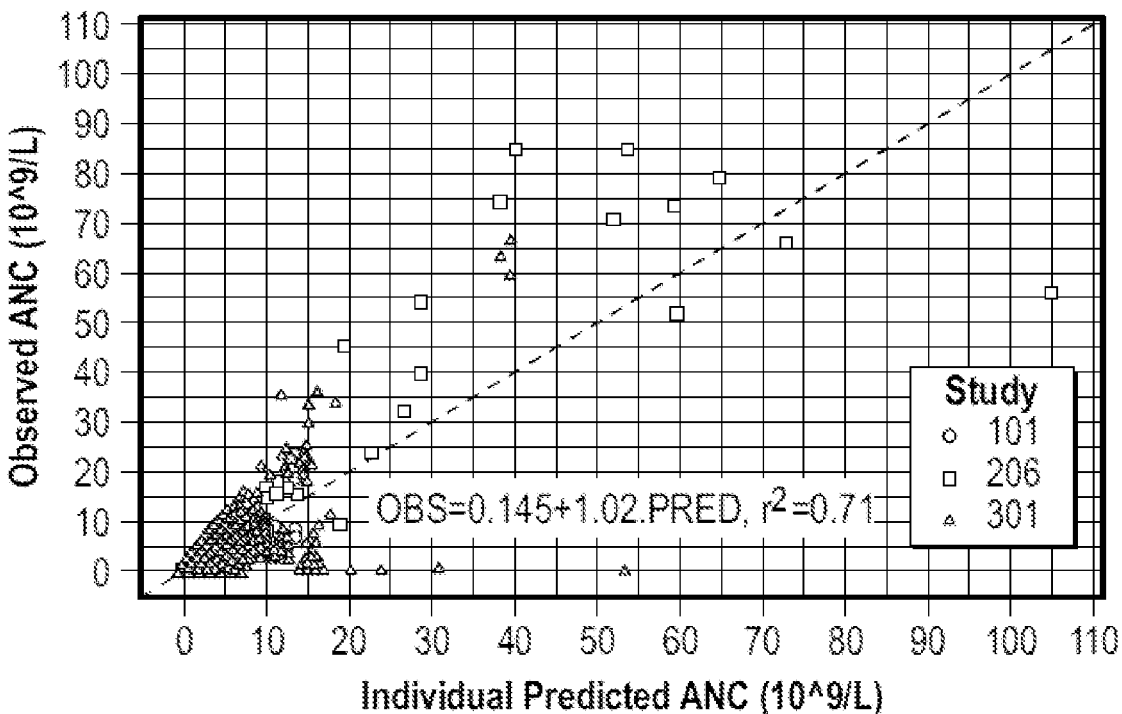
Figure 6C:
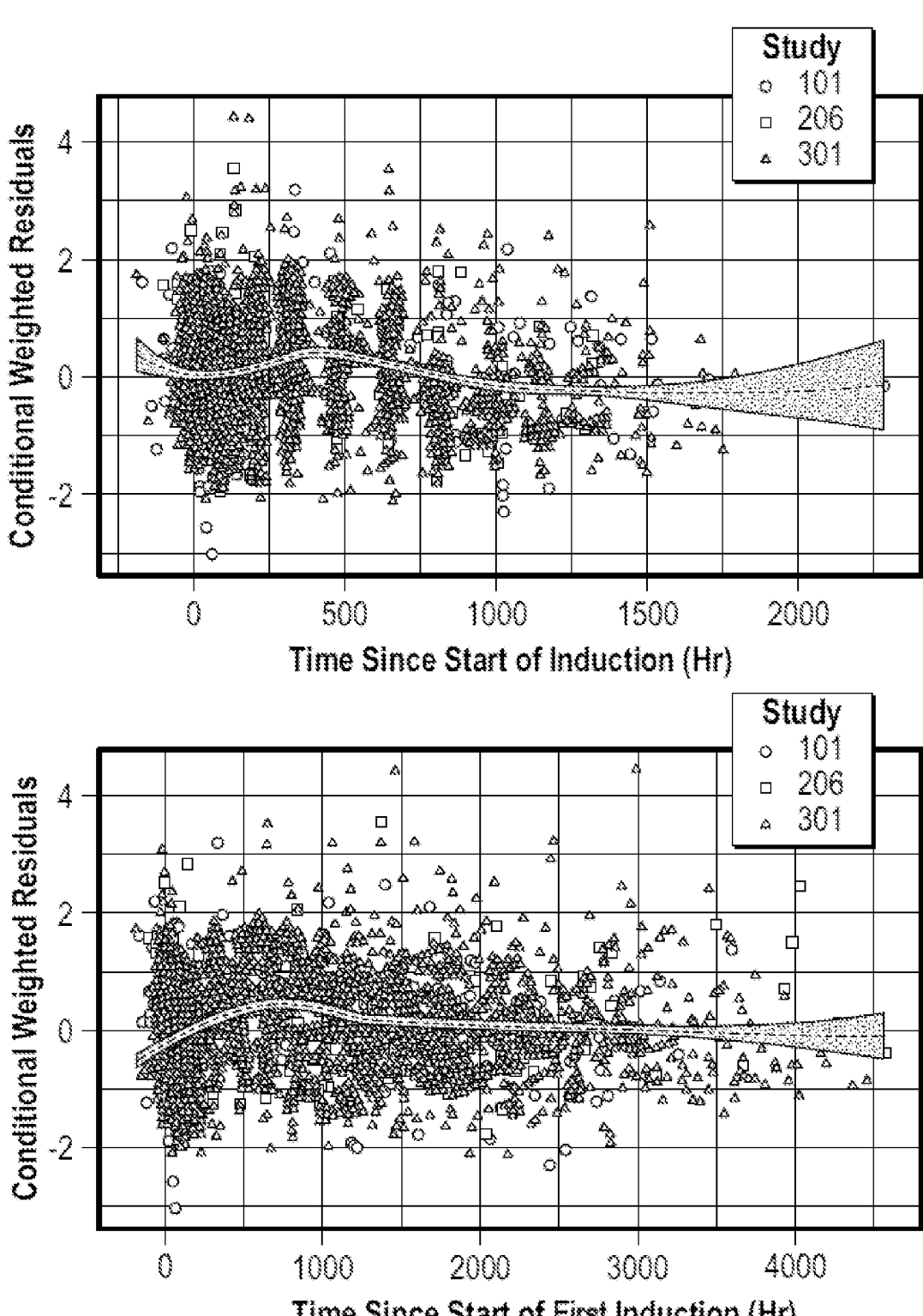
Figure 6D:
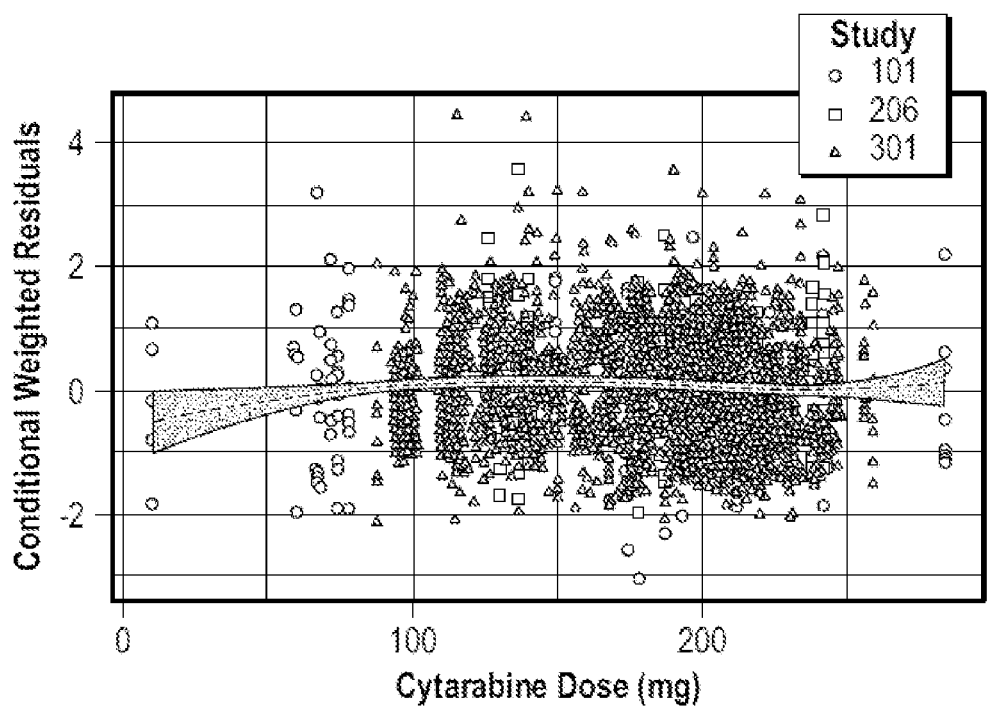
Figure 6D:
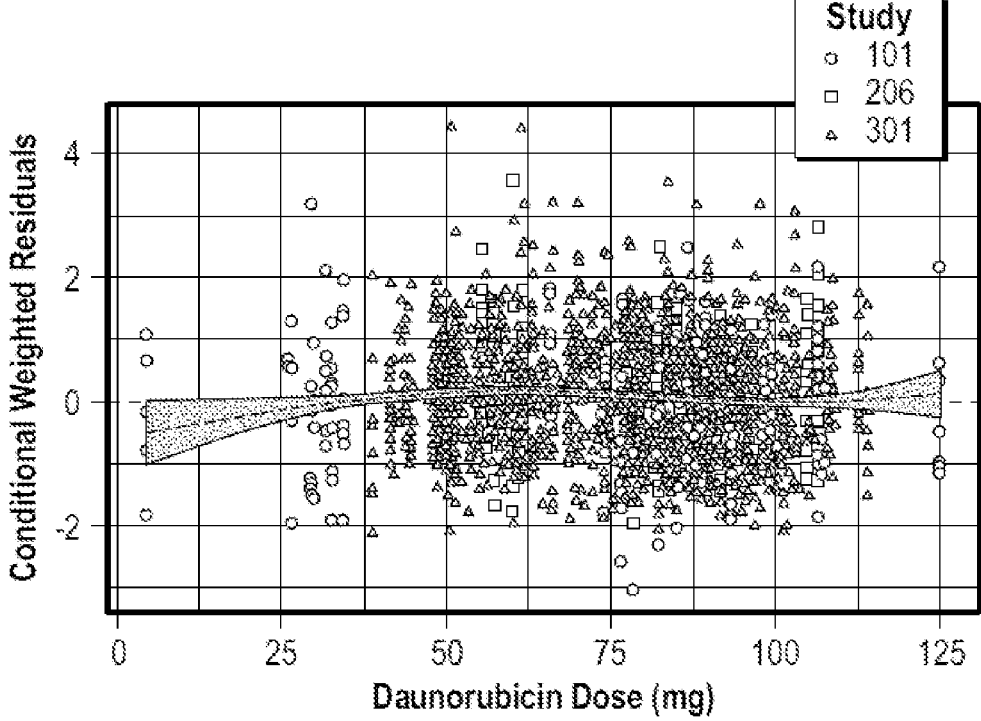
Figure 6E:
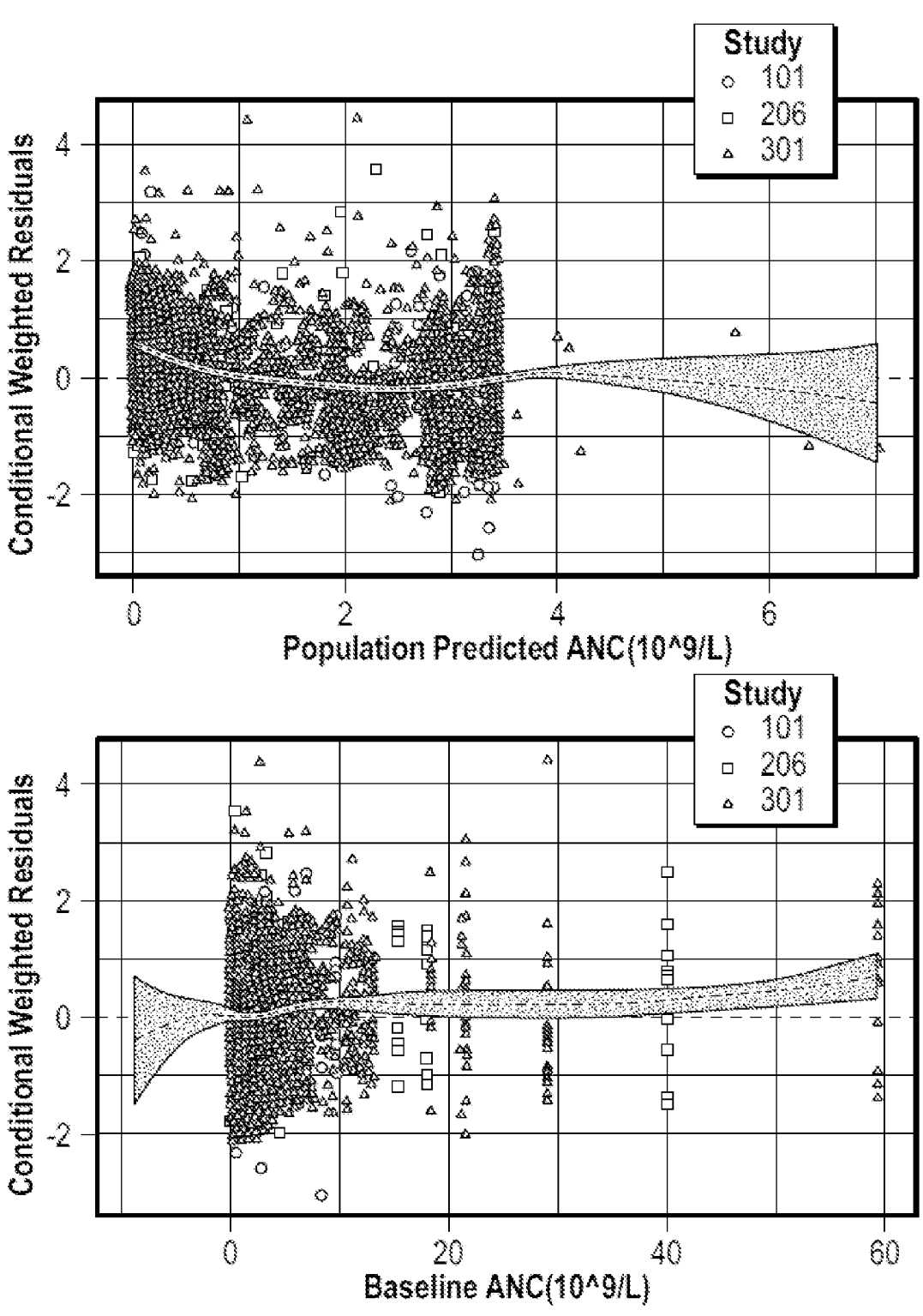
Figure 6F:
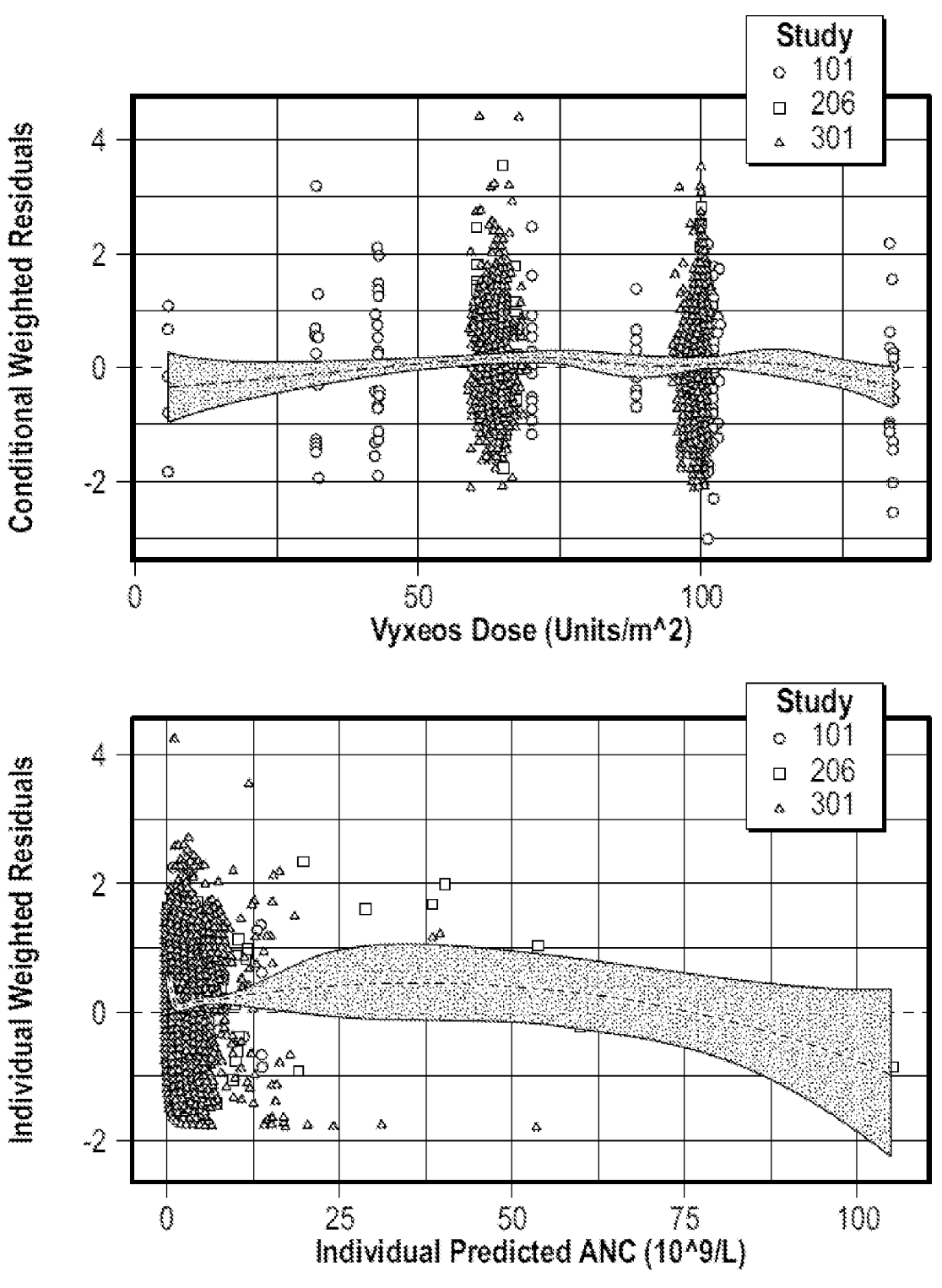

FIGS. 2A-2C show Visual Predictive Check Stratified by Treatment Cycle for the Final Population PK-PD Model.

Figure 1C:
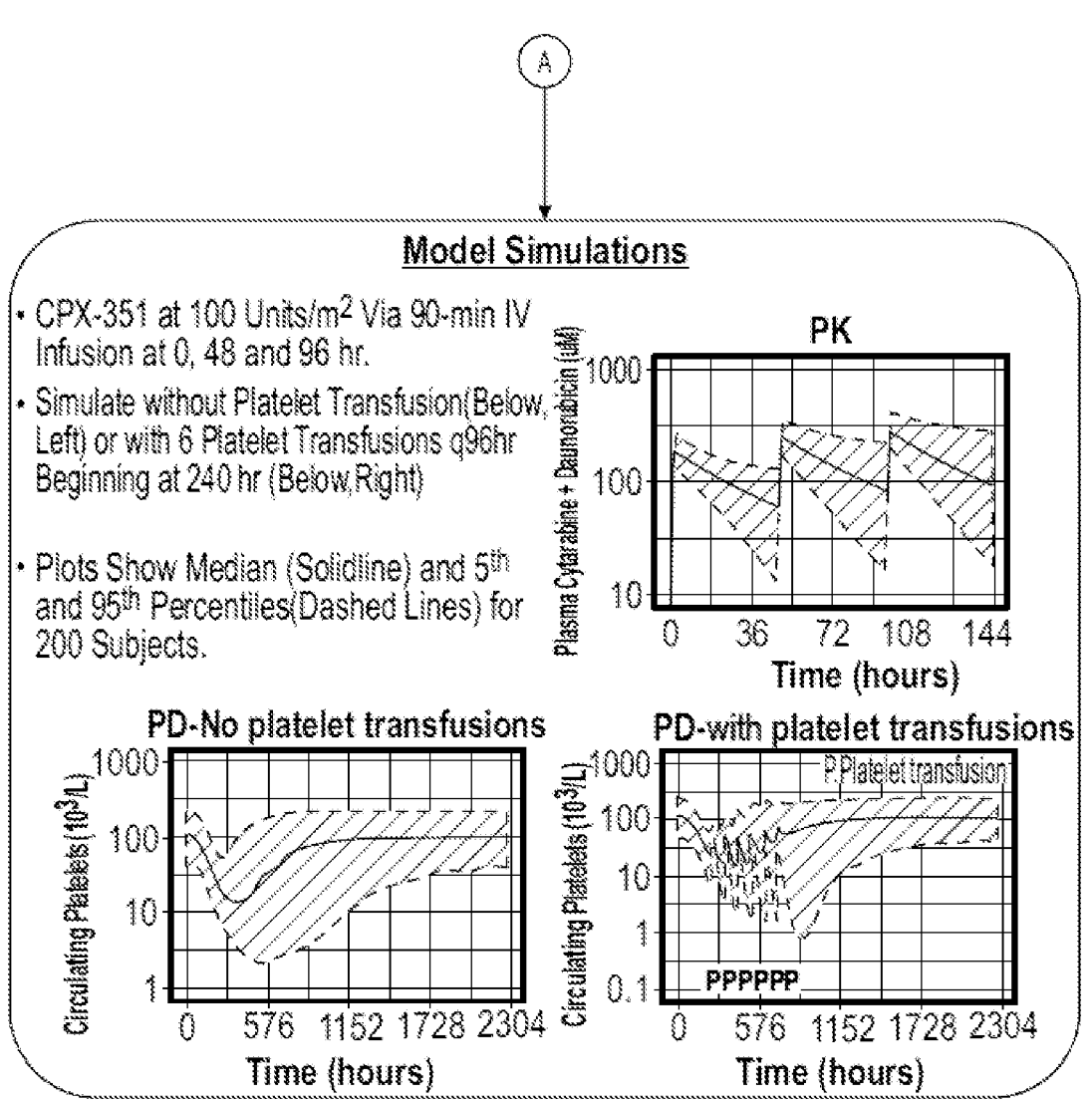

A visual predictive check based on 100 simulated datasets showed reasonably good agreement between the median and the 10th and 90th percentiles of the observed and simulated platelet counts over time since the start of the treatment cycle. For the final dataset, the R Shiny application was used to simulate 200 patients undergoing chemotherapy with either 100 units/m² of CPX-351 via 90-minute IV infusion at 0, 48, and 96 hours (FIGS. 1B and 1C) or with 7+3 as administered in Study 301. Without platelet transfusions, 186 (93.0%) patients reached incomplete recovery (platelet count>50×109/L) within the 96-day simulation period, and the median time from first CPX-351 dose to recovery of platelet count>50×109/L was 618 hours (25.8 days). With intermittent platelet transfusions (6 transfusions every 96 hours starting at 240 hours), 191 (95.5%) patients reached incomplete recovery (platelet count>50×109/L) within the 96-day simulation period, and the median time from first CPX-351 dose to recovery of platelet count>50×109/L was 528 hours (22.0 days).

Conclusions: a maturation PK-PD model was developed to characterize the effect of CPX-351 and 7+3 on platelets in patients with AML, ALL, or MDS. CPX-351 achieved a rapid and substantial suppression of platelet counts, with an estimated $IC_{50}$ of 0.324 μM. The model accounted for the confounding nature of platelet transfusions on platelet dynamics during chemotherapy-induced thrombocytopenia. The final model was successfully embedded in an R Shiny application that can be utilized to evaluate the temporal events of thrombocytopenia following administration of various CPX-351 or 7+3 dosing regimens with intermittent platelet transfusions. These are used to design an appropriate treatment cycle for LiT administration of CPX-351.

Example 2—Modeling of Chemotherapy-Induced Neutropenia (CIN) in Patients Treated with CPX-351 and "7+3"

The CPX-351 and 7+3 studies and Cytarabine/Daunorubicin modeling was performed as in Example 1.
Results shown below:

TABLE 6

| Population PK Parameters for GCSF Agents | | | |
|---|---|---|---|
| Parameter | Population mean equation | Interindividual variability | Reference |
| Filgrastim | | | |
| $F_1$ | 0.105 | — | Wiczling et al.[5] |
| $k_a$, $h^{-1}$ | 0.403 | — | Wiczling et al.[5] |
| $F_2$, h | 0.586 | — | Wiczling et al. |
| $D_2$, h | 6.6 | — | Wiczling et al. |
| $K_D$, nM | 0.0237 | 0.527 (72.6% CV) | Melhem et al. |
| CL, L/h | $0.833 \cdot (WTKG/70)^{0.641}$ | 0.138 (37.1% CV) | Melhem et al. |
| $V_c$, L | $3.12 \cdot (WTKG/70)^{0.943}$ | 0.080 (28.2% CV) | Melhem et al. |
| Pegfilgrastim | | | |
| $F_1$ | 0.646 | 0.194 (44.0% CV) | Melhem et al. |
| $k_a$, $h^{-1}$ | 0.0188 | 0.051 (22.5% CV) | Melhem et al. |
| $K_D$, nM | 0.959 | 0.527 (72.6% CV) | Melhem et al. |
| CL, L/h | $0.362 \cdot (WTKG/70)^{0.641}$ | 0.138 (37.1% CV) | Melhem et al. |
| $V_c$, L | $5.76 \cdot (WTKG/70)^{0.943}$ | 0.080 (28.2% CV) | Melhem et al. |
| Filgrastim or pegfilgrastim | | | |
| $K_{int}$, $h^{-1}$ | 0.113 | 0.325 (57.0% CV) | Melhem et al. |

PK, pharmacokinetic; GCSF, granulocyte colony-stimulating factor; $F_1$, bioavailability of first-order absorption process; $k_a$, first-order absorption rate constant; $F_2$, bioavailability of zero-order absorption process; $D_{2,fil}$, duration of the zero-order absorption process; KD, equilibrium dissociation constant for GCSF and GCSF receptor; CV, coefficient of variation; CL, clearance; WTKG, body weight in kg; Ve, central volume of distribution; $k_{int}$, first-order rate constant for internalization of GCSF receptor complexed with filgrastim or pegfilgrastim.

Population PK-PD analysis was conducted using NON-MEM version 7.3 via implementation of the first-order conditional estimation method with 11-E interaction. Previously developed population PK models for CPX-351 or 7+3

(2-compartment disposition) were used to generate patient-specific cytarabine and daunorubicin concentration-time profiles. Previously reported population PK models for GCSF agents (1-compartment with target-mediated drug disposition) were used to predict patient-specific concentration-time profiles following exogenous GCSF administration based on individual dosing histories and population mean PK parameters.

In the population PK-PD model for chemotherapy-induced neutropenia (CIN), data from Cycle 1 were excluded if patients had an absolute neutrophil count (ANC)<1.0× $10^9$/L prior to the first treatment cycle; data from subsequent cycles were only included if the ANC returned to ≥1.0× $10^9$/L prior to treatment. ANC versus time data were described by a modified maturation PK-PD model proposed by Friberg et al. Stimulation of neutrophil proliferation and maturation by exogenous granulocyte colony stimulating factor (GCSF) agents was driven by the fraction of GCSF receptors bound to exogenous GCSF. Inhibition of neutrophil proliferation by CPX-351 (or 7+3) was driven by an $I_{max}$ function of the sum of the molar concentrations of cytarabine and daunorubicin. Interindividual variability was estimated for select structural PK-PD model parameters using exponential error models. Previously reported population PK models for GCSF agents (1 compartment with target-mediated drug disposition) were used to predict patient-specific concentration-time profiles following exogenous GCSF administration (filgrastim and/or pegfilgrastim) based on individual dosing histories and population mean PK parameters. A graphical screening procedure was first conducted to examine the relationship between patient covariates and key PK-PD model parameters, followed by stepwise forward selection (α=0.01) and backward elimination (α=0.001) to evaluate covariate effects. Baseline Patient Demographics were: Weight, height, age, body mass index, body surface area, sex, race, and ethnicity. Baseline Clinical Laboratory Measures were: Albumin, alkaline phosphatase, alanine aminotransferase, aspartate aminotransferase, total bilirubin, white blood cell count, absolute neutrophil count, platelet count, and creatinine clearance. Disease-related Indices were: Cancer type and Eastern Cooperative Oncology Group performance status. An R Shiny application was developed in conjunction with the mrgsolve package (Metrum Research Group) so the population PK-PD model could be used to simulate neutrophil (or platelet) dynamics following administration of CPX-351 (or 7+3) and GCSF in various dosing regimens; relevant patient demographics were generated with distributions that were comparable to those in the analysis dataset.
Results:

TABLE 7

| Summary Statistics of Selected Baseline Patient Demographics and Clinical Laboratory Measures in the Final Analysis Dataset | | | | | | | |
|---|---|---|---|---|---|---|---|
| Variable | | n | % | Mean | SD | Median | Min | Max |
| Age, y | | 129 | | 66.1 | 9.1 | 67.0 | 23 | 81 |
| Weight, kg | | 129 | | 82.4 | 20.4 | 78.7 | 39.5 | 156 |
| BSA, $m^2$ | | 129 | | 1.96 | 0.28 | 1.94 | 1.3 | 2.8 |
| Platelet count, $10^9$/L | | 129 | | 67.1 | 61.0 | 43.0 | 2 | 289 |
| ANC, $10^9$/L | | 128 | | 4.42 | 7.57 | 1.98 | $0^a$ | 59.4 |
| Received ≥1 | No | 86 | 66.7 | | | | | |
| GCSF agent | Yes | 43 | 33.3 | | | | | |
| Sex | Male | 79 | 61.2 | | | | | |
| | Female | 50 | 38.8 | | | | | |
| Race | Caucasian | 110 | 85.3 | | | | | |
| | Black | 6 | 4.7 | | | | | |

TABLE 7-continued

| Summary Statistics of Selected Baseline Patient Demographics and Clinical Laboratory Measures in the Final Analysis Dataset | | | | | | | | |
|---|---|---|---|---|---|---|---|---|
| Variable | | n | % | Mean | SD | Median | Min | Max |
| | Asian | 4 | 3.1 | | | | | |
| | Other/missing | 9 | 7.0 | | | | | |
| ECOG performance | 0 | 39 | 30.2 | | | | | |
| status | 1 | 76 | 58.9 | | | | | |
| | 2 | 9 | 7.0 | | | | | |
| Cancer type | ALL | 3 | 2.3 | | | | | |
| | AML | 126 | 97.7 | | | | | |

SD, standard deviation;
BSA, body surface area;
ANC, absolute neutrophil count;
GCSF, granulocyte colony-stimulating factor;
ECOG, Eastern Cooperative Oncology Group;
ALL, acute lymphocytic leukemia;
AML, acute myeloid leukemia.
[a]For patients who were neutropenic (ANC <1.0 × $10^9$/L) prior to the first treatment cycle, data from Cycle 1 were excluded from analysis, and data from subsequent cycles were only included if the ANC returned to ≥1.0 × $10^9$/L prior to treatment. However, for the purposes of covariate evaluation, the baseline ANC from Cycle 1 was used, even if the value was <1.0 × $10^9$/L.

The early analysis dataset consisted of 1,797 ANC observations from 129 patients, of whom 43 (33.3%) received GCSF therapy at least once during the study. Incorporation of the stimulatory effect of exogenous GCSF on neutrophil proliferation and maturation significantly improved the model fit (P<0.00001). During covariate evaluation, a strong inverse correlation was observed between mean transit time and baseline ANC (P<0.00001); no other potential covariates met the criteria for inclusion. In the late stages of model development, Imax was estimated to be 1.05 and subsequently fixed at 1, which produced a minor increase of 4.5 units in the minimum value of objective function.

TABLE 8

| Model Fitted PD Parameters for Neutrophils | | | | |
|---|---|---|---|---|
| | CPX-351 | | 7 + 3 | |
| Parameter | Estimate | % SEM | Estimate | % SEM |
| $Circ_0$, $10^9$/L | 3.55 | 8.8 | 3.76 | 10.2 |
| MTT, h at median baseline ANC of 1.98 × $10^9$/L | 113 | 3.6 | 87.8 | 3.2 |
| Power exponent for MTT-ANC relationship | −0.154 | 17.5 | n/a | n/a |
| $I_{max}$ | 1 | Fixed | 1 | Fixed |
| $IC_{50}$, μM | 24.9 | 6.1 | 0.0286 | 28.8 |
| γ | 1 | Fixed | 1 | Fixed |
| $γ_T$ | 0.0794 | 7.6 | 0.0689 | 5 |
| $Stim_1$ and $Stim_2$ | 2.76 | 9.6 | 2.76 | Fixed |

PK, pharmacokinetic; PD, pharmacodynamic; SEM, standard error of the mean; $Circ_0$, baseline ANC; MTT, mean transit time (4/$k_{tr}$); ANC, absolute neutrophil count; $I_{max}$, maximum inhibition of neutrophil proliferation; $IC_{50}$, composite concentration (cytarabine + daunorubicin) at which inhibition is 50% of $I_{max}$; $γ_T$, feedback function exponent; $Stim_1$, slope parameter for stimulation of neutrophil proliferation by the fraction of GCSF receptors bound to exogenous GCSF; $Stim_2$, slope parameter for stimulation of neutrophil maturation by the fraction of GCSF receptors bound to exogenous GCSF; $ω^2$, interindividual variability; CV, coefficient of variation; $σ^2$, residual variability; SD, standard deviation.

Parameters in the PK-PD model were estimated with high precision (<26% standard error of the mean). The population mean for Circo before treatment was estimated to be similar for CPX-351 and 7+3, while the population mean for MTT of maturation was slightly longer with CPX-351 versus 7+3. 7+3 was more potent than CPX-351. Including GCSF effect in the model significantly improved the model fit.

The median time to observe the first blood neutrophil count<0.5×109/L was later following CPX-351 (8.3 days) versus 7+3 (7.4 days) treatment. The median duration with neutrophil counts<0.5×109/L was longer with CPX-351 (23 days) than with 7+3 (14 days). The median lowest neutrophil counts were well below 0.2×109/L for both CPX-351 and 7+3. These results are summarized in Table 9 below.

TABLE 9

| Model-simulated Neutrophil Parameters After CPX-351 or 7 + 3 Treatment | | |
|---|---|---|
| | CPX-351 | 7 + 3 |
| Mean (SD) nadir, $10^9$/L | 0.177 (0.503) | 0.157 (0.417) |
| Median nadir, $10^9$/L | 0.007 | 0.026 |
| Median time to nadir, h | 420 | 312 |
| Median time to 0.5 × $10^9$/L, h | 199 | 178 |
| Median duration <0.5 × $10^9$/L, h | 548 | 328 |

Figure 1D:
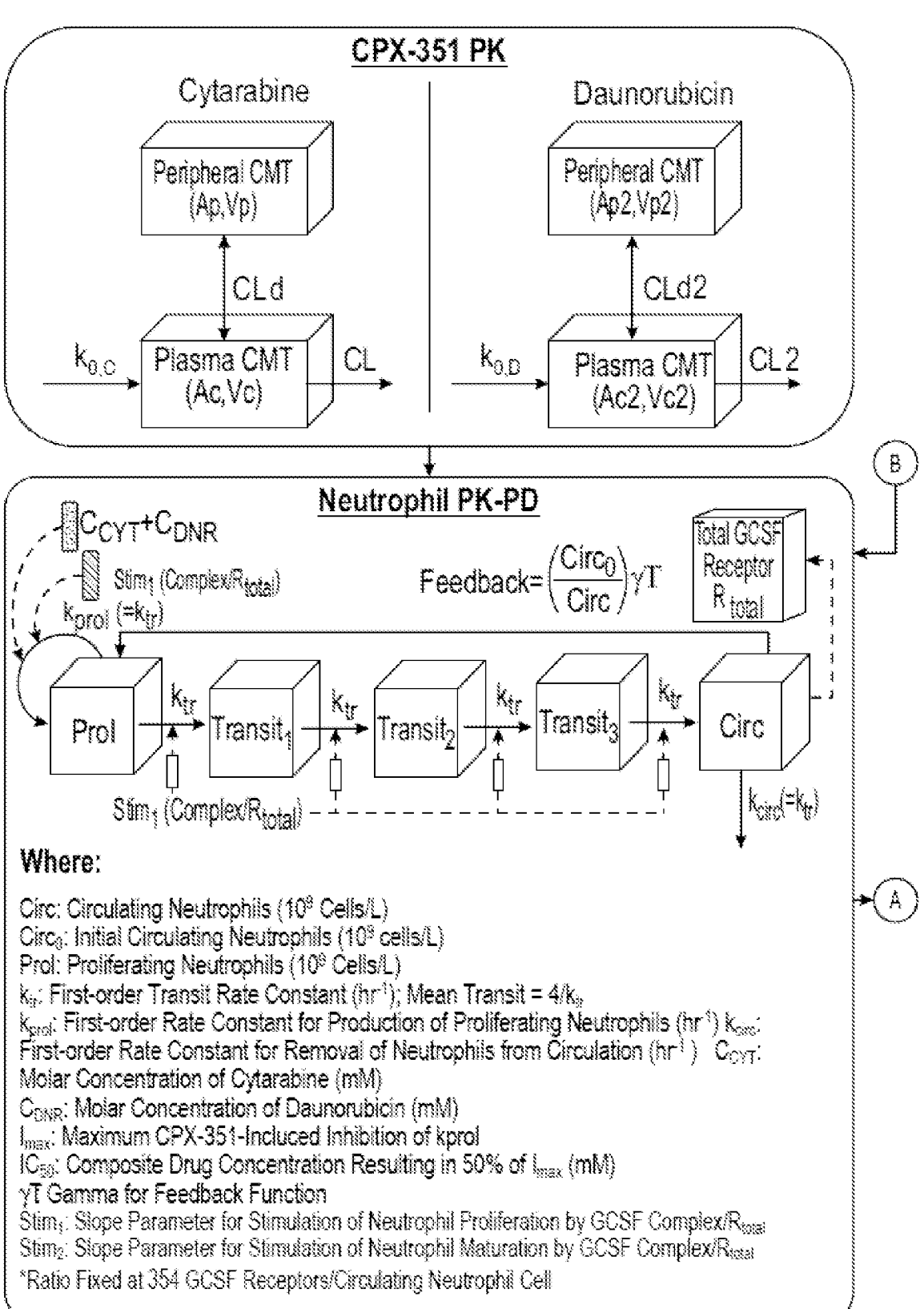
Figure 1E:
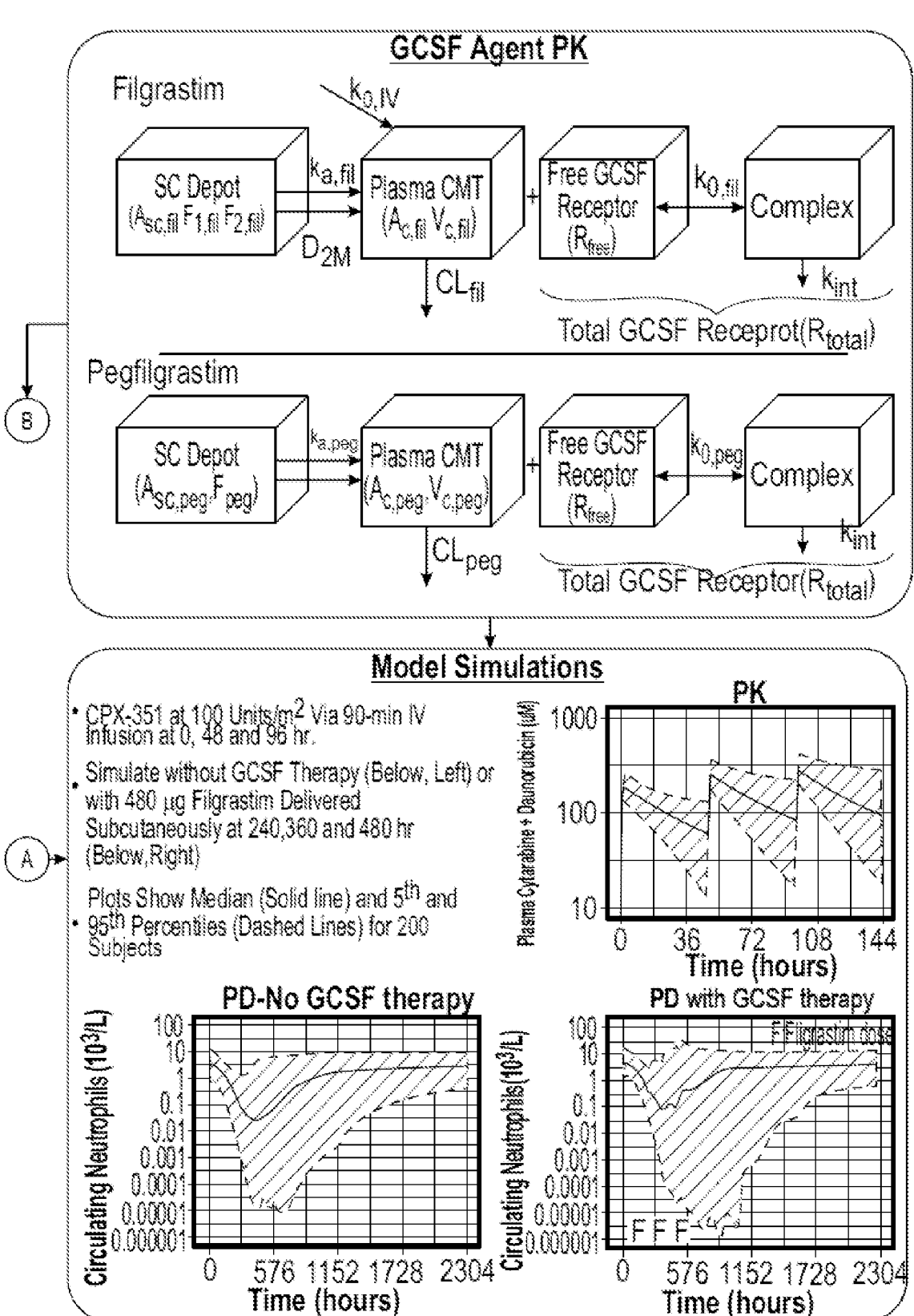
Figure 1F:
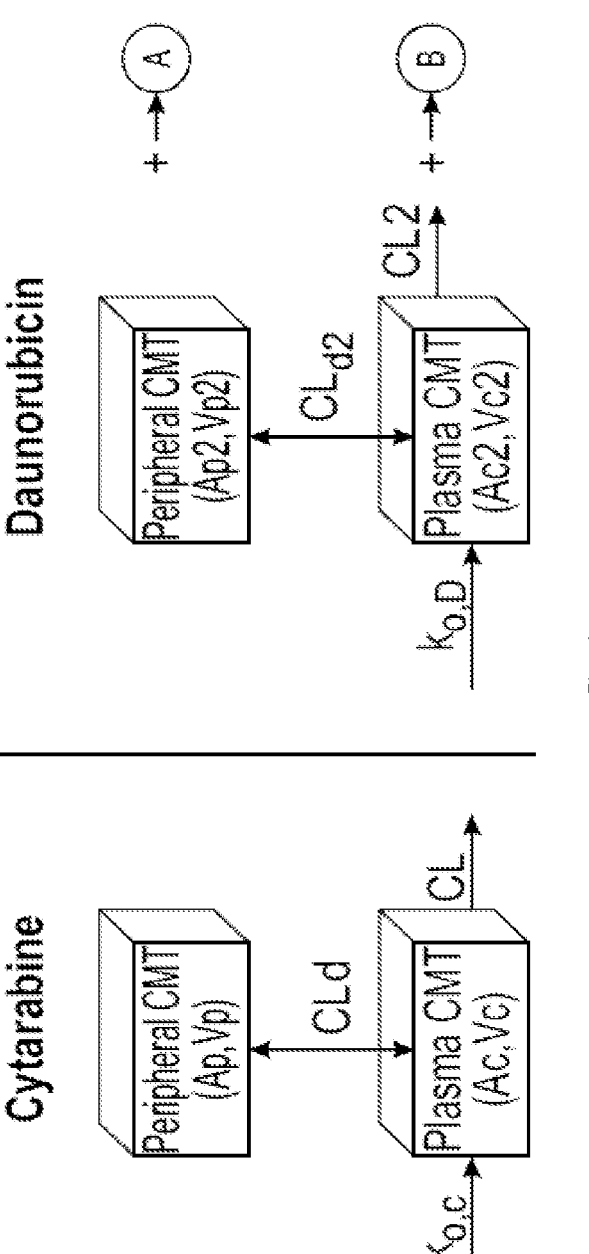
FIGS. 1F and 1G show a schematic representation of the modeling strategy.
Figure 1G:
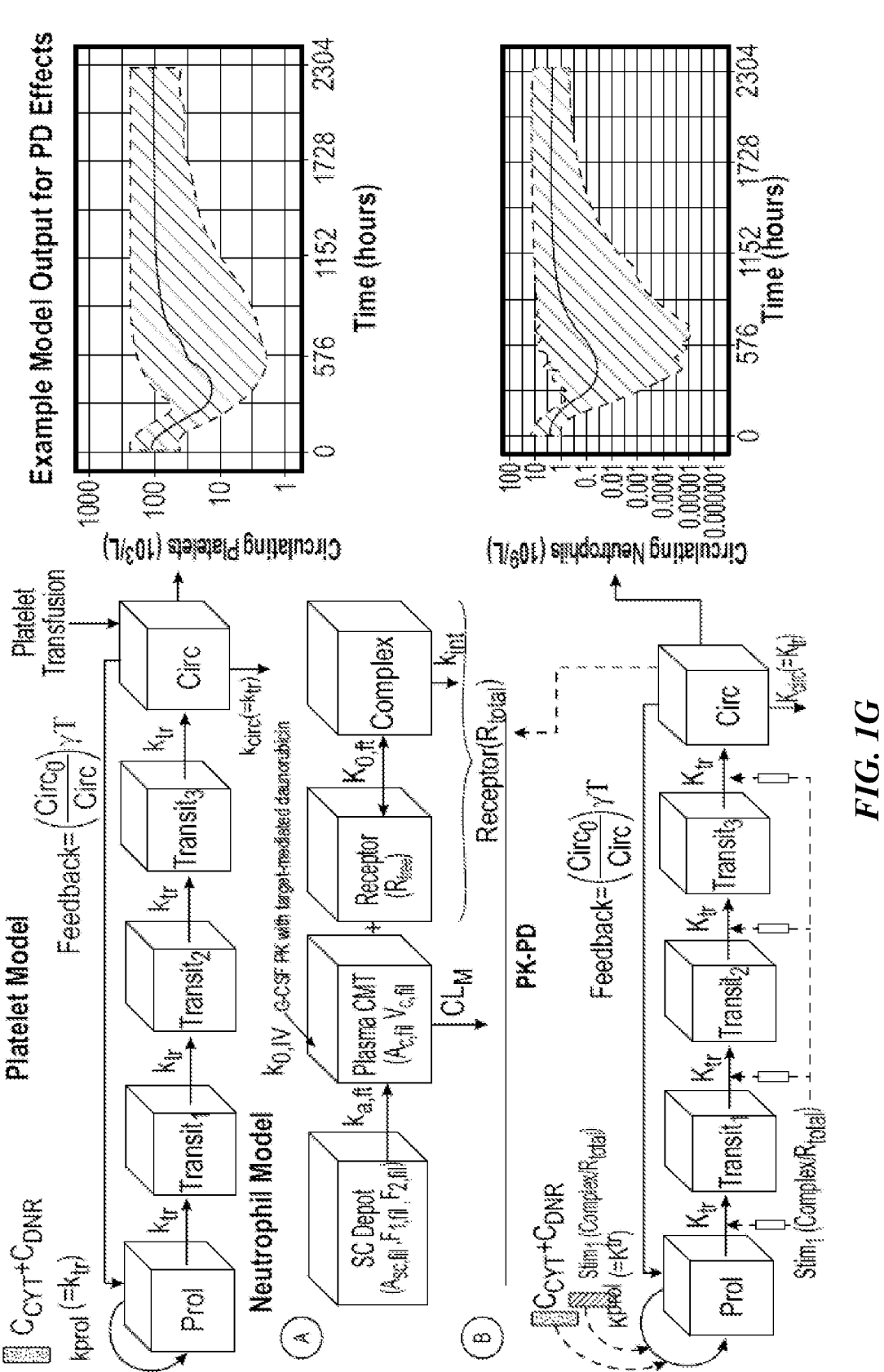

FIG. 2B shows a visual predictive check stratified by treatment cycle for the final population PK-PD model. It is based on 100 simulated datasets showed reasonably good agreement between the median and the 10th and 90th percentiles of the observed and simulated ANC over time since the start of the treatment cycle. The R Shiny application was used to simulate 200 patients undergoing chemotherapy with 100 units/$m^2$ of CPX-351 via 90-minute IV infusion at 0, 48, and 96 hours (FIGS. 1D and 1E). Without GCSF therapy, 172 (86%) patients recovered to ANC>1.0× 109/L within the 96-day simulation period, and the median time from first CPX-351 dose to recovery of ANC>1.0× 109/L was 788 hours (32.8 days). With GCSF therapy (480 μg filgrastim administered subcutaneously at 240, 360, and 480 hours), 176 (88%) patients recovered to ANC>1.0× 109/L within the 96-day simulation period, and the median time from first CPX-351 dose to recovery of ANC>1.0× 109/L was 730 hours (30.4 days).

Conclusions: a maturation PK-PD model was developed to characterize the effect of CPX-351 and 7+3 on ANC in patients with AML or ALL or MDS. CPX-351 achieved a rapid and maximal suppression of ANC (Imax=1) and had an estimated IC50 of 24.9 μM. The model accounted for the confounding nature of concurrent GCSF therapy on neutrophil dynamics during CIN. The final model was successfully embedded in an R Shiny application that can be utilized to evaluate the temporal events of neutropenia following administration of CPX-351 or 7+3 and GCSF therapy in various dosing regimens. The myelosuppressive effects of CPX-351 were different from 7+3 in terms of duration of myelosuppression and time to neutrophil count<0.5×109/L. The median time for initial detection of myelosuppression with CPX-351 was 1 to 2 days later than with 7+3. Additionally, the median duration of myelosuppressive effects was longer with CPX-351 than with 7+3. These results may have implications for the clinical monitoring scheme of patients with AML who receive CPX-351 therapy. These are used to design an appropriate treatment cycle for LIT administration of CPX-351.

Example 3—Simulation of Alternative Dose-Regimen for CPX-351

Simulation of myelosuppression profile for lower dose/regimen scenarios:

Day 1+5; various doses <100 units/m2

Day 1+8; various doses <100 units/m2

Day 1+8+15; various doses <100 units/m2

Other schemes, various doses <100 units/m2

The PK/PD modeling described in Examples 1 and 2 is used to further examine the cell cycle time and Vyxeos treatment effect.

Figure 8:
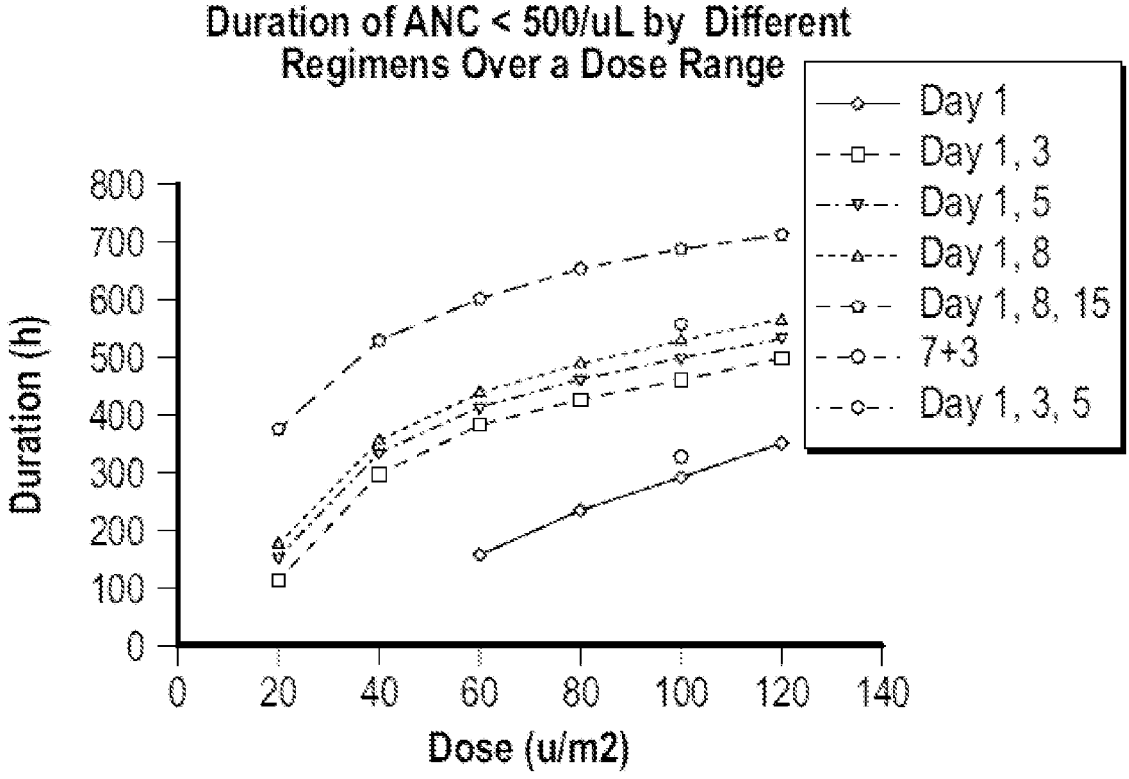
FIG. 8 shows the duration of ANC for a given dose range of CPX-351.

Simulation Outcomes for Absolute Neutrophil Count (ANC): Simulations were conducted using previous developed mechanistic PK/PD model for absolute neutrophil count. FIG. 8 shows the period of ANC below 500/uL after administration of CPX-351. The duration of ANC<500/uL increases as dose increases. Depending on regimen, the duration can be different for a given dose. The duration ANC suppression after Vyxeos standard Day 1, 3, & 5 regimen or 7+3 treatment is also shown in the figure, where Vyxeos showed a longer duration of ANC suppression than 7+3. This longer suppression is consistent with clinical observations.

Figure 9A:
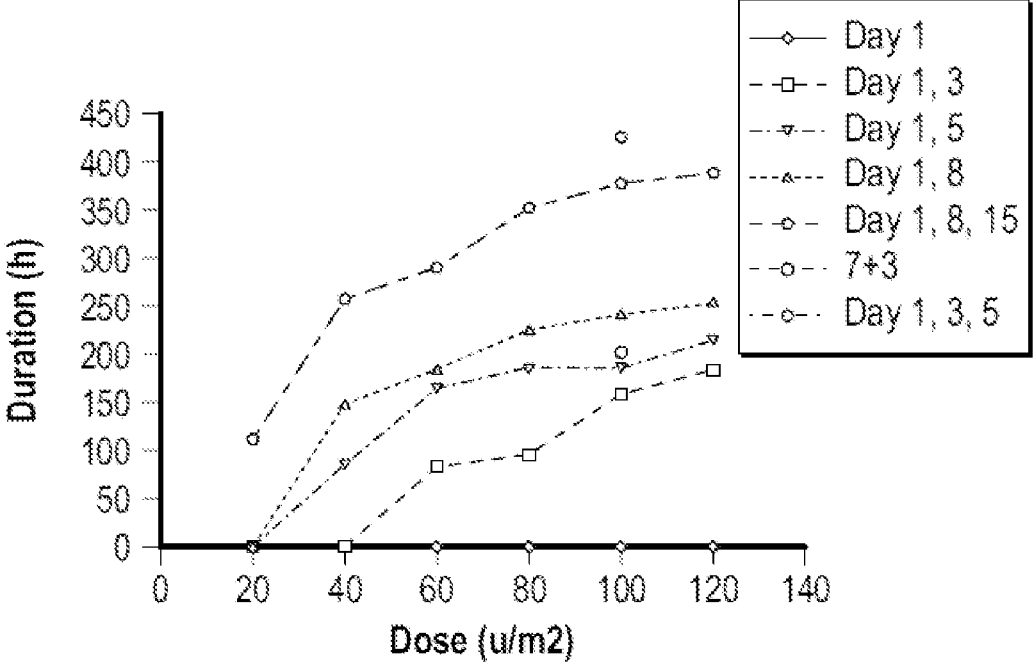
FIGS. 9A and 9B show the duration of platelet count for a given dose range of CPX-351.
Figure 9B:
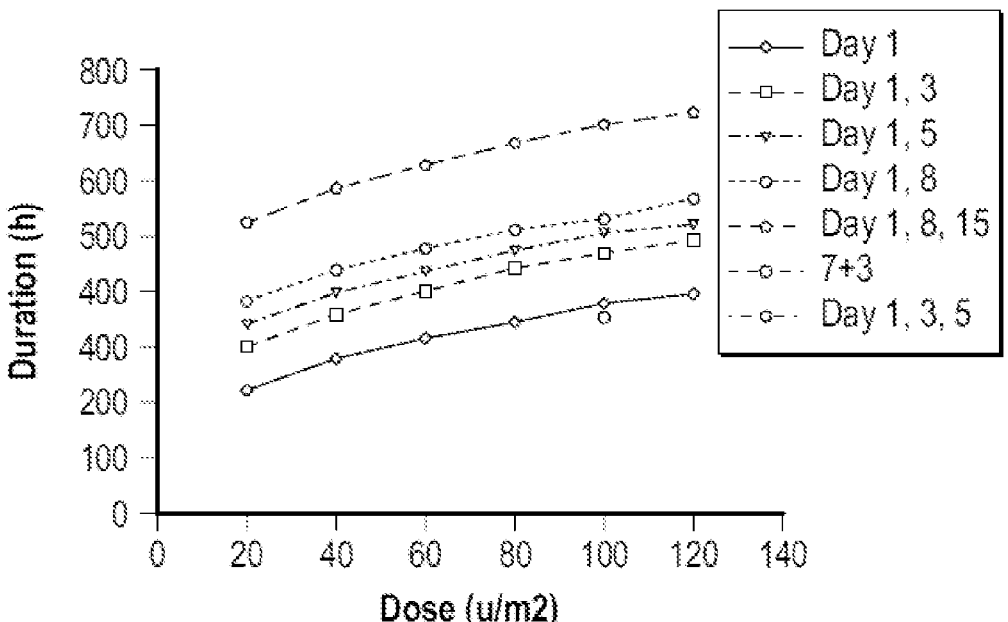

Simulation outcome for platelet count: Simulations were conducted using previous developed mechanistic PK/PD model for platelet count. During simulation, no platelet infusion was given and the starting platelet count is around 10,000/uL. FIGS. 9A and 9B show the period of platelet count below 50, 000 or 20,000/uL after administration of CPX-351. The duration of platelet suppression increases as dose increases. Depending on regimen, the duration can be different for a given dose. The duration platelet suppression after Vyxeos standard Day 1, 3, & 5 regimen or 7+3 treatment is also shown in the figure, where Vyxeos showed a longer duration of ANC suppression than 7+3. This longer suppression is consistent with clinical observations. Additionally, Vyxcos Day 1, 3, 5 regimen produced most longest suppression period (<20,000/uL) than other regimens.

Figure 10A:
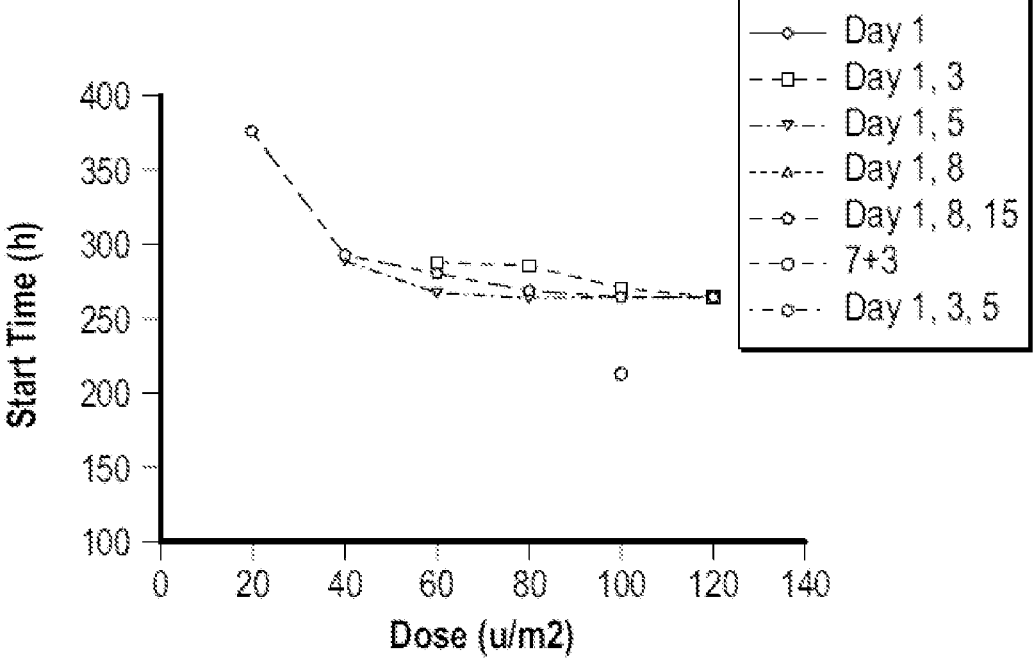
FIGS. 10A and 10B show the first time of different platelet count using different dosing regimen.
Figure 10B:
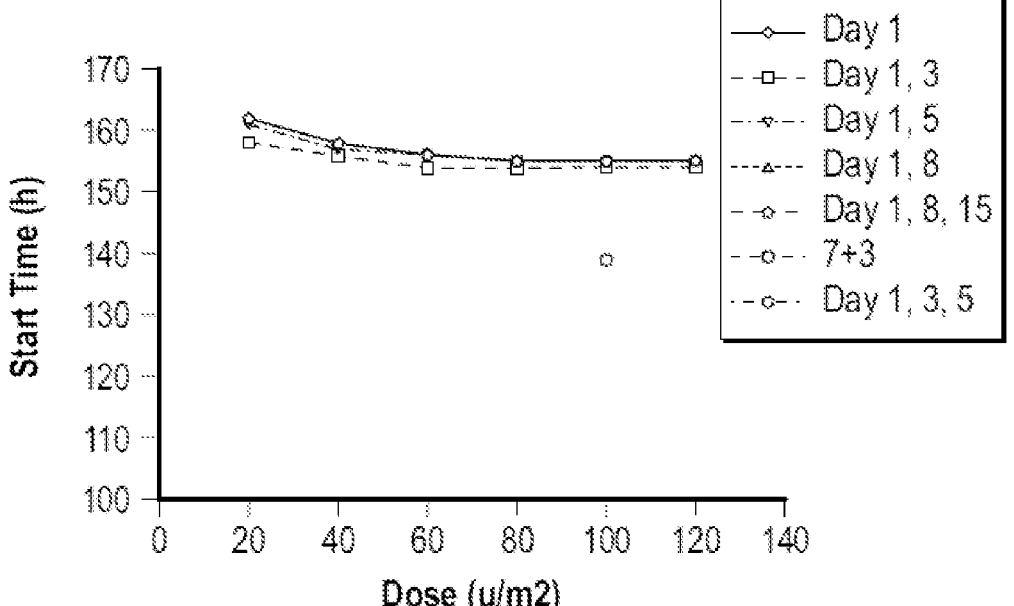

Simulation outcome for platelet count: this data appears to be the first time to observe a platelet count below a certain threshold level that is not related to regimen. Rather, it is related to the drug properties and dose. Vyxeos treatment results in a later observation than 7+3 treatment. With increase of dose of Vyxeos, the median start-time of observing platelet count<20,000/uL approaches 258 h (Day 10-11 post the first dose). With increase of dose of Vyxeos, the median start-time of observing platelet count<50, 000/uL approaches 154 h (Day 6-7 post the first dose). For 7+3, the median start-time of observing platelet count<20,000/uL is around 200 h (Day 8-9 post start of the treatment). For 7+3, the median start-time of observing platelet count<50,000/uL is around 139 h (Day 5-6 post start of the treatment). The results are shown in FIGS. 10A and 10B.

Figure 11:
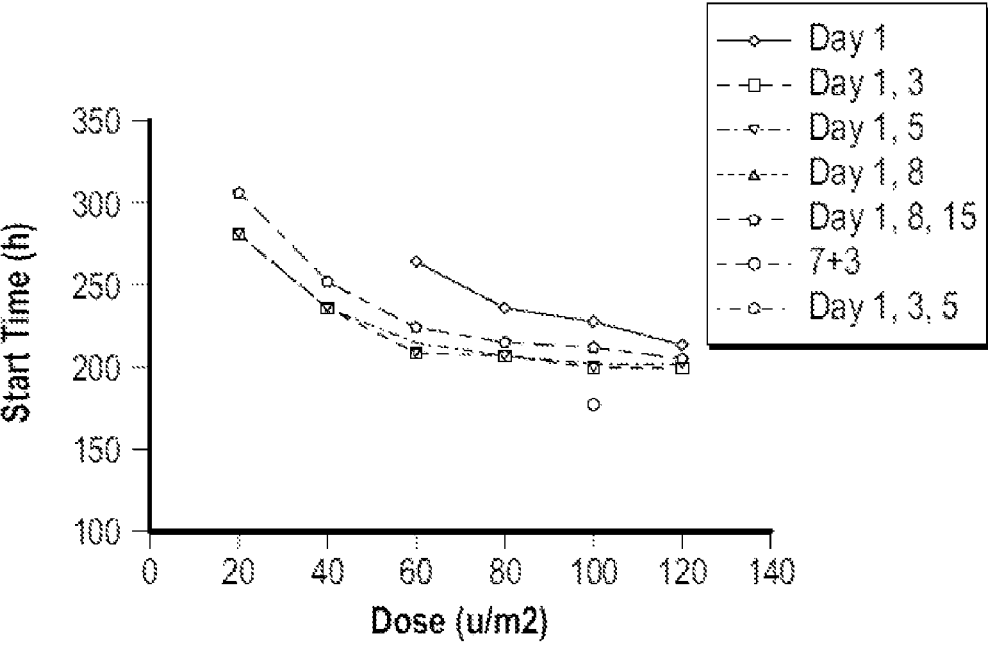
FIG. 11 show the first time of different ANC using different dosing regimen.
Figure 12A:
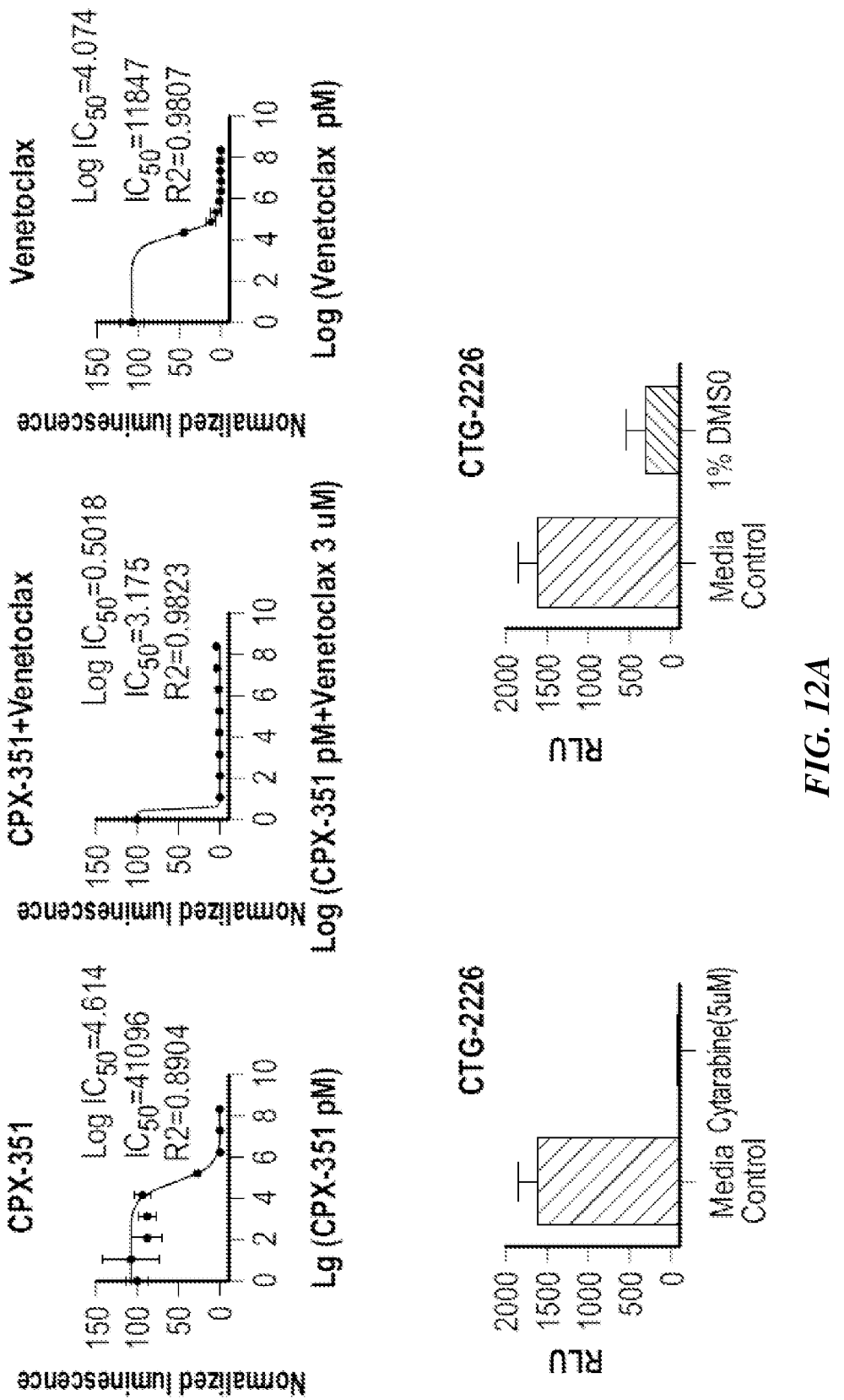
Figure 13A:
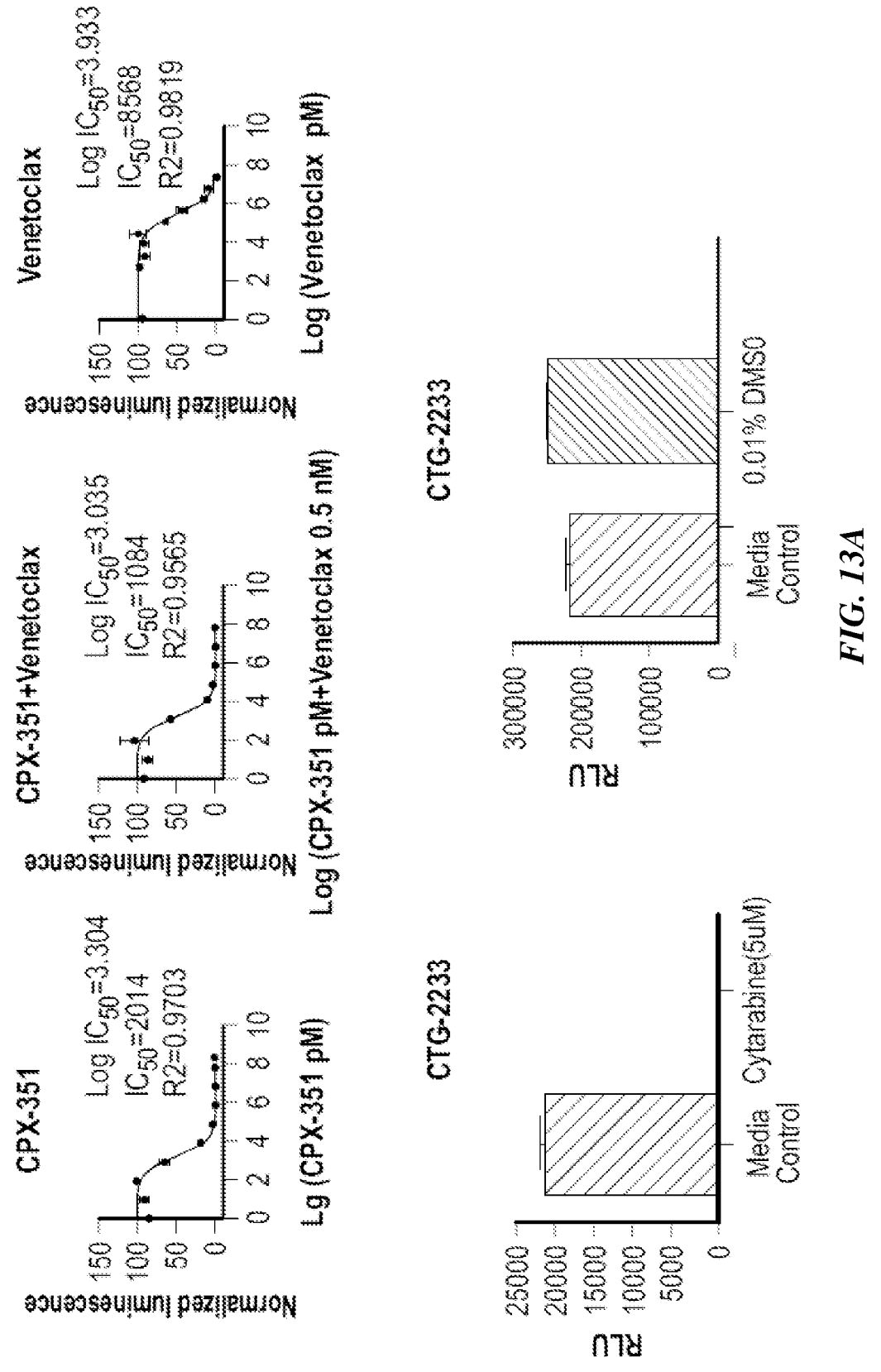

Simulation outcome for neutrophils: this data appears to be the first time to observe a ANC below a certain threshold related to the drug properties and dose. Vyxeos treatment results in a late-onset but prolonged neutropenia than 7+3 treatment. With increase of dose of Vyxeos, the median start-time of observing ANC<500/uL approaches 200 h (Day 8-9 post the first dose). For 7+3, the median start-time of observing ANC<500/uL is around 178 h (Day 7-8 post start of the treatment). The results are shown in FIG. 11.

Example 4—CPX-351 and Venetoclax Show Synergy in Ex Vivo Leukemia Models

In order to evaluate the cytotoxicity of CPX-351 in combination with Venetoclax, various drug:drug combinations were tested in 15 Passage 1 (P1) models of human Acute Myeloid Leukemia (AML) and assayed for cell viability.

The study type and duration used was an ex-vivo cell killing assay with primary leukapharesis-derived AML cells using a 96-well plate format, 90 wells, 6-day incubation, Cell Titer Glo viability endpoint with $IC_{50}$.

AML Models used were CTG-2226, CTG-2227, CTG-2228, CTG-2231 to CTG-2234, CTG-2236, CTG-2237, CTG-2238, CTG-2242, CTG-2243, CTG-2251, CTG-2255, and CTG-2299. The IDH1/2 status for each cell line was noted and some were Wildtype while others were IDH1 or IDH2 mutant. AML cells were seeded at a density of 20,000 cells/100 ul per well in a 96 well plate in enriched media. Therapeutic agents were added to wells on Day 0 along with cell plating according to the experimental design in volume of 100 ul/well bringing the total volume to 200 ul/well.

CPX-351 and Venetoclax were each tested alone (100 uM) as well as in combination as outlined in Table 10 below:

TABLE 10

| CPX-351 + Venetoclax screening in AML cell models | | | | |
|---|---|---|---|---|
| Group | -n-replicates | Test Agent | High Dose (uM) | Dilution Series |
| 1 | 3 | CPX-351 | 100 | 10 dose points- 1:10 dilutions |
| 2 (1st 7 lines) | 3 | CPX-351 | 100 | 10 dose points- 1:10 dilutions |
| | | Venetoclax | Fixed @ 3 uM | Fixed |
| 2* (remaining 8 lines) | 3 | CPX-351 | 100 | 10 dose points- 1:10 dilutions |
| | | Venetoclax | Fixed @ 0.5 nM | Fixed |
| 3 | 3 | Venetoclax | 100 (Reduced starting to 1 uM) | 10 dose points- 1:3 dilutions |

Cytarabine (5000 nM) concentration was used as a positive control; Media+vehicle were used as negative control. Plates were kept in 37° C./5% CO2 incubator. Media was not changed during the 6-day incubation period with test agents. On day 6, cell viability was tested using Cell Titer Glo assay.

Cell Titer Glo Assay: Plates were removed from incubator and equilibrated to room temperature up to 30 minutes. 100 ul of Cell Titer Glo was added to wells and mixed for 2 minutes by keeping the plates on plate rocker. The plates were incubated at room temperature for 10 minutes to stabilize luminescent signal. Luminescence was recorded using Tecan plate reader.

Data Analysis: data was reported as changes in RLU units to different drug concentrations as luminescence read is directly proportional to cell viability.

The results from first 7 cells all demonstrated strong synergy. This may be due to the high concentrations of venetoclax in the incubation and so testing of lower concentrations is in progress. The results from remaining 8 cell models demonstrated either synergistic or additive effects of combining Vyxeos and Venetoclax in 7 cell models, with only showing antagonistic effect. FIGS. 12A, 12B, 13A, and 13B show the change in $IC_{50}$ for the CTG-2226 and CTG-2233, cell lines respectively.

Example 5—In Vitro Cytotoxicity of CPX-351 Plus Venetoclax Compared with Hypomethylating Agents or Cytarabine Plus Venetoclax In order to evaluate the cytotoxic effects of CPX-351 plus venetoclax, versus combinations of venetoclax plus azacitidine, decitabine or cytarabine, various drug:drug combinations were tested on acute leukemia cell lines and assayed for cell viability.

AML cell lines used were: HL-60 (ATCC), SKM-1 (Sekisui XenoTech) and KG-1 (ATCC). Acute Lymphoid Leukemia (ALL) cell lines used were: CCRF-CEM (ATCC), MOLT-3 (ATCC), and Jurkat E6-1 (ATCC).

Each cell line was seeded in triplicate in round-bottom 96-well plates with $5\times10^4$ cells in 180 uL in each well. After 24 hours, cells were dosed with CPX-351, venetoclax, azacitidine, decitabine, and/or cytarabine. CPX-351 and cytarabine were each dosed in a titration starting at 50 μM (for CPX-351, this was measured by its cytarabine content), with 8 additional serial dilutions of 5× each and a final group with no treatment. Venetoclax, azacitidine, and decitabine were each dosed in a titration starting at 100 μM, with 8 additional serial dilutions of 5× each and a final group with no treatment. For the combination treatment of CPX-351 and venetoclax, the same titrations were used as in single-agent treatment. About 72 hours after dosing, cell viability was measured by CellTiter-Glo assay (Promega) according to manufacturer instructions; luminescence was measured and ICso values were estimated by Cytation Multi-Mode reader (BioTek). Combination index (CI) was calculated as above based on the Chou and Talalay method using the equation $CI=[D_1/(Dx)_1]+[D_2/(Dx)_2]$; CI was calculated at 50%- and 70%-maximal effective concentrations ($EC_{50}$ and $EC_{70}$) for the drug combinations.

The $IC_{50}$ and CI values are outlined in Tables 11 and 12 below, respectively:

TABLE 11

| IC₅₀ Values of Tested Drugs in AML and ALL Cell Lines | | | | | | |
|---|---|---|---|---|---|---|
| | | IC₅₀ values, μM | | | | |
| Cell line | Cell Origin | CPX-351 | Venetoclax | Azacitidine | Decitabine | Cytarabine |
| HL60 | AML | 0.76 | 0.05 | 1.42 | 0.82 | 0.85 |
| KG-1 | AML | 2.2 | 2.1 | 4.0 | 0.36 | 0.24 |
| SKM-1 | AML | 0.69 | 1.5 | 0.42 | 0.24 | 0.54 |
| CCRF-CEM | ALL | 0.13 | 2.8 | 1.58 | 0.04 | 0.03 |
| MOLT-3 | ALL | 0.09 | 1.0 | 4.03 | 0.23 | 0.08 |
| Jurkat E6-1 | ALL | 0.24 | 3.5 | 0.98 | 0.10 | 0.04 |

TABLE 12

| CI for Drug Combinations | | | | | |
|---|---|---|---|---|---|
| Cell line | Cell origin | CPX-351 + Venetoclax | Azacitidine + Venetoclax | Decitabine + Venetoclax | Cytarabine + Venetoclax |
| HL60 | AML | 0.70 | 0.71 | 1.66 | 1.01 |
| KG-1 | AML | 0.53 | 0.59 | 0.77 | 0.95 |
| SKM-1 | AML | 0.91 | 1.29 | 1.14 | 1.93 |
| CCRF-CEM | ALL | 0.70 | 0.86 | 1.99 | 0.99 |
| MOLT-3 | ALL | 0.74 | 0.63 | 0.73 | 0.68 |
| Jurkat E6-1 | ALL | 0.79 | 1.14 | 1.40 | 1.33 |

CI, combination index; AML, acute myeloid leukemia; ALL, acute lymphoid leukemia.

Note:

CI < 1 is synergistic; CI = 1 is additive; CI > 1 is antagonistic.

Figure 14A:
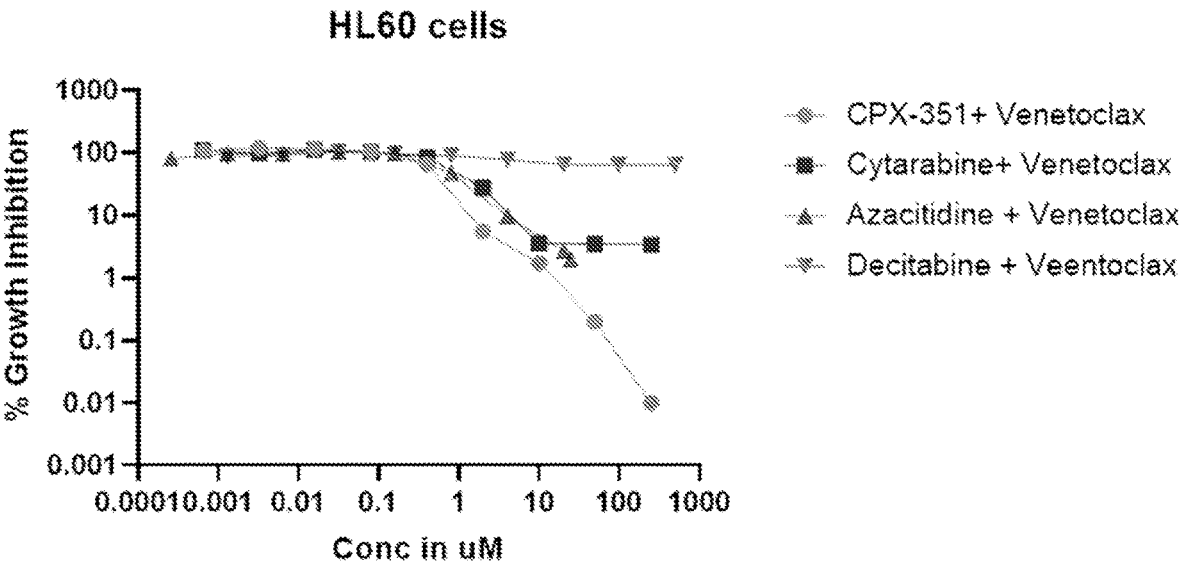
FIGS. 14A, 14B and 14C show the change in $IC_{50}$ for the HL60, KG-1 and SKMI cell lines, respectively.
Figure 14B:
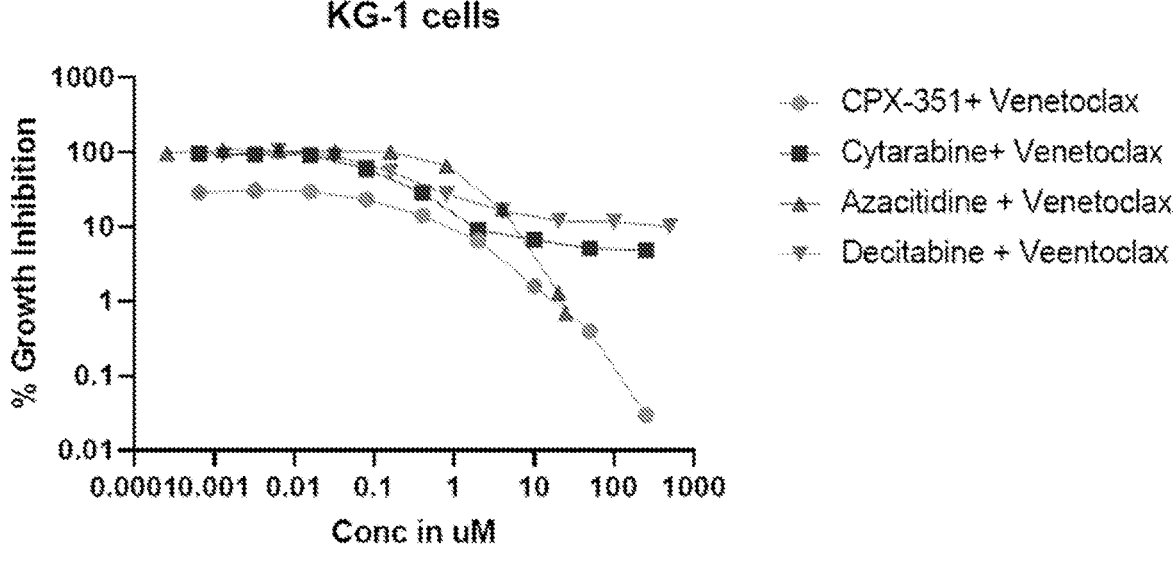
Figure 14C:
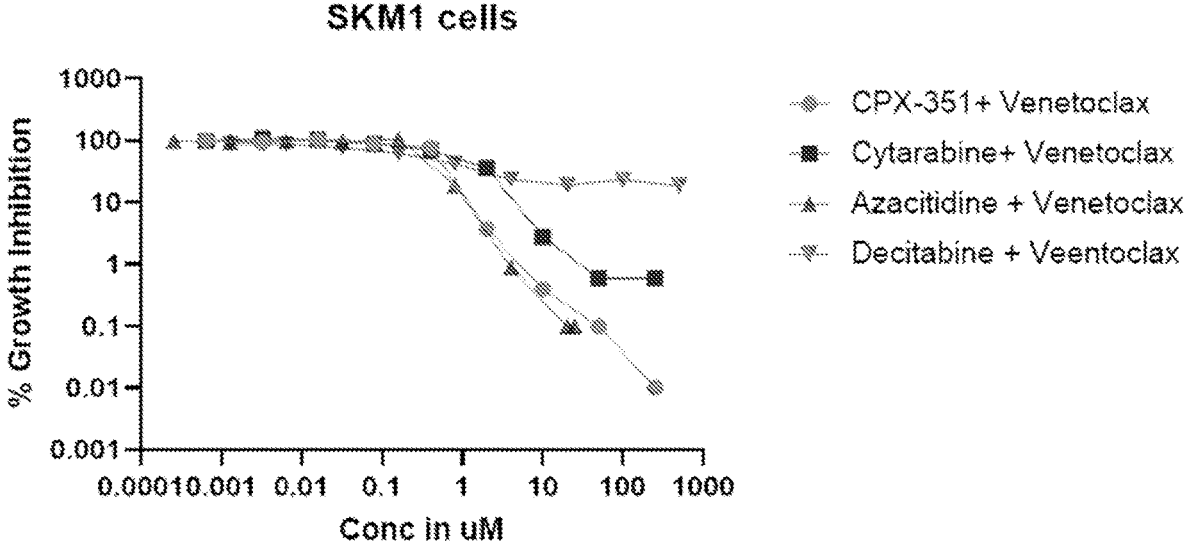

FIGS. 14A-14C show the comparison of the maximum growth inhibition of different drug combinations in the AML cell lines.

The data together demonstrated that the combination of CPX-351 plus venetoclax is synergistic or additive in all AML and ALL cell lines tested. In addition, the results show that the combination of venetoclax with hypomethylating agents (azacitidine or decitabine) showed synergy in the KG-1 and MOLT-3 cell lines, but antagonism in the SKM-1 and Jurkat E6-1 cell lines; other cell lines showed variable effects. The combination of venetoclax with cytarabine, showed synergy only in the MOLT-3 cell line; in other cell lines, additive or antagonistic effects were observed.

Example 6—Clinical Trial of CPX-351 and Venetoclax

A Phase 1b trial of CPX-351 Lower Intensity Therapy (LIT) plus venetoclax is conducted as First Line Treatment for Subjects with AML who are ineligible for Intensive Chemotherapy.

The primary objectives are to determine the maximum tolerated dose (MTD) of the combination of CPX-351 and venetoclax when administered to subjects with newly diagnosed Acute Myeloid Leukemia (AML) who are ineligible for intensive chemotherapy (ICT). In addition, the safety of this combination is to be determined.

Secondary objections are to perform initial assessments of efficacy, including complete remission (CR), complete remission with incomplete hematologic recovery (CRi), composite complete remission rate (CRc: CR+CRi), overall response rate (ORR; CR+CRi+partial response [PR]) and assessment of Minimal Residual Disease (MRD) status (negative I positive) in subjects with documented CR or Cri. The study is also to determine the pharmacokinetics (PK) of CPX-351 and venetoclax when given in combination.

The duration of remission (DOR) and overall survival (OS) and event-free survival (EFS) 1-year after first administration of the study treatment will also be explored.

The study will comprise 2 phases: a Dose Escalation Phase and an Expansion Phase, in which all subjects will receive a combination of CPX-351 and venetoclax. In the Dose Escalation Phase, a 3+3 design will be employed and enroll up to 24 subjects with newly diagnosed AML who are ineligible for standard ICT using stepwise dose escalations of CPX-351 in combination with 400 mg venetoclax in each cohort to determine the MTD for the combination.

After determining the MTD of the combination of CPX-351 and venetoclax, the Expansion Phase will commence with 20 additional subjects treated with the combination to determine an initial response rate based on both morphologic assessment and MRD. Stopping rules for excessive toxicity and for futility will be included for the Expansion Phase.

Subjects will be followed for safety (1 month after End of Treatment) and every 2 months(±2 weeks) for survival (up to 1 year after the first administration of study treatment). Each subject will be evaluated for response at the end of each cycle. Those subjects with CR, CRi or PR will be offered up to a total of 4 cycles of CPX-351 and venetoclax, as deemed appropriate by the treating physician. Subjects with NR (no response) after 2 cycles will stop treatment. Subjects who have completed 4 cycles of treatment will be managed at the investigator's discretion, as per institutional guidelines.

In each cycle, CPX-351 will be administered on Days 1 and 3, and venetoclax will be administered on Days 2 through 21. During Cycle 2 Day 3 of the Dose Escalation Phase, venetoclax will be administered at the study site during the infusion of CPX-351 to permit PK assessment.

Blood collection for PK studies will be conducted during the first and second cycles of therapy for all dose cohorts in the Dose Escalation Phase. Blood collection for sparse PK sampling will also be performed in the Expansion Phase for subjects receiving their Day 3 and Day 4 care at the study site. During Cycle 1 Day 3 of the Expansion Phase, venetoclax will be administered at the study site during the infusion of CPX-351 to permit PK assessment. The Dose Escalation and Definition of MTD. The Dose Escalation Phase will employ a 3+3 design to determine the dose limiting toxicities (DLTs) and MTD as follows. The first 3 subjects will be treated at Dose Level 1 (see Table 13). If this is deemed safe (see specifics below), then dose escalations will proceed as follows:

TABLE 13

| Dose-escalation levels | | |
|---|---|---|
| Dose Level | CPX-351 dosing (per 28-day cycle[b,c]) | Venetoclax dosing (per 28-day cycle[b]) |
| 1 | 20 units/m$^2$ on Days 1 and 3 | 400 mg/day on Days 2 to 21 |
| 2 | 40 units/m$^2$ on Days 1 and 3 | 400 mg/day on Days 2 to 21 |
| 3 | 60 units/m$^2$ on Days 1 and 3 | 400 mg/day on Days 2 to 21 |
| 4 | 75 units/m$^2$ on Days 1 and 3 | 400 mg/day on Days 2 to 21 | a Each dose escalation will be confirmed by a safety assessment committee.
[b]Patients may receive up to 4 cycles of therapy.
[c]1 unit = 1 mg cytarabine + 0.44 mg daunorubicin.

Dose escalation algorithm: If none of the first 3 evaluable subjects at a dose level experience a DLT, then the next 3 subjects will be treated at the next dose level (dose escalation). If 1 out of the first 3 evaluable subjects experiences a DLT, then an additional 3 subjects will be treated at the same dose (for a total of 6 subjects at a dose level). If 1 out the 6 total evaluable subjects at a dose level experiences a DLT, then the next 3 subjects will be treated at the next dose level (dose escalation). If 2 or more of the first 3 evaluable subjects at a dose level experience a DLT, then no additional subjects will be treated at this or higher dose level. If 2 or more of the 6 total evaluable subjects experience a DLT, then no additional subjects will be treated at this or higher dose level.

MTD determination algorithm: If ≥2 out of 3 or ≥2 out of 6 evaluable subjects experience a DLT at Dose Level 1 (starting dose), then the study will stop and no MTD will be determined. Otherwise, the MTD will be determined as the highest dose level at which either 0 out of 3 or 1 out of 6 evaluable subjects experiences a DLT. If this is Dose Level 4, then the maximum administered dose will be Dose Level 4, and for the purposes of this study, Dose Level 4 will be considered the MTD. The DLT observation period will be Days 1 to 49 after starting treatment, with a minimum observation period of 28 days. Subjects who are eligible to progress to a second cycle, or who have transitioned to an alternative therapy, may have an abbreviated DLT observation period (ie, less than 49 days). Subjects who do not complete a full cycle of therapy due to disease-related mortality or who withdraw from the study for reasons unrelated to drug effects, and have not experienced a DLT, will not be evaluable for DLTs. These subjects will be replaced. A regular teleconference, occurring approximately every 3 weeks, will be held among the Jazz medical and clinical team and study investigators to review safety data (hereafter referred to as the Safety Assessment Committee

[SAC]). The SAC will also meet at the completion of each dosing cohort to determine whether 1) dose escalation will proceed with the next cohort; 2) the current dose level requires additional assessment; 3) the MTD has been reached; or 4) whether the study will be stopped. To mitigate the risk of potential tumor lysis syndrome, during the first cycle a venetoclax dose ramp-up will occur on Days 2 through 4, followed by treatment at the target dose on Days 5 to 21. For subsequent cycles, venetoclax will be administered at the full target dose during Days 2 through 21.d Main Inclusion Criteria (Full List Provided in Body of Protocol)

Subject must have newly diagnosed AML with histological confirmation by World Health Organization (WHO) criteria Definition of Subjects Who are Ineligible for Standard ICT:

Each subject must meet the following criteria characterizing him/her as ineligible to receive ICT within 21 days prior to the first day of therapy to be enrolled in the study:

≥75 years of age

OR

≥18 to 74 years of age and fulfilling at least 1 criteria associated with lack of fitness for ICT as follows:

Eastern Cooperative Oncology Group (ECOG) Performance Status of 2 to 3;

Cardiac history of Congestive Heart Failure (CHF) requiring treatment or left ventricular ejection fraction (LVEF)≤50%.

Diffusing Capacity of the Lung for Carbon Monoxide (DLCO)≤65% or Forced Expiratory Volume in 1 second (FEV1)≤65%;

Creatinine clearance (CrCl) ≥30 mL/min to <45 mL/min calculated by the Cockcroft-Gault formula;

Moderate hepatic impairment with total bilirubin >1.5 to ≤3.0×Upper Limit of Normal (ULN);

Other comorbidity that the physician judges to be incompatible with conventional intensive chemotherapy which must be reviewed and approved by the study medical monitor before study enrollment.

Additional Criteria:

In addition, all subjects must meet the following criteria:

If the subject is 2≥75 years of age, then ECOG Performance Status must be 0-2.

Subject must have adequate renal function as demonstrated by a CrCl≥30 mL/min (calculated by the Cockcroft Gault formula or measured by 24-hour urine collection).

Subject must have adequate liver function as demonstrated by:

Aspartate aminotransferase (AST)≤3.0×ULN*

Alanine aminotransferase (ALT)≤3.0×ULN*

Bilirubin≤1.5×ULN (subjects who are <75 years of age may have bilirubin of ≤3.0×ULN)*

*Unless considered to be due to leukemic organ involvement.

Female subjects must be either postmenopausal defined as:

Age>55 years with no menses for ≥2 years without an alternative medical cause.

OR

Age≤55 years with no menses for >12 months without an alternative medical cause AND a follicle-stimulating hormone level>40 IU/L;

OR

Permanently surgical sterile (bilateral oophorectomy, bilateral salpingectomy or hysterectomy);

OR

A woman of childbearing potential practicing at least 1 protocol specified method of birth control starting at Study Day 1 through at least 6 months after the last dose of study treatment.

A woman of childbearing potential must have negative results for pregnancy test performed:

At Pretreatment with a serum sample obtained within 14 days prior to the first study treatment administration, and Prior to dosing with urine sample obtained on Cycle 1 Day 1, if it has been >7 days since obtaining the serum pregnancy test results.

Subjects with borderline pregnancy tests at Pretreatment must have a serum pregnancy test >3 days later to document continued lack of a positive result.

Male subjects who are sexually active, must agree, from Study Day 1 through at least 6 months after the last dose of study treatment, to practice protocol specified methods of contraception. Male subjects must agree to refrain from sperm donation from initial study treatment administration through at least 6 months after the last dose of study treatment.

Subject must have a white blood cell count≤25×109/L. (Note: subjects who have undergone hydroxyurea administration or leukapheresis for therapeutic cytoreduction will be considered eligible).

Main Exclusion Criteria (full list provided in body of protocol) Subjects who meet any of the following criteria will be excluded from the study:

Subject has ECOG Performance status >3, regardless of age.

Subject has received any prior treatment for AML with the exception of hydroxyurea, which is allowed up until the initiation of therapy/first dose of CPX-351. (Note: Prior treatment for Myelodysplastic Syndrome is allowed except for use of cytarabine or daunorubicin.)

Subject has favorable risk cytogenetics ((t8;21), inv(16), t(16;16) or t 15;17) karyotype abnormalities) as categorized by the National Comprehensive Cancer Network (NCCN) Guidelines Version 2.2014 for AML Subject had an antecedent myeloproliferative neoplasm (MPN) including myelofibrosis, essential thrombocytosis, polycythemia vera, or chronic myelogenous leukemia (CML) with or without BCR-ABL 1 translocation and AML with BRC-ABL 1 translocation.

Subject has acute promyelocytic leukemia (APL).

Subject has known Central Nervous System (CNS) involvement with AML.

Subject has known Human Immunodeficiency Virus (HIV) infection (due to potential drug-drug interactions between antiretroviral medications and venetoclax). HIV testing will be performed at Pretreatment, if required per local guidelines or institutional standards. Subject is known to be positive for hepatitis B virus (HBV), or hepatitis C virus (HCV) infection. (Inactive hepatitis carrier status or low viral hepatitis titer on antivirals [nonexclusionary medications] are not excluded.)

Test Product, Dose and Mode of Administration:

CPX-351 is provided as a sterile, preservative-free, purple, lyophilized cake in a single-use vial. Each vial of CPX-351 contains 44 mg daunorubicin and 100 mg cytarabine. After reconstitution (but before final dilution) each mL contains 2.2 mg daunorubicin and 5 mg cytarabine. CPX-351 is administered as an IV infusion over approximately 90 minutes. Venetoclax is available in 3 strengths and is self-administered as an oral dose once daily with a meal and water:

The 100 mg tablet is provided as an oblong, biconvex shaped, pale yellow film-coated tablet debossed with "V" on one side and "100" on the other side.

The 50 mg tablet is provided as an oblong, biconvex shaped, beige film-coated tablet debossed with "V" on one side and "50" on the other side.

The 10 mg tablet is provided as a round, biconvex shaped, pale yellow film-coated tablet debossed with "V" on one side and "10" on the other side.

Example 7—Clinical Trial of CPX-351 and Venetoclax—Patient Results

Patient A: An 87-year-old white male with newly diagnosed therapy-related AML with a history of prior lym- Patient B: A 74-year-old white male with newly diagnosed de novo AML who was considered unfit for intensive chemotherapy (an ISICT patient) was enrolled at dose level 1 in the dose-escalation phase, and received 20 units of CPX-351 (Daunorubicin 8.8 mg/m$^2$ and Cytarabine 20 mg/m$^2$) on days 1 and 3 and Venetoclax on days 2-21 (Venetoclax was administered 400 mg/day with an initial dose ramp-up from days 2-4 of Cycle 1 of 100 mg/day, then 200 mg/day and then 400 mg/day). The subject has thus far received three cycles of this regimen. The subject achieved CR at the end of cycle 1 and continued to be in CR after cycle 2. This subject is currently ending cycle 3 and the treatment plan beyond this has not yet been finalized as it will depend on his response to cycle 3.

Table 14 clarifies criteria for CR and CRi

TABLE 14

| Response criteria in AML | | |
|---|---|---|
| Category Response | Definition | Comment |
| CR without minimal residual disease (CR$_{MRD-}$) | If studied pretreatment, CR with negativity for a generic marker by RT-qPCT, or CR with negativity by MFC | Sensitivities vary by marker tested, and by method used; therefore, test used and sensitivity of the assay should be reported; analyses should be done in experienced laboratories (centralized diagnostics) |
| Complete remission (CR) | Bone marrow blasts <5%; absence of circulating blasts and blasts with Auer rods; absence of extramedullary disease; ANC ≥1.0 × 10$^9$/L (1000/μL); platelet count ≥100 × 10$^9$/L (100 000/μL) | MRD+ or unknown |
| CR with incomplete hematologic recovery (CRi) | All CR criteria except for residual neutropenia (<1.0 × 10$^9$/L [1000/μL]) or thrombocytopenia (<100 × 10$^9$/L [100 000/μL]) | | phoma who was considered unfit for intensive chemotherapy (an ISICT patient) was enrolled at dose level 1 in the dose-escalation phase (as outlined in Example 6), received 20 units of CPX-351 (Daunorubicin 8.8 mg/m$^2$ and Cytarabine 20 mg/m$^2$) on days 1 and 3 and was scheduled to take Venetoclax from days 2-21 (Venetoclax was administered 400 mg/day with an initial dose ramp-up from days 2-4 of Cycle 1 of 100 mg/day, then 200 mg/day and then 400 mg/day). The subject inadvertently took Venetoclax for an additional 8 days during this cycle and was considered not evaluable for Dose Limiting Toxicity (DLT); however he remained being treated. At the end of cycle 1, the subject had prolonged myelosuppression that eventually resolved before moving to cycle 2. During the second cycle, the subject received 20 units of CPX-351 (Daunorubicin 8.8 mg/m$^2$ and Cytarabine 20 mg/m$^2$) on days 1 and 3 and a reduced duration of dosing for Venetoclax 400 mg/day from days 2-14 due to the prolonged myelosuppression at cycle 1. The subject achieved CRi at the end of cycle 1 and had an upgraded response of CR with a further reduction in blast percentage at the end of cycle 2 (MRD results from central lab at the end of cycle 1=3.12% and at the end of cycle 2=0.22%). This subject is no longer being treated.

Example 8—Study Design

The dose of CPX-351 was constant: (daunorubicin 44 mg/m$^2$+araC 100 mg/m$^2$) IV on D1,3,5 of induction and (daunorubicin 29 mg/m$^2$+araC 65 mg/m$^2$) IV on D1,3 during consolidation. The starting effective dose of Venetoclax (Ven) was 300 mg (at the −1 dose level) on D2-21 for the safety lead-in cohort, composed of patients with R/R AML. Interruption of Ven after D14 was allowed if a D14 bone marrow (BM) was hypocellular and without evidence of leukemia. Dose adjustments for Ven were made for concomitant moderate and strong CYP3A inhibitors. Upon encountering 3/6 patients with DLT (cytopenias >43 days), dose level −2 was explored (Ven 300 mg on D2-8) and expanded. Once safety was confirmed, two expansions cohorts were opened to confirm safety and efficacy: Cohort A for pts with R/R AML and Cohort B for pts with newly diagnosed AML. Patients with adequate organ function, ECOG PS<2 were allowed on study and prior Ven exposure was allowed. Initial dose-escalation design is described in Table 15. Dose Finding is described in Table 16.

TABLE 15

Initial dose-escalation design

Dose-Escalation Table (Planned 28 day cycle)

| | | CPX-351 [mg/m²] | Venetoclax Dosing (PO on D 2-21) | |
|---|---|---|---|---|
| Dose Level | All Patients | Patients on strong CYP3A inhibitor | Patients on moderate CYP3A inhibitor | Patients NOT on moderate or strong CYP3A inhibitor |
| -1 | 44 (induction); 29 (consolidation) | 50 mg | 150 mg | 300 mg |
| 1 | 44 (induction); 29 (consolidation) | 100 mg | 200 mg | 400 mg |

Ramp Up

| Day 2 | Day 3 | Day 4 | Target Dose |
|---|---|---|---|
| 100 mg | 200 mg | 400 mg | 400 mg |

TABLE 16

Dose-Escalation Table (Planned 28 day cycle)

| | | CPX-351 [mg/m²] | Venetoclax Dosing (PO on D 2-21) | |
|---|---|---|---|---|
| Dose Level | All Patients | Patients on strong CYP3A inhibitor | Patients on moderate CYP3A inhibitor | Patients NOT on moderate or strong CYP3A inhibitor |
| -2 | 44 (induction); 22 (consolidation) | 50 mg on D 2-8 | 150 mg on D 2-8 | 300 mg On D 2-8 |
| -1 | 44 (induction); 29 (consolidation) | 50 mg on D 2-8 | 150 mg on D 2-21 | 300 mg on D 2-21 |
| 1 | 44 (induction); 29 (consolidation) | 100 mg on D 2-21 | 200 mg on D 2-21 | 400 mg on D 2-21 |

Ramp Up

| Day 2 | Day 3 | Day 4 | Target Dose |
|---|---|---|---|
| 100 mg | 200 mg | 400 mg | 400 mg |

Example 9-Structural Components of CPX-351: A Cytarabine and Daunorubicin-Loaded Liposome The liposome CPX-351 encapsulates the antineoplastic agents cytarabine and daunorubicin. Cytarabine, also known as ara-C, is a nucleoside metabolic inhibitor that halts the proliferation of a variety of mammalian cells. Daunorubicin, also referred to as daunomycin, is classified as an anthracycline topoisomerase inhibitor. A liposomal combination of the two chemotherapeutics (VYXEOS®) is approved by the FDA to treat adults with newly-diagnosed therapy-related acute myeloid leukemia (AML) or AML with myelodysplasia-related changes.

Cytarabine and daunorubicin are encapsulated in CPX-351 at an optimal molar ratio of 5:1. The cytotoxic agents are surrounded by liposomal membranes composed of distearoylphosphatidylcholine (DSPC), distearoylphosphatidylglycerol (DSPG), and cholesterol in a 7:2:1 molar ratio. Evidence suggests that CPX-351 preferentially accumulates in leukemia cells. Previous in vivo studies have shown uptake of intact CPX-351 lipsomes by bone marrow cells. In a murine model of leukemia, greater uptake of CPX-351 was observed in leukemia cells than in healthy bone marrow cells. Post-internalization, liposomal degradation likely facilitates the release of cytarabine and daunorubicin into the intracellular environment.

Example 10—Treatment with CPX-351 Significantly Improved Remission Rates and Overall Survival in Adults with Newly Diagnosed Secondary AML Occurring more frequently with advanced age, secondary AML accounts for approximately one-quarter of AMLs and is associated with poor outcomes. Treatment with CPX-351 was compared to a standard-of-care cytarabine and daunorubicin regimen (referred to herein as 7+3) in a survival study of 60-75 year old human subjects newly diagnosed with high risk secondary AML. The two treatments were assessed in a randomized, open-label, phase III trial with 309 participants.

Patients were randomly assigned to receive induction and consolidation therapy with CPX-351 or the 7+3 regimen. Subjects were stratified by age (60 to 69 and 70 to 75) and AML subtype (therapy-related AML, AML with a history of myelodysplastic syndrome [MDS] with and without prior hypomethylating agents, AML with a history of chronic myelomonocytic leukemia [CMML], and de novo AML with MOS-related cytogenetic abnormalities). To achieve complete remission (CR) or CR with incomplete neutrophil or platelet recovery (CRi), patients were eligible to receive up to two cycles of induction chemotherapy followed by a maximum of two cycles of consolidation therapy. Attending physicians performed hematopoietic cell transplantation (HCT) at their discretion.

Initial induction therapy with CPX-351 consisted of 90-minute infusions of liposomal 100:44 mg/m² cytarabine:daunorubicin on days 1, 3, and 5. A second induction course of CPX-351 was administered on days 1 and 3 to patients who did not achieve hypoplastic bone marrow on a day 14 bone marrow assessment. Patients who reached CR/CRi status after CPX-351 induction therapy received a post-remission treatment that consisted of up to two cycles of 65:29 mg/m² cytarabine:daunorubicin on days 1 and 3.

The 7+3 cohort was treated with an initial induction course that consisted of a 7-day continuous infusion of 100 mg/m² cytarabine with three once-daily doses of 60 mg/m² daunorubicin on day 1, day 2, and day 3. The secondary induction course and post-remission consolidation therapy were identical in the 7+3 group. These courses consisted of a 5-day continuous infusion of 100 mg/m² cytarabine with once-daily doses of 60 mg/m² daunorubicin on days 1 and 2.

Time-to-event end points were evaluated using a stratified log-rank test to compare treatment groups. The Kaplan-Meier method was used to estimate the distribution of these end points over time. A Cox proportional hazards regression model stratified by age and AML subtype was used to estimate HRs and 95% Cis. A Mantel-Haenszel test was used to compare remission rates and other binary end points. A sample size of 270 patients was expected to result in 236 deaths, factoring in accrual within 2 years, minimum follow-up of 1.2 years, and an estimated median OS of 0.526 years in the 7+3 treatment group, giving this trial 93.7% power and a one-sided a of 0.025 to detect a hazard ratio (HR) of 0.635 between treatment arms. An additional 30 patients were accrued to account for ineligible patients and patients who withdrew consent.

In comparison to 7+3, CPX-351 was associated with a significantly higher overall remission rate (CR+CRi=47.7% v 33.3%; two-sided P=0.016) and CR rate (37.3% v 25.6%; two-sided P=0.040). CR and CR+CRi (overall remission rate) were assessed according to the Revised International Working Group Criteria for AML. Of the 309 participants in the study, 91 patients (29.4%) received allogeneic HCT. There was no significant difference in the number of patients who received allogeneic HCT between treatment groups (52 [34.0%] of 153 patients in the CPX-351 cohort and 39 [25.0%] of 156 in the 7+3 cohort; two-sided P=0.098).

CPX-351 significantly improved OS. With a median follow-up period of 20.7 months, median survival in the CPX-351 cohort surpassed that of the 7+3 cohort (9.56 vs. 5.95 months; HR, 0.69; 95% CI, 0.52 to 0.90; one-sided P=0.003). Survival was analyzed after 236 deaths (104 in the CPX-351 group and 132 in the 7+3 group). The CPX-351 1-year Kaplan-Meier (KM)-estimated OS far surpassed the 7+3 estimate (41.5% vs. 27.6%). Similarly, the 2-year KM-estimated OS for CPX-351 (31.1%) was nearly three times that of 7+3 (12.3%).

In patients who achieved CR+CRi after an initial induction course, the median time to neutrophil (≥500/uL) and platelet (≥50,000/uL) recovery was longer in those treated with CPX-351 (35.0 and 36.5 days, respectively) versus 7+3 (29 and 29 days, respectively). In patients who received a subsequent induction course, treatment with CPX-351 extended median recovery time by at least 7 days when compared to 7+3 (median time to ≥500/μL ANC: 35 days vs. 28 days; median time to ≥50,000/μL platelets: 35 days vs. 24 days). Despite these findings, the response rates and survival data in this trial favored CPX-351 as the superior treatment for adults with newly diagnosed secondary AML.

Example 11—Efficacy and Safety of CPX-351 and Venetoclax Combination Therapy for AML The efficacy and safety profile of CPX-351 combined with venetoclax for the treatment of AML was evaluated in human subjects. Venetoclax (VENCLEXTA®) is approved by the FDA to treat chronic lymphocytic leukemia and small lymphocytic lymphoma. During the lead-in phase, adult patients (≥18 years old) with relapsed and/or refractory (R/R) AML were eligible. Patients with R/R AML were grouped into dose expansion Cohort A. Prior treatment with venetoclax was permissible for R/R AML participants. Patients (18-65 years old) with de novo AML, who had not received any prior therapy for AML, were grouped into dose expansion Cohort B. Patients were screened to determine adequate organ function (bilirubin: ≤2 mg/dL; AST/ALT: ≤3× upper limit of normal (ULN) or <5×ULN if related to leukemic involvement; creatinine: <1.5×ULN; known cardiac ejection fraction of >45% within the past 3 months). Further regarding eligibility, patients must have rated <2 on the Eastern Cooperative Oncology Group (ECOG) performance status. The ECOG is a scale used to assess the progression of an individual's illness, with zero representing a person who is fully active and able to carry on all pre-disease performance without restriction.

Table 17 shows patient characteristics, including age, cytogenetics, and blast cell count. The blast percentage is of particular importance as it can determine an AML diagnosis. Patients received induction and consolidation courses of combination therapy with CPX-351 and venetoclax. Induction therapy consisted of intravenous CPX-351 on days 1, 3, and 5. Venetoclax was orally administered from day 2 through day 21. Patients were eligible to receive up to four consolidation courses. Consolidation therapy consisted of intravenous CPX-351 on day 1 and day 3, and oral venetoclax from day 2 through day 21. Up to 4 consolidation cycles were administered.

TABLE 17

| Patient characteristics, including age, cytogenetics, and blast cell count | | |
| --- | --- | --- |
| Characteristic (N = 20) | Parameter | N (%) or Median (Range) |
| Age, y | Median (Range) | 51 (29-71) |
| Cytogenetics | Diploid, −Y | 3 (15) |
| | Adverse | 9 (45) |
| | Intermediate, non Diploid | 5 (25) |
| | Favorable | 1 (5) |
| | Insufficient | 2 (10) |
| Bone marrow Blast % | Median (Range) | 34 (2-88) |
| WBC [×10⁹/L] | Median (Range) | 2.2 (0.3-34.5) |
| Peripheral Blood Blast % | Median (Range) | 27 (4-96) |
| Serum Creatinine | Median (Range) | 0.87 (0.48-1.67) |
| Total Bilirubin | Median (Range) | 0.4 (0.2-1) |
| No. Prior Therapies | Median (Range) | 2 (1-8) |

In a high-risk population of patients with R/R AML, combination therapy with CPX-351 and venetoclax produced an overall response rate of 44% and an estimated 1-year recurrence-free survival (RPS) rate of 86%. Considering responding patients, 88% (7 of 8) were able to receive allogeneic HCT. Regarding OS, a median OS of 6.1 months and a 1-year Kaplan-Meier estimate of 46% was determined. Survival was associated with treatment response, patients without prior venetoclax exposure may have better outcomes with the combination of CPX-351 and venetoclax.

Regarding safety, prolonged myelosuppression was dose limiting when combining standard dose CPX-351 with 21 days of venetoclax. A 7-day regimen of Venetoclax combined with CPX-351 was tolerable. The most commonly observed serious adverse events were infections, nausea, and prolonged cytopenias.

Example 12—Clinical Trial of CPX-351 and Venetoclax

A Phase 1b trial of CPX-351 Lower Intensity Therapy (LIT) plus venetoclax was conducted as First Line Treatment for Subjects with AML who are ineligible for Intensive Chemotherapy.

The primary objectives were to determine the maximum tolerated dose (MTD) and recommended phase 2 dose (RP2D) and to assess the safety, efficacy, and pharmacokinetics of CPX-351 lower-intensity therapy+venetoclax in patients with newly diagnosed AML who are unfit for IC.
Methods During the dose-exploration phase (3+3 design), patients received stepwise dosing of CPX-351+venetoclax 400 mg to determine the RP2D for the combination
  Dose-limiting toxicity (DLT) observation period from Days 1 to 49 (Cycle 1), with a minimum observation period of 28 days
  Patients who achieved hematologic count recovery (absolute neutrophil count [ANC]≥500/μL and platelets ≥50,000/μL) and completed the necessary assessments were allowed to proceed to Cycle 2 after they completed the minimum DLT observation period
During the expansion phase, patients received CPX-351+ venetoclax 400 mg at the identified RP2D to determine the initial response rate
Responses were measured by morphology and measurable residual disease (MRD) testing at the end of each cycle; patients with complete remission (CR), CR with incomplete neutrophil or platelet recovery (CRi), or partial response after 1 or 2 cycles were allowed to receive up to 4 cycles of CPX-351+venetoclax in the dose-exploration phase or up to 8 cycles in the expansion phase
Patients were evaluated for survival every 2 months for up to 1 year after the first administration of study treatment
Results
  Preliminary analysis includes data from 17 patients enrolled as of the data cutoff date (Sep. 21, 2021)
  Patients were considered unfit for IC based on age ≥75 years (n=9 [53%]) or Eastern Cooperative Oncology Group performance status or comorbidities (n=8 [47%]; aged 18 to 74 years)

TABLE 18

| Eligibility Criteria | |
| --- | --- |
| Inclusion criteria | Exclusion criteria |
| Histologically confirmed (per WHO criteria) newly diagnosed AML and unfit for IC Age ?≥75 years OR Age 18 to 74 years and ≥1 of the following criteria: ECOG PS 2 to 3 History of CHF requiring treatment orLVEF ≤50% DLCO ≤65% or FEVI ≤65% CrCl ≥30 to <45 mL/min Moderate hepatic impairment with total bilirubin >1.5 to ≤3.0 × ULN Other comorbidity incompatible with conventional IC ECOG PS Oto 2 if aged ≥75 years Adequate renal function: CrCl ≥30 mL/min Adequate liver function (unless considered to be due to leukemic organ involvement): AST ≤3.0 × ULN; ALT ≤3.0 × ULN; bilirubin ≤1.5 × ULN (patients aged <75 years may have bilirubin ≤3.0 × ULN) WBC count ≤25 × 10$^9$/L | ECOG PS >3 regardless of age Prior AML treatment, with the exception of hydroxyurea Favorable-risk cytogenetics per NCCN guidelines: t(8; 21), inv(16), t(16; 16), or t(15; 17) karyotype abnormalities Antecedent MPN including myelofibrosis, essential thrombocytosis, polycythemia vera, or CML with or without BCR-ABLJ translocation and AML with BCR- ABLJ translocation Acute promyelocytic leukemia CNS involvement HIV infection Hepatitis B virus or hepatitis C virus infection |

WHO, World Health Organization; AML, acute myeloid leukemia; IC, intensive chemotherapy; ECOG PS, Eastern Cooperative Oncology Group performance status; CHF, congestive heart failure; LVEF, left ventricular ejection fraction; DLCO, diffusing capacity of the lung for carbon monoxide; FEV1, forced expiratory volume in 1 second; CrCl, creatinine clearance; ULN, upper limit of normal; AST, aspartate aminotransferase; ALT, alanine aminotransferase; WBC, white blood cell; NCCN, National Comprehensive Cancer Network; MPN, myeloproliferative neoplasm; CML, chronic myelogenous leukemia; CNS, central nervous system HIV, human immunodeficiency virus.

TABLE 19

| | Dose level 1 (N = 4) | Dose level 2 (N = 7) | Dose level 1b (N = 6) | Overall (N = 17) |
|---|---|---|---|---|
| Baseline Demographic and Clinical Characteristics | | | | |
| Median (range) age, years | 82.5 (74, 87) | 74 (65, 89) | 72.5 (68, 90) | 74 (65, 90) |
| *Age cohort, n (%)* | | | | |
| 18 to 74 years | 1 (25) | 4 (57) | 4 (67) | 9 (53) |
| ≥75 years | 3 (75) | 3 (43) | 2 (33)[a] | 8 (47)[a] |
| Male, n (%) | 3 (75) | 5 (71) | 4 (67) | 12 (71) |
| *ELN risk classification, n (%)* | | | | |
| Favorable | 0 | 2 (29) | 0 | 2 (12) |
| Intermediate | 2 (50) | 2 (29) | 2 (33) | 6 (35) |
| Adverse | 2 (50) | 3 (43) | 4 (67) | 9 (53) |
| Mutated TP53, n (%)[b] | 1 (25) | 1 (14) | 2 (33) | 4 (24) |
| *AML subtype, n (%)* | | | | |
| de novo AML | 2 (50) | 6 (86) | 5 (83) | 13 (76) |
| Antecedent hematologic disorder | 1 (25) | 0 | 1 (17) | 2 (12) |
| Therapy-related AML | 1 (25) | 1 (14) | 0 | 2 (12) |
| *ECOG PS, n (%)[b]* | | | | |
| 0 | 2 (50) | 1 (14) | 0 | 3 (18) |
| 1 | 2 (50) | 3 (43) | 4 (67) | 9 (53) |
| 2 | 0 | 3 (43) | 1 (17) | 4 (24) |

ELN, European LeukemiaNet; AML, acute myeloid leukemia; ECOG PS, Eastern Cooperative Oncology Group performance status.
N = number of patients who received ≥1 dose of study drug and had sufficient data to be included in the analysis.
[a]One patient at dose level 1b turned 75 years of age in between providing informed consent and receiving treatment; the patient was therefore categorized as <75 years of age at baseline but indicated as ≥75 years of age as a reason for being considered unfit for intensive therapy.
[b]TP53 and ECOG PS data not available for 1 patient treated in dose level 1b.

No patient had received prior hypomethylating agents for the treatment of myelodysplastic syndrome

TABLE 20

Dose-exploration Levelsa and DLTs

| | Dose Level 1 | Dose Level 2 | Dose Level 1b |
|---|---|---|---|
| CPX-351 dose on Days 1 and 3[b,c] | 20 units/m² IV | 40 units/m² IV | 30 units/m² IV |
| Venetoclax dose on Days 2 to 21[b] | 400 mg/day PO | 400 mg/day PO | 400 mg/day PO |
| Enrolled patients | 4 | 7 | 3 |
| Patients evaluable for DLTs | 3 | 6 | 3 |
| Summary of DLTs | No DLTs | 1 patient experienced 2 DLTs (grade 3 TLS and liver injury) | No DLTs |

IV, intravenously; PO, orally; DLT, dose-limiting toxicity; TLS, tumor lysis syndrome.
a Each dose escalation is confirmed by a safety assessment committee.
[b]Of each 28-day cycle. Patients may receive up to 4 cycles of therapy during the dose-exploration phase.
[c]1 unit CPX-351 = 0.44 mg daunorubicin + 1 mg cytarabine.

One of 6 evaluable patients treated at dose level 2 experienced 2 DLTs; review of the overall safety profile led to a protocol amendment that permitted de-escalation to dose level 1b Three patients subsequently received dose level 1b with no DLTs and a safety profile comparable to dose level 1; together, these data established dose level 1b as the RP2D Three additional patients have been enrolled in the expansion phase at dose level 1b as of the data cutoff date and were included in the safety and efficacy analyses

TABLE 21

Completed Treatment Cycles

| | Dose level 1 (N = 4) | Dose level 2 (N = 7) | Dose level 1b (N = 6)[a] | Overall (N = 17) |
|---|---|---|---|---|
| *Number of cycles completed, n (%)* | | | | |
| <1 cycle | 0 | 2 (29) | 0 | 2 (12) |
| 1 cycle | 1 (25) | 1 (14) | 3 (50) | 5 (29) |
| 2 cycles | 1 (25) | 3 (43) | 2 (33) | 6 (35) |
| 3 cycles | 0 | 0 | 1 (17) | 1 (6) |
| 4 cycles | 2 (50) | 1 (14) | 0 | 3 (18) |

N = number of patients who received 2 ≥ 1 dose of study drug and had sufficient data to be included in the analysis.
[a]Two patients at dose level 1b were still undergoing treatment at the time of the data cutoff (Sep. 21, 2021).

TABLE 22

Summary of TEAEs

| | Dose level 1 (N = 4) | Dose level 2 (N = 7) | Dose level 1b (N = 6) | Overall (N = 17) |
|---|---|---|---|---|
| Any TEAE, n (%) | 4 (100) | 7 (100) | 6 (100) | 17 (100) |
| *Nonhematologic TEAEs in >20% of patients, n (%)[a]* | | | | |
| Diarrhea | 2 (50) | 2 (29) | 3 (50) | 7 (41) |
| Constipation | 2 (50) | 2 (29) | 1 (17) | 5 (29) |
| Decreased appetite | 1 (25) | 1 (14) | 2 (33) | 4 (24) |
| Hyponatremia | 0 | 3 (43) | 1 (17) | 4 (24) |
| Nausea | 0 | 2 (29) | 2 (33) | 4 (24) |
| Peripheral edema | 3 (75) | 1 (14) | 0 | 4 (24) |
| Any grade 3 TEAE, n (%) | 3 (75) | 7 (100) | 3 (50) | 13 (76) |

TABLE 22-continued

| | Summary of TEAEs | | | |
| --- | --- | --- | --- | --- |
| | Dose level 1 (N = 4) | Dose level 2 (N = 7) | Dose level 1b (N = 6) | Overall (N = 17) |
| Nonhematologic grade ≥3 TEAEs in >10% of patients, n (%)[b] | | | | |
| Tumor lysis syndrome | 1 (25) | 1 (14) | 0 | 2 (12) |

TEAE, treatment-emergent adverse event.

N = number of patients who received 1 dose of study drug and had sufficient data to be included in the analysis.

[a]Any grade TEAEs occurring in >20% of patients in the overall study population.

[b]Grade ≥3 TEAEs occurring in >10% of patients in the overall study population.

Grade ≥3 TEAEs were primary myelosuppression events, with febrile neutropenia reported in 5 (29%) patients; tumor lysis syndrome was the only nonhematologic grade ≥3 TEAE reported in >10% of patients There were no deaths on or before Day 30; the early mortality rate by Day 60 was 6% due to 1 death in the dose level 1 cohort (myocardial infarction that was considered unrelated to study treatment)

TABLE 23

| Hematologic Recovery Times in Patients Achieving CR or CRi After Cycle 1 | | | | |
| --- | --- | --- | --- | --- |
| | Dose level 1 | Dose level 2 | Dose level 1b | Overall |
| Time to ANC recovery ≥500/μL | | | | |
| n/N | 3/3 | 2/3a | 4/4 | 9/10 |
| Median (IQR), days | 30.0 (28, 52) | 30.0 (21, 44) | 25.5 (21, 32) | 30.0 (21, 34) |
| Time to platelet recovery ≥50,000/μL | | | | |
| n/N | 3/3 | 3/3 | 4/4 | 10/10 |
| Median (IQR), days | 21.0 (21, 52) | 22.0 (12, 28) | 23.5 (21, 27) | 21.5 (21, 28) |

CR, complete remission; CRi, complete remission with incomplete neutrophil or platelet recovery; ANC, absolute neutrophil count; IQR, interquartile range.

N = number of patients who achieved CR or CRi.

n = number of patients who achieved the specified recovery endpoint by the safety follow-up or death, whichever occurred first.

aOne patient who achieved CR or CRi in the dose level 2 cohort did not have their ANC fall below the 500/μL threshold.

Among patients who achieved CR or CRi, median ANC and platelet recovery times were generally similar between dose cohorts A best response of CR was achieved by 10/15 (67%) patients with a response assessment across dose levels; no patient achieved a best response of CRi All 10 patients who achieved CR had entered into CR or CRi after their first treatment cycle MRD-negative CR was achieved by 8/15 (53%) patients with a response assessment; of these, 4 achieved MRD negativity after Cycle 1, 2 after Cycle 2, 1 after Cycle 3, and 1 after Cycle 4

Preliminary results from this ongoing phase 1b study established an MTD and RP2D of CPX-351 30 units/m² on Days 1 and 3+venetoclax 400 mg on Days 2 to 21 in adults with newly diagnosed AML who were considered unfit or ineligible to receive IC.

The combination of CPX-351 lower-intensity therapy+ venetoclax was generally well tolerated and demonstrated promising initial efficacy, with achievement of CR in the majority of patients.

Further studies are ongoing and additional patients are being enrolled to further evaluate the RP2D.

The invention claimed is:

1. A treatment cycle for treating a hematologic proliferative disorder in a subject, which treatment cycle comprises administering to the subject venetoclax and a pharmaceutical composition comprising CPX-351 that supplies daunorubicin and cytarabine at a fixed 1:5 molar ratio, wherein the pharmaceutical composition is administered intravenously to the subject in a dosage of from 20 to 60 units/m² of CPX-351, wherein the treatment cycle is 28 days, wherein the subject achieves complete remission, or complete remission with incomplete neutrophil or platelet recovery after one to four treatment cycles, and wherein the subject achieves Minimal Residual Disease negative status after one to four treatment cycles.

2. The treatment cycle of claim 1, wherein the pharmaceutical composition comprising CPX-351 is administered on days 1, 3, and 5 and venetoclax is administered orally on days 2-21.

3. The treatment cycle of claim 1, wherein the pharmaceutical composition comprising CPX-351 is administered on days 1 and 3 and venetoclax is administered orally on days 2-21.

4. The treatment cycle of claim 1, wherein the hematologic proliferative disorder is acute lymphocytic leukemia, acute myeloid leukemia, chronic myelogenous leukemia, chronic lymphocytic leukemia or acute promyelocytic leukemia, myelodysplastic syndrome or myeloproliferative neoplasm.

5. The treatment cycle of claim 1, wherein the hematologic proliferative disorder is acute myeloid leukemia.

6. The treatment cycle of claim 1, wherein the hematologic proliferative disorder is relapsed and/or refractory acute myeloid leukemia, de novo acute myeloid leukemia, therapy-related acute myeloid leukemia, newly diagnosed acute myeloid leukemia, or newly diagnosed secondary acute myeloid leukemia.

7. The treatment cycle of claim 1, wherein the subject has an Eastern Cooperative Oncology Group performance status of from 0 to 2.

8. The treatment cycle of claim 1, wherein the subject has an Eastern Cooperative Oncology Group performance status of from 0 to 1.

9. The treatment cycle of claim 1, wherein venetoclax is administered at a dosage of from 50 to 400 mg per day.

10. The treatment cycle of claim 1, wherein venetoclax is administered at a dosage of from 100 to 400 mg per day.

11. The treatment cycle of claim 1, wherein the pharmaceutical composition is administered intravenously in a dosage of 20 units/m² of CPX-351 on days 1 and 3 and venetoclax is administered orally on days 2-21.

12. The treatment cycle of claim 1, wherein the pharmaceutical composition is administered intravenously in a dosage of 30 units/m² of CPX-351 on days 1 and 3 and venetoclax is administered orally on days 2-21.

13. The treatment cycle of claim 1, wherein the pharmaceutical composition is administered intravenously in a dosage of 40 units/m² of CPX-351 on days 1 and 3 and venetoclax is administered orally on days 2-21.

14. The treatment cycle of claim 1, wherein the subject achieves complete remission, or complete remission with incomplete neutrophil or platelet recovery, and/or and Minimal Residual Disease negative status after one treatment cycle.

15. The treatment cycle of claim 1, wherein the pharmaceutical composition is administered intravenously in a dosage of from 20 to 40 units/m$^2$ of CPX-351 on days 1 and 3 and venetoclax is administered orally in a dosage of from 100 to 400 mg on days 2-21.

16. The treatment cycle of claim 1, wherein the pharmaceutical composition is administered intravenously in a dosage of from 40 to 60 units/m$^2$ of CPX-351 on days 1 and 3 and venetoclax is administered orally in a dosage of from 100 to 400 mg on days 2-21.

17. The treatment cycle of claim 1, wherein, prior to the administering, the subject is not in complete remission or complete remission with incomplete neutrophil or platelet recovery.

18. A treatment cycle for treating a hematologic proliferative disorder in a subject, which treatment cycle comprises administering to the subject venetoclax and a pharmaceutical composition comprising CPX-351 that supplies daunorubicin and cytarabine at a fixed 1:5 molar ratio, wherein the pharmaceutical composition is administered intravenously in a dosage of from 20 to 60 units/m$^2$ of CPX-351 on days 1 and 3 of a 28 day cycle, and wherein, prior to the administering, the subject is not in complete remission or complete remission with incomplete neutrophil or platelet recovery.

19. The treatment cycle of claim 18, wherein the subject achieves complete remission, complete remission with incomplete neutrophil or platelet recovery, and/or Minimal Residual Disease negative status after one to four treatment cycles.

\* \* \* \* \*